(12) United States Patent
McKew et al.

(10) Patent No.: US 6,635,771 B2
(45) Date of Patent: Oct. 21, 2003

(54) N-BENZHYDRYL INDOLE COMPOUNDS

(75) Inventors: John C. McKew, Arlington, MA (US);
Steven Y. Tam, Wellesley, MA (US);
Katherine L. Lee, West Newton, MA (US); Lihren Chen, Cambridge, MA (US); Paresh Thakker, Boston, MA (US); Fuk-Wah Sum, Pomona, NY (US); Mark Behnke, Sommerville, MA (US); Baihua Hu, Audubon, PA (US);
James D. Clark, Acton, MA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/302,634

(22) Filed: Nov. 22, 2002

(65) Prior Publication Data

US 2003/0158405 A1 Aug. 21, 2003

Related U.S. Application Data

(60) Provisional application No. 60/419,664, filed on Oct. 18, 2002, and provisional application No. 60/334,588, filed on Dec. 3, 2001.

(51) Int. Cl.[7] .................... C07D 209/16; C07D 401/12; C07D 417/02
(52) U.S. Cl. .................... 548/491; 546/277.4; 546/201; 544/61; 544/62; 544/143; 548/146; 548/217; 548/250; 548/255; 548/312.1; 548/364.7; 548/469
(58) Field of Search .................. 548/491, 490, 548/469, 146, 217, 250, 255, 312.1, 364.7, 277.4; 544/61, 62, 143

(56) References Cited

U.S. PATENT DOCUMENTS

| | | |
|---|---|---|
| 3,505,354 A | 4/1970 | Doebel et al. |
| 3,629,284 A | 12/1971 | Yamamoto et al. |
| 3,931,229 A * | 1/1976 | Zinnes et al. ............... 548/491 |
| 4,271,263 A | 6/1981 | Goettert |
| 4,654,360 A | 3/1987 | Greenhouse et al. |
| 4,894,386 A | 1/1990 | Brown et al. |
| 5,081,145 A | 1/1992 | Guindon et al. |
| 5,166,170 A | 11/1992 | Tegeler et al. |
| 5,212,195 A | 5/1993 | Clark et al. |
| 5,229,516 A | 7/1993 | Musser et al. |
| 5,288,743 A | 2/1994 | Brooks et al. |
| 5,290,798 A | 3/1994 | Guillard et al. |
| 5,322,776 A | 6/1994 | Knopf et al. |
| 5,332,755 A | 7/1994 | Butler et al. |
| 5,354,677 A | 10/1994 | Knopf et al. |
| 5,380,739 A | 1/1995 | Clark et al. |
| 5,420,289 A | 5/1995 | Musser et al. |
| 5,424,329 A | 6/1995 | Boschelli et al. |
| 5,482,960 A | 1/1996 | Berryman et al. |
| 5,641,800 A | 6/1997 | Bach et al. |

FOREIGN PATENT DOCUMENTS

| | | |
|---|---|---|
| CH | 484111 | 1/1970 |
| DE | 18 16 335 A | 7/1970 |
| DE | 43 38 770 A1 | 5/1995 |
| EP | 0 337 766 A1 | 10/1989 |
| EP | 0 337 767 A1 | 10/1989 |
| EP | 0 620 215 A1 | 10/1994 |
| FR | 1 492 929 | 7/1967 |
| WO | WO 91/06537 A2 | 5/1991 |
| WO | WO 93/23391 A1 | 11/1993 |
| WO | WO 95/13266 A1 | 5/1995 |
| WO | WO 98/05637 A1 | 2/1998 |
| WO | WO 98/08818 A1 | 3/1998 |
| WO | WO 99/43651 A2 | 9/1999 |
| WO | WO 99/43654 A2 | 9/1999 |
| WO | WO 99/43672 A1 | 9/1999 |

OTHER PUBLICATIONS

Roy et al., Further Studies on Anti–Inflammatory Activity of Two Potent Indan–1–Acetic Acids, Ind. J. Physiol. Pharmac., Jul.–Sep. 1982, vol. 28, No. 3, pp 207–214.

Draheim et al., Indole Inhibitors of Human Nonpancreatic Secretory Phospholipase $A_{2+}$ 3 Indole–3–glyoxamides, J. Med. Chem 1996, vol. 39, No. 26, pp 5159–5175.

Dillard et al., Indole Inhibitors of Human Nonpancreatic Secretory Phospholipase $A_{2+}$ 2. Indole–3–acetamides with Additional Functionality, J. Med.chem. 1996, vol. 39, No. 26, pp 5137–5158.

Dillard et al, Indole Inhibitors of Human Nonpancreatic Secretory Phospholipase $A_{2+}$ 1. Indole–3–acetamides, J. Med. Chem., 1996, vol. 39, No. 26, pp 5119–5136.

Schevitz et al., Nature Structural Biology, vol. 2, No. 2, Jun. 1995, pp 458–465.

Doebel et al., J. Med. Chem., 1972, vol. 15, No. 10, pp 1081–1082.

* cited by examiner

Primary Examiner—Charanjit S. Aulakh
(74) Attorney, Agent, or Firm—Joseph M. Mazzarese

(57) ABSTRACT

Compounds of the formula

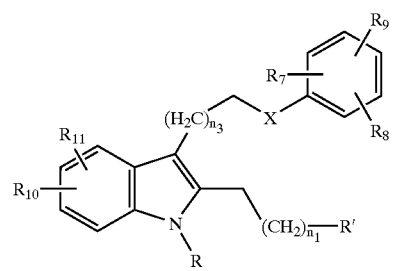

in which R, R', $R_7$–$R_{11}$, X, $n_1$ and $n_3$ are as defined herein. These compounds are useful as intermediates for preparing pharmaceutical compounds having pharmacological activity as chemical inhibitors of the activity of various phospholipase enzymes, particularly phospholipase $A_2$ enzymes.

8 Claims, No Drawings

N-BENZHYDRYL INDOLE COMPOUNDS

This application claim benefits to Provisional Application 60/419,664 filed Oct. 18, 2002 which claim benefits to Provisional Application 60/334,588 filed Dec. 3, 2001.

This invention relates to novel N-Benzhydryl indole compounds useful as intermediates in the synthesis of compounds having pharmacological activity as chemical inhibitors of the activity of various phospholipase enzymes, particularly phospholipase $A_2$ enzymes, and more specifically cytosolic phospholipase $A_2\alpha$.

BACKGROUND OF THE INVENTION

Leukotrienes and prostaglandins are important mediators of inflammation, each of which classes contributes to the development of an inflammatory response in a different way. Leukotrienes recruit inflammatory cells such as neutrophils to an inflamed site, promote the extravasation of these cells and stimulate release of superoxide and proteases which damage the tissue. Leukotrienes also play a pathophysiological role in the hypersensitivity experienced by asthmatics [See, e.g. B. Samuelson et al., Science, 237:1171–76 (1987)]. Prostaglandins enhance inflammation by increasing blood flow and therefore infiltration of leukocytes to inflamed sites. Prostaglandins also potentiate the pain response induced by stimuli.

Prostaglandins and leukotrienes are unstable and are not stored in cells, but are instead synthesized [W. L. Smith, Biochem. J., 259:315–324 (1989)] from arachidonic acid in response to stimuli. Prostaglandins are produced from arachidonic acid by the action of COX-1 and COX-2 enzymes. Arachidonic acid is also the substrate for the distinct enzyme pathway leading to the production of leukotrienes.

Arachidonic acid which is fed into these two distinct inflammatory pathways is released from the sn-2 position of membrane phospholipids by phospholipase $A_2$ enzymes (hereinafter $PLA_2$). The reaction catalyzed by $PLA_2$ is believed to represent the rate-limiting step in the process of lipid mediated biosynthesis and the production of inflammatory prostaglandins and leukotrienes. When the phospholipid substrate of $PLA_2$ is of the phosphotidyl choline class with an ether linkage in the sn-1 position, the lysophospholipid produced is the immediate precursor of platelet activating factor (hereafter called PAF), another potent mediator of inflammation [S. I. Wasserman, Hospital Practice, 15:49–58 (1988)].

Most anti-inflammatory therapies have focussed on preventing production of either prostglandins or leukotrienes from these distinct pathways, but not on all of them. For example, ibuprofen, aspirin, and indomethacin are all NSAIDs which inhibit the production of prostaglandins by COX-1/COX-2, but have no effect on the inflammatory production of leukotrienes from arachidonic acid in the other pathways. Conversely, zileuton inhibits only the pathway of conversion of arachidonic acid to leukotriense, without affecting the production of prostaglandins. None of these widely-used anti-inflammatory agents affects the production of PAF.

Consequently the direct inhibition of the activity of $PLA_2$ has been suggested as a useful mechanism for a therapeutic agent, i.e., to interfere with the inflammatory response. [See, e.g., J. Chang et al, Biochem. Pharmacol., 36:2429–2436 (1987)].

A family of $PLA_2$ enzymes characterized by the presence of a secretion signal sequenced and ultimately secreted from the cell have been sequenced and structurally defined. These secreted $PLA_2$s have an approximately 14 kD molecular weight and contain seven disulfide bonds which are necessary for activity. These $PLA_2$s are found in large quantities in mammalian pancreas, bee venom, and various snake venom. [See, e.g., references 13–15 in Chang et al, cited above; and E. A. Dennis, Drug Devel. Res., 10:205–220 (1987).] However, the pancreatic enzyme is believed to serve a digestive function and, as such, should not be important in the production of the inflammatory mediators whose production must be tightly regulated.

The primary structure of the first human non-pancreatic $PLA_2$ has been determined. This non-pancreatic $PLA_2$ is found in platelets, synovial fluid, and spleen and is also a secreted enzyme. This enzyme is a member of the aforementioned family. [See, J. J. Seilhamer et al, J. Biol. Chem., 264:5335–5338 (1989); R. M. Kramer et al, J. Biol. Chem., 264:5768–5775 (1989); and A. Kando et al, Biochem. Biophys. Res. Comm., 163:42–48 (1989)]. However, it is doubtful that this enzyme is important in the synthesis of prostaglandins, leukotrienes and PAF, since the non-pancreatic $PLA_2$ is an extracellular protein which would be difficult to regulate, and the next enzymes in the biosynthetic pathways for these compounds are intracellular proteins. Moreover, there is evidence that $PLA_2$ is regulated by protein kinase C and G proteins [R. Burch and J. Axelrod, Proc. Natl. Acad. Sci. U.S.A., 84:6374–6378 (1989)] which are cytosolic proteins which must act on intracellular proteins. It would be impossible for the non-pancreatic $PLA_2$ to function in the cytosol, since the high reduction potential would reduce the disulfide bonds and inactivate the enzyme.

A murine $PLA_2$ has been identified in the murine macrophage cell line, designated RAW 264.7. A specific activity of 2 mols/min/mg, resistant to reducing conditions, was reported to be associated with the approximately 60 kD molecule. However, this protein was not purified to homogeneity. [See, C. C. Leslie et al, Biochem. Biophys. Acta., 963:476492 (1988)]. The references cited above are incorporated by reference herein for information pertaining to the function of the phospholipase enzymes, particularly $PLA_2$.

A cytosolic phospholipase $A_2$ (hereinafter "$cPLA_2$") has also been identified and cloned. See, U.S. Pat. Nos. 5,322,776 and 5,354,677, which are incorporated herein by reference as if fully set forth. The enzyme of these patents is an intracellular $PLA_2$ enzyme, purified from its natural source or otherwise produced in purified form, which functions intracellularly to produce arachidonic acid in response to inflammatory stimuli.

Now that several phospholipase enzymes have been identified, it would be desirable to identify chemical inhibitors of the action of enzymes, which inhibitors could be used to treat inflammatory conditions, particularly where inhibition of production of prostaglandins, leukotrienes and PAF are all desired results. There remains a need in the art for an identification of such anti-inflammatory agents for therapeutic use in a variety of disease states. There also remains a need to identify novel intermediates and methods of synthesizing such therapeutic agents.

SUMMARY OF THE INVENTION

This invention comprises intermediate compounds of formula I:

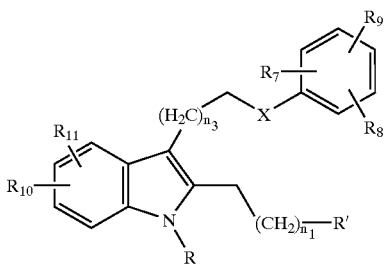

wherein

R is —$(CH_2)_n$—A, —$(CH_2)_n$—S—A, or —$(CH_2)_n$—O—A, where A represents:

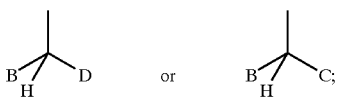

D represents $C_1$–$C_6$ alkyl, $C_1$–$C_6$ alkoxy, —$CF_3$ or —$C_{1-3}$ alkyl-$CF_3$, B and C are each independently selected from the group consisting of phenyl, pyridinyl, pyrimidinyl, furanyl, thiophenyl or pyrrolyl groups, each optionally substituted by from 1 to 3, preferably 1 to 2, substituents selected independently from the group consisting of H, halogen, —CN, —CHO, —$CF_3$, —$OCF_3$, —OH, —$C_1$–$C_6$ alkyl, $C_1$–$C_6$ alkoxy, —$NH_2$, —$N(C_1$–$C_6)_2$, —$NH(C_1$–$C_6)$, —N—C(O)—$(C_1$–$C_6)$, —$NO_2$, or by a 5- or 6-membered heterocyclic or heteroaromatic ring containing 1 or 2 heteroatoms selected from O, N or S;

R' is selected from the group consisting of —$CH_2$—OH, —$CH_2$—NH—S(O)$_2$—$(CH_2)_{n2}$-halo, —$CH_2$—NH—S(O)$_2$—CH=CH, —$CH_2$—$NH_2$, or a protected form of —$CH_2$—$NH_2$;

$R_7$ and $R_8$ are independently selected from H, halogen, —CN, —CHO, —$CF_3$, —$OCF_3$, —OH, —$C_1$–$C_6$ alkyl, $C_1$–$C_6$ alkoxy, $C_1$–$C_6$ thioalkyl, —$NH_2$, —$N(C_1$–$C_6)_2$, —$NH(C_1$–$C_6)$, —N—C(O)—$(C_1$–$C_6)$, or —$NO_2$;

$R_9$ represents —$(CH_2)_{n4}$—$CO_2H$, an ester form of —$(CH_2)_{n4}$—$CO_2H$, or a pharmaceutically acceptable acid mimic or mimetic;

$R_{10}$ is selected from H, halogen, —CN, —CHO, —$CF_3$, —$OCF_3$, —OH, —$C_1$–$C_6$ alkyl, $C_1$–$C_6$ alkoxy, $C_1$–$C_6$ thioalkyl, —$NH_2$, —$N(C_1$–$C_6)_2$, —$NH(C_1$–$C_6)$, —N—C(O)—$(C_1$–$C_6)$, or —$NO_2$;

$R_{11}$ is selected from H, halogen, —CN, —CHO, —$CF_3$, —$OCF_3$, —OH, —$C_1$–$C_6$ alkyl, $C_1$–$C_6$ alkoxy, $C_1$–$C_6$ thioalkyl, —$NH_2$, —$N(C_1$–$C_6)_2$, —$NH(C_1$–$C_6)$, —N—C(O)—$(C_1$–$C_6)$, —$NO_2$, —N—C(O)—N$(C_1$–$C_3$ alkyl)$_2$, —N—C(O)—NH$(C_1$–$C_3$ alkyl), —N—C(O)—O—$(C_1$–$C_3$ alkyl), —$SO_2$—$C_1$–$C_6$ alkyl, —S—$C_3$–$C_6$ cycloalkyl, —S—$CH_2$—$C_3$–$C_6$ cycloalkyl, —$SO_2$—$C_3$–$C_6$ cycloalkyl, , —$SO_2$—$CH_2$—$C_3$–$C_6$ cycloalkyl, $C_3$–$C_6$ cycloalkyl, —$CH_2$—$C_3$–$C_6$ cycloalkyl, —O—$C_3$–$C_6$ cycloalkyl, , —O—$CH_2$—$C_3$–$C_6$ cycloalkyl, phenyl, benzyl, benzyloxy, morpholino or other heterocycles such as pyrrolidino, piperidine, piperizine, furan, thiophene, imidazole, tetrazole, pyrazine, pyrazolone, pyrazole, imidazole, oxazole or isoxazole, the rings of each of these groups each being optionally substituted by from 1 to 3 substituents selected from the group of H, halogen, —CN, —CHO, —$CF_3$, —OH, —$C_1$–$C_6$ alkyl, $C_1$–$C_6$ alkoxy, —$NH_2$, —$N(C_1$–$C_6)_2$, —NH $(C_1$–$C_6)$, —N—C(O)—$(C_1$–$C_6)$, —$NO_2$, —$SO_2$ $(C_1$–$C_3$ alkyl), —$SO_2NH(C_1$–$C_3$ alkyl), —$SO_2N$ $(C_1$–$C_3$ alkyl)$_2$, or $OCF_3$;

n is an integer from 0 to 3;
$n_1$ is an integer from 0 to 3;
$n_2$ is an integer from 0 to 3
$n_3$ is an integer from 0 to 3;
$n_4$ is an integer from 0 to 2; and, X is a linking group selected from the group consisting of —O—, —$CH_2$—, —$SO_2$—, —NH—, and —N($C_1$–$C_6$-alkyl)—.

DETAILED DESCRIPTION OF THE INVENTION

A preferred embodiment of the invention comprises benzhydryl indole compounds of formula II:

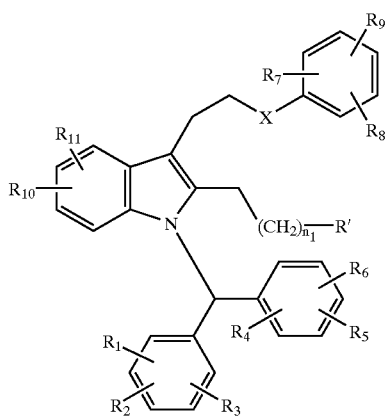

wherein:

R', $R_{7-11}$, X, $n_1$, $n_2$ and $n_4$ are as defined above; and, $R_1$, $R_2$, $R_3$, $R_4$, $R_5$ and $R_6$ are each independently selected from H, halogen, —CN, —CHO, —$CF_3$, —$OCF_3$, —OH, —$C_1$–$C_6$ alkyl, $C_1$–$C_6$ alkoxy, —$NH_2$, —$N(C_1$–$C_6)_2$, —NH $(C_1$–$C_6)$, —N—C(O)—$(C_1$–$C_6)$, —$NO_2$, or a 5- or 6-membered heterocyclic or heteroaromatic ring containing 1 or 2 heteroatoms selected from O, N or S.

The term halogen or halo is used in this specification to refer to F, Cl, Br and I. Preferred halogen atoms in the R' group —$CH_2$—NH—S(O)$_2$—$(CH_2)_{n2}$-halo include bromine and chlorine.

Preferred ester forms of the compounds of formula II wherein $R_9$ is —$(CH_2)_{n4}$—$CO_2H$, are the $C_1$–$C_8$ alkyl esters, including straight, branched and cyclic alkyl groups, and benzyl esters.

Commercially available and art recognized amine protecting groups are useful to form the protected forms of the $CH_2)_{n1}$—$CH_2$—$NH_2$ groups described above. These include those represented by the formulae below, wherein the number of carbon atoms in the chain are merely presented for illustration and do not limit the number of carbon atoms in the corresponding carbon chains of this invention.

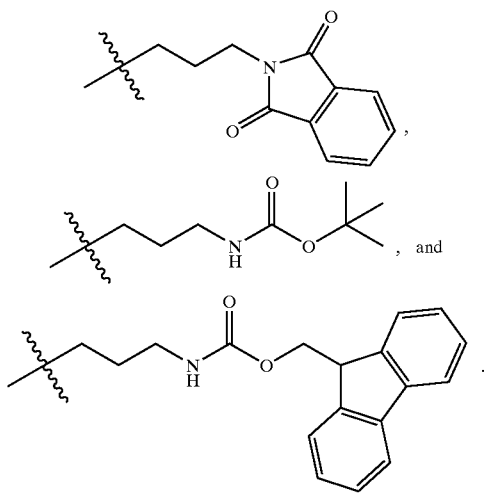

Other non-limiting examples of amine protecting groups useful with the compounds of this invention include, but are not limited to, the following:

1) amide types such as formyl, acetyl, chloroacetyl, trichloroacetyl, o-nitrophenylacetyl, o-nitrophenoxyacetyl, trifluoroacetyl, acetoacetyl, phthalyl, and p-toluenesulfonyl;

2) aromatic carbamate types such as benzyloxycarbonyl (CBZ), and benzyl substituted one or more time with with alkyl, cyano, nitro, chloro, fluoro, bromo, and methoxy; diphenylmethyl, 1-(p-biphenyl)-1-methylethyl, 9-fluorenylmethyl (Fmoc), 2-phenylethyl, and cinnamyl groups;

3) aliphatic carbamate types such as tert-butyloxycarbonyl (Boc), ethyl, diisopropylmethyl, allyl, vinyl, t-amyl, diisopropylmethyl, and isobutyl;

4) cyclic alkyl carbamate types such as cyclopentyl, cyclohexyl, cyclopropylmethyl, and adamantyl;

5) alkyl type amine protecting groups such as triphenyl-methyl (trityl) and benzyl;

6) trialkylsilane groups such as trimethylsilane, triethylsilane, triisopropylsilane, tri-t-butylsilane, triphenylsilane, tritolylsilane, trimesitylsilane, methyidiphenylsilane, dinaphthylmethylsilane, bis(diphenyl)methylsilane, etc.; and 7) thiol containing types of protecting groups, such as phenylthiocarbonyl and dithiasuccinoyl protecting groups.

Other preferred amine protecting groups for use with this invention are ethoxycarbonyl groups, acyl groups, including 4-chlorobutyryl isobutyryl, o-nitrocinnamoyl, picolinoyl, acylisothiocyanate, aminocaproyl, benzoyl and the like, and acyloxy groups including methoxycarbonyl, 9-fluorenylmethoxycarbonyl, 2,2,2-trifluoroethoxycarbonyl, 2-trimethylsilylethxoy carbonyl, vinyloxycarbonyl, allyloxycarbonyl, 1,1-dimethylpropynyloxycarbonyl, p-nitrobenzyloxycarbony, 2,4-dichlorobenzyloxycarbonyl, and the like.

Pharmaceutically acceptable acid mimics or mimetics which may appear at $R_9$ include those selected from the formulae:

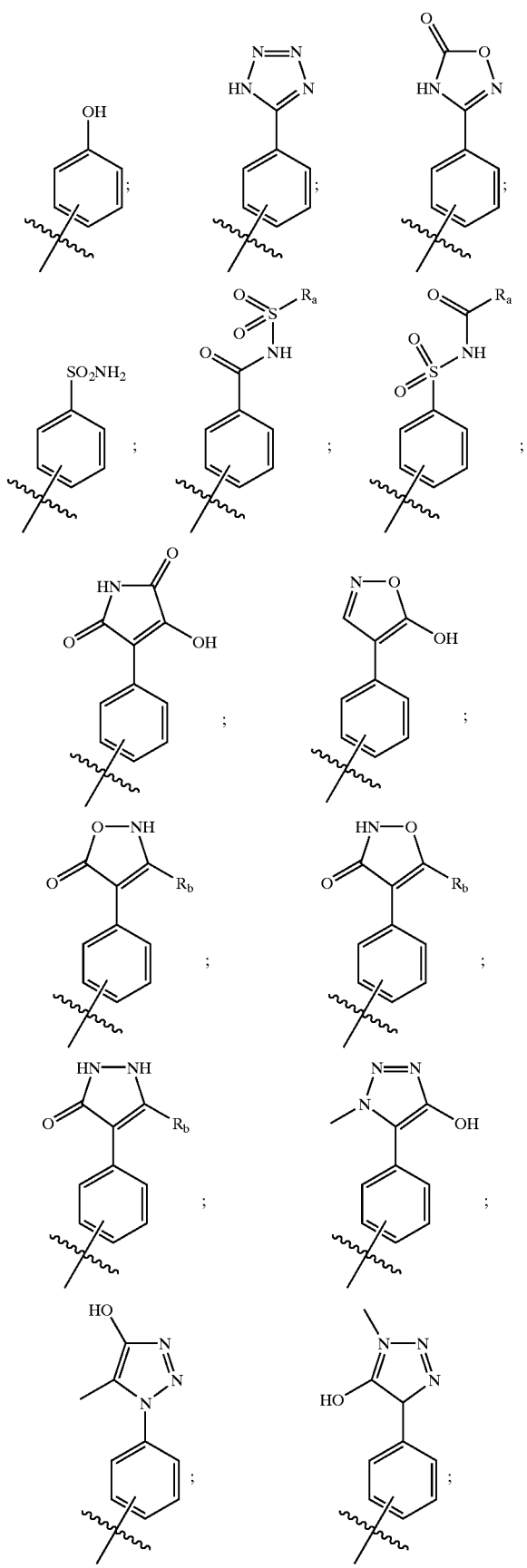

substituted by from 1 to 3 groups selected from $C_1$–$C_6$ alkyl, $C_1$–$C_6$ alkoxy, $C_1$–$C_6$ thioalkyl, —$CF_3$, halogen, —OH, or —COOH; $R_b$ is selected from —$CF_3$, —$CH_3$, —$NH_2$, phenyl, or benzyl, with the phenyl or benzyl groups being optionally substituted by from 1 to 3 groups selected from $C_1$–$C_6$ alkyl, $C_1$–$C_6$ alkoxy, $C_1$–$C_6$ thioalkyl, —$CF_3$, halogen, —OH, or —COOH; and $R_c$ is selected from —$CF_3$ or $C_1$–$C_6$ alkyl.

Another preferred embodiment of the compounds of this invention is represented by formula III:

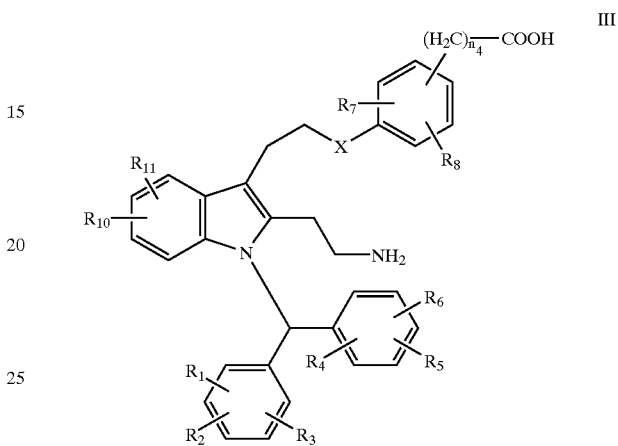

III wherein each of the variables $R_1$ through $R_{11}$, X and n4 are as defined above. A particularly preferred embodiment are compounds of formula III in which $R_1$ through $R_6$ are each hydrogen.

Another preferred embodiment of the compounds of this invention are those of formula IV:

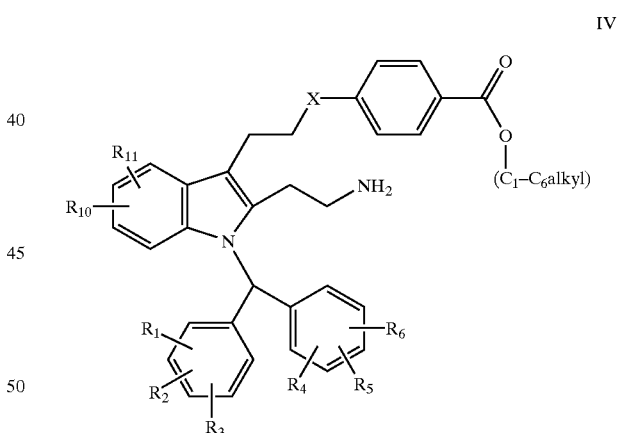

IV wherein each of the variables $R_1$ through $R_{11}$, and X are as defined above.

A particularly preferred embodiment of the of this invention are compounds of formula IV in which $R_1$ through $R_6$ are each hydrogen.

Among the most preferred compounds of the present invention are the compounds below which are designated Intermediates No. 1, 2 and 3. An illustrative method for making these intermediates is also shown. These examples of highly preferred compounds and methods should not be construed as limiting the scope of the invention.

Intermediate No. 1

4{2-[2-(2-Amino-ethyl)-1-benzyhydryl-5-chloro-1H-indol-3-yl]-ethanesulfonyl}-benzoic acid methyl ester.

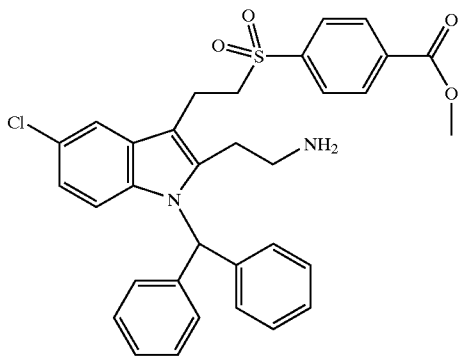

Step 1: 2-Bromo-4-chloroaniline(1.0 eq) was dissolved in CH$_2$Cl$_2$ (0.25M), then triethylamine and triflouroacetyl anhydride(1.1 eq each) were added. The resulting mixture was stirred at room temperature for 1 hour. Solvent was then stripped-off from the reaction mixture, and the residue was purified by flash chromatography with dichloromethane as eluent to give the described product in 97% yield. m/z(M−H)300.0.

Step 2: N-(2-Bromo4-chlorophenyl)-2,2,2-trifluoroacetamide(step 1, 1.0 eq) was mixed with 3-butyn-1-ol(2.0 eq), dichlorobis(triphenylphosphine)palladium(II) (2.5% eq), triethylamine(3.0 eq), CuI(5% eq) in DMF(0.2M) in a sealed vessel under N$_2$ and heated to 120° C. for 4 hours. The reaction mixture was then diluted with ethyl acetate, washed with brine and dried over Na$_2$SO$_4$. Furthermore, evaporate the solvent and the residue was purified by flash column chromatography with 2% MeOH/CH$_2$Cl$_2$ to give the described 2-(5-Chloro-1H-indol-2-yl)ethanol in 67% yield. m/z(M−H)194.09

Step 3: 2-(5-chloro-1H-indol-2-yl)ethanol (1 eq) was added to a solution (under N$_2$) containing tert-Butyldiphenylchlorosilane (1.2 eq), imidazole (2.5 eq), and DMF (1.8M). The reaction was stirred overnight. Quenched with NaHCO$_3$ $_{(aq)}$ and extracted with a Et$_2$O/EtOAc mixture. The organic layer was washed with water and brine and dried over sodium sulfate. Purified with silica gel column and 1:4 Hexane/CH$_2$Cl$_2$ as eluent. Obtained 2-({[tert-butyl(diphenyl)silyl]oxy}ethyl)-5-chloro-1H-indole (yellow oil) in 98% yield.

Step 4: Methyl 4-[(2-oxoethyl)sulfanyl]benzoate (3.7 eq) was added to a solution containing 2-({[tert-butyl(diphenyl)silyl]oxy}ethyl)-5-chloro-1H-indole (1 eq), TFA (3 eq), and 1,2-dichloroethane (0.1M) at 0° C. under N$_2$. Then Et$_3$SiH (12 eq) was added and the reaction was allowed to return to room temperature and stirred overnight. Quenched reaction with NaHCO$_3{(aq)}$ and extracted with EtOAc and washed with brine and dried over sodium sulfate. Purified with silica gel column and 1:5 EtOAc/Hexane as eluent. Obtained methyl 4-({2-[2-(2{[tert-butyl(diphenyl)silyl]oxy}ethyl)-5-chloro-1H-indol-3-yl]ethyl}sulfanyl)benzoate (yellow solid) in 79% yield.

Step 5: Methyl 4-({2-[2-(2-{[tert-butyl(diphenyl)silyl]oxy}ethyl)-5-chloro-1H-indol-3-yl]ethyl}sulfanyl)benzoate (1 eq) was added to a suspension of NaH (1.1 eq) in DMF (0.37M) at 0° C. under N$_2$. After 30 minutes Ph$_2$CHBr (1.8 eq) was added and the reaction was warmed to room temperature. After 3 hours the reaction was quenched with NH$_4$Cl$_{(aq)}$ and extracted with EtOAc/Et$_2$O mix and washed with water and brine and dried over sodium sulfate. Purified with silica gel column and 1:5 EtOAc/Hexane. Obtained methyl 3-[4-({2-[1-benzhydryl-2-(2-{[tert-butyl(diphenyl)silyl]oxy}ethyl)-5-chloro-1H-indol-3-yl]ethyl}sulfanyl)phenyl]benzoate (yellow gum) in 65% yield.

Step 6: NMO (4 eq) was added to a solution/suspension containing methyl 3-[4-({2-[1-benzhydryl-2-(2-{[tert-butyl(diphenyl)silyl]oxy}ethyl)-5-chloro-1H-indol-3-yl]ethyl}sulfanyl)phenyl]benzoate (1 eq), ACN (0.1M), and molecular sieves (1 g/mmole of benzoate) under N$_2$. After 10 minutes TPAP (0.12 eq) was added and the mixture was heated to 40° C. After 1.5 hours the reaction was cooled and filtered and the filtrate was collected. Purified with silica gel column and 1:5 EtOAc/Hexane. Obtained methyl 3-[4-({2-[1-benzhydryl-2-(2-{[tert-butyl(diphenyl)silyl]oxy}ethyl)-5-chloro-1H-indol-3-yl]ethyl}sulfonyl)phenyl]benzoate (white solid) in 71% yield.

Step 7: Tetrabutylammonium fluoride (1M in THF) (1.2 eq) was added to a solution of methyl 3-[4-({2-[1-benzhydryl-2-(2-{[tert-butyl(diphenyl)silyl]oxy}ethyl)-5-chloro-1H-indol-3-yl]ethyl}sulfonyl)phenyl]benzoate (1 eq) and THF (0.1M) at 0° C. under N$_2$. Warmed reaction to room temperature and after 1 hour quenched with NH$_4$Cl$_{(aq)}$. Extracted with EtOAc and washed with brine and dried over sodium sulfate. Purified with silica gel column and 1:9 EtOAc/CH$_2$Cl$_2$. Obtained methyl 3-[4-({2-[1-benzhydryl-5-chloro-2-(2-hydroxyethyl)-1H-indol-3-yl]ethyl}sulfonyl) phenyl]benzoate (white solid) in 86% yield.

Step 8: CH$_3$SO$_2$Cl (2 eq) and Et$_3$N (2.5 eq) were added to a solution of methyl 3-[4-({2-[1-benzhydryl-5-chloro-2-(2-hydroxyethyl)-1H-indol-3-yl]ethyl}sulfonyl)phenyl]benzoate (1 eq) in CH$_2$Cl$_2$ (0.02M) at 0° C. under N$_2$. After 1 hour the reaction was warmed to room temperature. After an additional hour water was added and extracted with CH$_2$Cl$_2$ and washed with brine and dried over sodium sulfate. Removed solvent to obtain methyl 3-(4-{[2-(1-benzhydryl-5-chloro-2-{2-[(methylsulfonyl)oxy]ethyl)1H-indol-3-yl)ethyl]sulfonyl}phenyl)benzoate (light-yellow solid) in 99% yield.

Step 9: Methyl 3-(4-{[2-(1-benzhydryl-5-chloro-2-{2-[(methylsulfonyl)oxy]ethyl}-1 H-indol-3-yl)ethyl] sulfonyl}phenyl)benzoate (1 eq), sodium azide (5 eq), and DMF (0.05M) were placed together under N$_2$ and heated to 60° C. After 1 hour the reaction was cooled and water was added. Extracted with EtOAc/Et$_2$O mix and washed with water and brine and dried over sodium sulfate. Removed solvent to obtain methyl 3-[4-({2-[2-(2-azidoethyl)-1-benzhydryl-5-chloro-1H-indol-3-yl]ethyl}sulfonyl)phenyl] benzoate (light-yellow solid) in 99% yield.

Step 10: Methyl 3-[4-({2-[2-(2-azidoethyl)-1-benzhydryl-5-chloro-1H-indol-3-yl]ethyl}sulfonyl)phenyl]benzoate (1 eq), PPh$_3$ (2 eq), and THF (0.1M) were placed together under N$_2$ and stirred overnight. Water (1 mL /1 mmole benzoate) was added and reaction was again stirred overnight. The solution was concentrated and purified with silica gel column and 3:1 EtOAc/Hexane followed by 5% MeOH in CH$_2$Cl$_2$. Obtained methyl 3-[4-({2-[2-(2-aminoethyl)-1-benzhydryl-5-chloro-1H-indol-3-yl] ethyl}sulfonyl)phenyl]benzoate (light-yellow solid) in 99% yield.

Synthesis of Intermediate No. 1 is also described below in Example 135, Steps 1–8. This intermediate could also be synthesized by method K or method M, which are set forth below.

Intermediate No. 2

4-{2-[2-(2-Amino-ethyl)-1-benzyhydryl-5-chloro-1H-indol-3-yl]-ethoxy}-benzoic acid methyl ester.

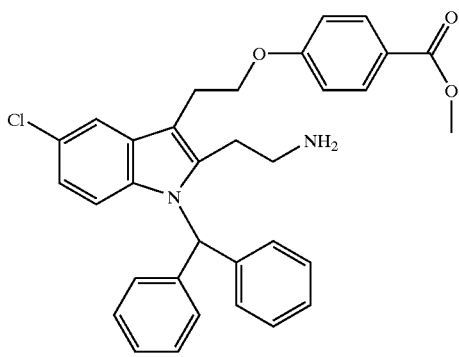

Step 1: To 4-hydroxy-benzoic acid methyl ester (1.0 eq) in DMF (0.83 M) was added K$_2$CO$_3$ (2.0 eq) followed by 2-bromo-1,1-diethoxy-ethane and the reaction mixture was stirred at 110° C. for 2 days. TLC showed a new spot. The reaction mixture was diluted with ethyl acetate, washed with 1 N NaOH, water, and brine, dried over sodium sulfate, and solvent was removed to afford desired product in 84% yield. This material was used in the next step without further purification.

Step 2: To the above product (1.0 eq) and 5-chloro-2-methyl indole (1.0 eq) in CH$_2$Cl$_2$ (0.12 M) was added triethylsilane (3.0 eq) followed by trifluoroacetic acid (3.0 eq). After being stirred overnight at room temperature, added water and trifluroacetic acid (1.0 eq) to the reaction mixture, stirred at room temperature for two days, diluted with CH$_2$Cl$_2$, washed with 1N NaOH, water, brine, dried over sodium sulfate. Trituration of the material with CH$_2$Cl$_2$ and hexanes afforded the C$_3$ alkylated indole in 92% yield Step 3: To the indole from above (1.0 eq) in DMF (0.36 M) at 25° C. was added NaH (1.2 eq, 60% dispersion in oil), and the brown solution was stirred at 0 to −5° C. for 1 h and then compound bromodiphenylmethane was added (1.1 eq), and then the reaction mixture was stirred overnight. It was then quenched with water, diluted with ethyl acetate, washed with water and brine, dried over sodium sulfate and purified by column chromatography to yield 72% of the desired product.

Step 4: To the N-alkylated indole from above (1.0 eq) in CCl$_4$ (0.2 M) was added N-bromosuccinimide (2.0 eq) and a catalytic amount of benzoyl peroxide. The solution was heated to reflux for 3 h, cooled to 25° C., filtered, and the solid was washed with CCl$_4$. The filtrate was concentrated to a foam, which was dried. The foam was dissolved in acetone, and Ag$_2$CO$_3$ (1.1 eq.) was added followed by water and the reaction mixture was stirred overnight at room temperature. It was filtered and washed with acetone. The filtrate was concentrated to a residue, to which was added water. This mixture was extracted with ethyl acetate, washed with brine, dried over sodium sulfate and then chromatographic purification on the residue gave the desired product in 85% yield. Alternatively the dibromide from the reaction with NBS could be poured into DMSO (10–20% concentration by weight) stirred for 30 minutes at room temperature. When the reaction was deemed complete it was poured into water and the resulting precipitate was isolated by filtration, the cake was washed with water and dried to yield an essentially quantitative yield.

Step 5: To the above aldehyde (1.0 equiv) in CH$_3$NO$_2$ (0.2 M) was added ammonium acetate (4 equiv) and the resulting mixture was heated to reflux for 4 h. The reaction mixture was then diluted with EtOAc and washed with brine. The aqueous phase was extracted with EtOAc. The combined organic extracts were washed with brine, dried over sodium sulfate, and concentrated until an orange crystalline solid precipitated. The mixture was refrigerated overnight and the nitroolefin (76% yield) was collected by filtration. Evaporation of the solution phase and purification of the residue by column chromatography (gradient elution 100% toluene→1% EtOAc-toluene) afforded an additional amount of the nitroolefin (23% yield).

Step 6: Zinc dust (20 equiv) was suspended in 5% aqueous HCl solution (8 M Zn/5% HCl). To this mixture was added HgCl$_2$ (0.28 equiv). The mixture was shaken for 10 min, the aqueous phase was decanted and replaced with fresh 5% HCl, and again the mixture was shaken for 5 min and the aqueous phase was removed. The zinc-mercury amalgam thus generated was then added to a mixture of the nitroolefin (1.0 equiv) and conc. HCl (80 equiv) in THF (0.04 M nitroolefin/THF). The mixture was maintained at a gentle reflux for 1 h. The formation of product was followed by TLC analysis. The mixture was cooled to room temperature and the solids were removed by filtration through Celite. Conc. NH$_4$OH was added to the solution phase and the mixture was concentrated on the rotary evaporator. The residue was dissolved in CH$_2$Cl$_2$ and conc. NH$_4$OH. The aqueous phase was extracted with CH$_2$Cl$_2$, and the organic phase was washed with brine, dried over sodium sulfate, and concentrated. Purification by column chromatography afforded the desired product (65% yield).

Synthesis of Intermediate No. 2 is also described in Example 1, Steps 1–6. This intermediate could also be synthesized using methods K, L, or M, as set forth below.

Intermediate No. 3

4-{3-[2-(2-Amino-ethyl)-1-benzyhydryl-5-chloro-1H-indol-3-yl]-propyl}-benzoic acid methyl ester

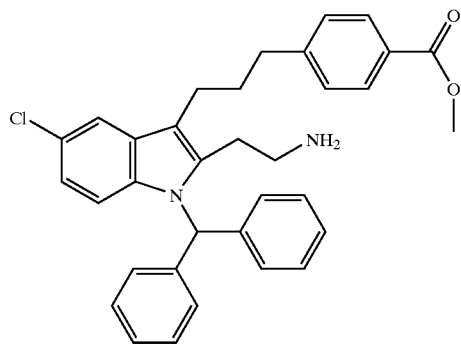

Step 1: A mixture of methyl-4-iodobenzoate (5.3 g, 20.2 mmol), allyl alcohol (1.78 g, 30.3 mmol), NaHCO$_3$ (4.24 g, 50.5 mmol), Pd(OAc)$_2$ (0.14 g, 0.60 mmol), (n-Bu)$_4$NBr (6.55 g, 20.2 mmol) and 4-Å molecular Sieves (4.1 g) in anhydrous DMF (69 mL) was stirred at room temperature for 4 days. The reaction mixture was filtered through celite and the filtrate poured onto water and extracted with EtOAc. Organic layer was washed with brine, dried (Na$_2$SO$_4$), and concentrated under vaccum. Flash chromatography (silica gel, 10–20% EtOAc-hexanes) gave 2.11 g (85% based on the recovered starting material) of the desired 4-(3-Oxo-propyl)-benzoic acid methyl ester as a clear oil.

Step 2: To a solution of 5-chloro-2-methylindole (0.86 g, 5.2 mmol) and 4-(3-Oxo-propyl)-benzoic acid methyl ester (1.0 g, 5.2 mmol) in methylene chloride (5 mL), was added TFA (1.78 g, 15.6 mmol), followed by triethylsilane (1.81 g, 15.6 mmol). The reaction mixture was stirred overnight, quenched with sat. NaHCO$_3$ solution (50 mL), and organic layer was washed with sat. NaHCO$_3$ solution, water, brine, and dried (Na$_2$SO$_4$). Solvent was removed under reduced pressure, and the residue was purified by flash column chromatography with 10–20% EtOAc/hexanes to yield the desired product in 94% (1.67 g) yield.

Step 3: To a solution of the product from step 2 (1.66 g, 4.86 mmol) in DMF (20 mL) was added NaH (60% in mineral oil, 0.24 g, 5.83 mmol) under N$_2$ atmosphere. The mixture was stirred for 1 h at room temperature, followed by the dropwise addition of benzhydryl bromide (1.8 g, 7.29 mmol) in DMF (5 mL). This reaction mixture was stirred overnight at room temperature. Water (50 mL) was added to reaction mixture, it was extracted with EtOAc, washed with brine, dried (Na$_2$SO$_4$), and concentrated under reduced pressure to a brown syrup, which was purified by silica-gel chromatography using 10% EtOAc/hexanes as eluent to isolate 4 as a white solid in 59% (1.47 g) yield.

Step 4: The product from above (1.46 g, 2.87 mmol) was dissolved in CCl$_4$ (14.5 mL), followed by the addition of NBS (1.02 g, 5.73 mmol) and benzoyl peroxide (2 mg). The reaction mixture was heated to reflux for 1 h (until all the starting material disappeared). This mixture was cooled to room temperature, filtered and the solid was washed with CCl$_4$. The filtrate was evaporated to a brown residue, which was dissolved in acetone (40 mL) and water (4 mL), Ag$_2$CO$_3$ (1.75 g, 3.16 mmol) was then added to this solution and after being stirred overnight at room temperature, it was filtered through celite, the solvent was evaporated under reduced pressure, and water was added to the residue. It was extracted with EtOAc, washed with brine, dried (Na$_2$SO$_4$), and evaporated to a syrup, which was purified by 10% EtOAc/hexanes to isolate the 2-formyl indole (1.13 g) in 75% yield. Alternatively the dibromide from the reaction with NBS could be poured into DMSO (10–20% concentration by weight) and stirred for 30 minutes at room temperature. When the reaction was deemed complete it was poured into water and the resulting precipitate was isolated by filtration, the cake was washed with water and dried to yield an essentially quantitative yield.

Step 5: To a solution of the 2 formyl indole from above (0.52 g, 1 mmol) in CH$_3$NO$_2$ (6.2 mL) was added NH$_4$OAC (0.077 g, 1 mmol), the mixture was heated to reflux for 1 h, NH$_4$ OAc (0.077 g, 1 mmol) was then added, heating at reflux was continued for an additional 1 h, NH$_4$Oac (0.077 g, 1 mmol) was added again and the heating continued for further 1 h. The reaction mixture was allowed to attain room temperature, EtOAc (50 mL) was added, followed by the addition of 100 mL water. The aqueous layer was extracted with EtOAc, and the combined organic layers were washed with brine, dried (Na$_2$SO$_4$), and evaporated to a yellow foam, which was subjected to chromatographic purification using 10% EtOAc/hexanes as an eluent to yield 6 as a yellow foam in 68% yield (0.38 g).

Step 6: Zn(Hg) was made by adding HgCl$_2$ ( 3.4 g, 7.2 mmol) to a mixture of Zn-dust (34.68 g, 530.35 mmol) and 5% HCl (38 mL) in a 100 mL beaker, this mixture was stirred vigorously for 10 min. Aqueous phase was decanted and added 38 mL of 5% HCl again and the mixture was stirred for 10 min. Aqueous phase was decanted. This solid was added to the vinyl nitro compound 6 (15 g, 26.57 mmol) in THF (660 mL) and conc. HCl (64.5 mL). This mixture was stirred at room temperature for 1 h, then at reflux for 15 min. The reaction mixture was cooled to room temperature and filtered through celite. Aq. NH$_4$OH solution (200 mL) was added to the filtrate, stirred for 15 min and THF was removed under reduced pressure. The aqueous layer was extracted with CH$_2$Cl$_2$, combined organic layer was washed with brine, dried (Na2SO4) and concentrated to a brown foam, which was purified by column chromatography by eluting the column with CHCl$_3$ in the beginning to remove non-polar impurities then with 2% MeOH/CHCl$_3$ to isolate the desired amine in 46% yield (6.1 g).

Synthesis of Intermediate No. 3 is also described below in Example 42, Steps 1–6. This intermediate could also be formed using Methods J, K, or M, as set forth below.

Intermediate No. 4

4-{2-[2-(2-Amino-ethyl)-1-benzhydryl-5-chloro-1H-indol-3-yl]-ethylamino}-benzoic acid methyl ester

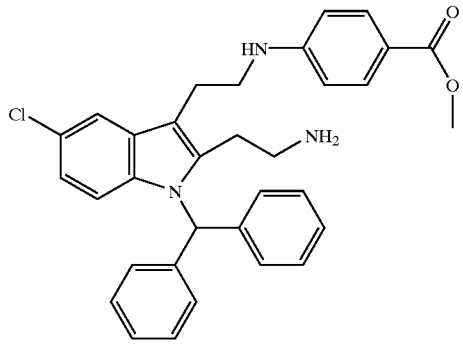

Step 1: To a solution of 4-chloro-2-iodoaniline (16.5 g, 65.1 mmol) in DMF (250 mL) at rt were added α-bromodiphenylmethane (21.5 g, 84.6 mmol) and $^i$Pr$_2$NEt (23 mL, 130 mmol) and the reaction mixture was heated at 45° C. overnight. After the volatile was removed under reduced pressure, the residue was dissolved in EtOAc, washed with water (3×) and brine and dried over MgSO$_4$. Purification on SiO$_2$ column chromoatography (hexanes to 5% EtOAc/hexanes) gave the desired Benzhydryl-(4-chloro-2-iodo-phenyl)-amine (26.1 g, 97% yield) as a yellowish solid.

Step 2: A mixture of benzhydryl-(4-chloro-2-iodo-phenyl)-amine (26.1 g, 62.2 mmol), PdCl$_2$(PPh$_3$)$_2$ (1.90 g, 2.67 mmol), CuI (1.2 g, 6.2 mmol), 3-butyn-1-ol, and Et$_3$N (120 mL) was stirred at 45° C. for 20 hours. The reaction mixture was filtered through celite and rinsed with EtOAc. The filtrate was concentrated, redissolved in EtOAc, washed with water (3×) and brine, and dried over MgSO$_4$. The crude 4-[2-(Benzhydryl-amino)-5-chloro-phenyl]-but-3-yn-1-ol (25.5 g) was used in the next step directly without further purification.

Step 3: A solution of the crude 4-[2-(benzhydryl-amino)-5-chloro-phenyl]-but-3-yn-1-ol (25.5 g) and CuI (2.7 g, 14.1 mmol) in DMF (200 mL) was heated at 125° C. for 24 hours. The reaction mixture was filtered through celite and rinsed with EtOAc. The filtrate was concentrated, redissolved in EtOAc, washed with water (3×) and brine, and dried over MgSO$_4$. Silica gel column chromatography (30% EtOAc/hexanes) yielded the desired 2-(1-Benzhydryl-5-chloro-1H-indol-2-yl)-ethanol as a yellow solid (14.5 g, 73% over 2 steps).

Step 4: To a solution of 2-(1-benzhydryl-5-chloro-1H-indol-2-yl)-ethanol (15.3 g, 42.3 mmol) in CH$_2$Cl$_2$ (190 mL) at 0° C. were added imidazole (3.72 g, 55.0 mmol) and TBDPSCl (13.2 mL, 50.8 mmol). After stirring at the same temperature for 1.5 hours, the reaction mixture was washed with cold water (3×) and brine, and dried over MgSO$_4$. The crude silyl ether was used in the next step directly without further purification.

Step 5: To a solution of the crude silyl ether in Et$_2$O (200 mL) at 0° C. was added oxalyl chloride (4.84 mL, 55.5 mmol) dropwise. The reaction mixture was allowed to warm to rt and stirring continued for 4 hours before Et₃N (35 mL) and MeOH (10 mL) were added. The mixture was washed with water, brine, and dried over MgSO₄. The crude keto ester was used directly in the next step.

Step 6: To the keto ester in THF (300 mL) was added BH₃.Me₂S (10 M, 36 mL) dropwise at rt and the reaction mixture was refluxed overnight. The mixture was cooled at 0° C. before NaOH (30%, 150 mL) was added and stirring continued for 30 min. THF was removed under reduced pressure and the reaction mixture was extracted with EtOAc, washed with water, brine, and dried over MgSO₄. Purification on column chromatography (15 to 20% EtOAc/hexanes) yielded the desired product as a white solid (15.9 g, 24.7 mmol, 58% over 3 steps).

Step 7: To a solution of oxalyl chloride (0.372 mL, 4.27 mmol) in CH₂Cl₂ (10 mL) at −78° C. was added DMSO (0.661 mL, 9.31 mmol) dropwise. The reaction mixture was stirred at the same temperature for 5 min before a solution of 2-{1-benzhydryl-2-[2-(tert-butyl-diphenyl-silanyloxy)-ethyl]-5-chloro-1H-indol-3-yl}ethanol (2.50 g, 3.88 mmol) in CH₂Cl₂ (8 mL) was introduced. After additional 40 min stirring, $^i$Pr₂NEt (3.38 mL, 19.4 mmol) was added and the reaction was quenched with cold water (5 mL) and extracted with CH₂Cl₂. The organic layer was dried over MgSO₄ and evaporated. The crude {1-Benzhydryl-2-[2-(tert-butyl-diphenyl-silanyloxy)-ethyl]-5-chloro-1H-indol-3-yl}-acetaldehyde was used directly in the next step.

Step 8: To a solution of the crude aldehyde (3.88 mmol) in 1,2-dichloroethane (39 mL) at 0° C. were added methyl 4-aminobenzoate (645 mg, 4.27 mmol), acetic acid (1.33 mL), and NaBH(OAc)₃. The reaction mixture was allowed to warm to rt overnight and quenched with cold NaHCO₃. An extractive workup furnished the desired 4-(2-{1-Benzhydryl-2-[2-(tert-butyl-diphenyl-silanyloxy)-ethyl]-5-chloro-1H-indol-3-yl}-ethylamino)-benzoic acid methyl ester which was used directly in the next step without further purification.

Step 9: To 4-(2-{1-benzhydryl-2-[2-(tert-butyl-diphenyl-silanyloxy)-ethyl]-5-chloro-1H-indol-3-yl}-ethylamino)-benzoic acid methyl ester (3.88 mmol) in THF (25 mL) at 0° C. was added a mixture of HOAc:1M TBAF (in THF) (2.3 mL:5.8 mL) and the reaction mixture was allowed to stir at rt for 18 h. Extractive workup followed by trituration with 5%EtOAc/hex gave the desired 4-{2-[1-Benzhydryl-5-chloro-2-(2-hydroxy-ethyl)-1H-indol-3-yl]-ethylamino}-benzoic acid methyl ester with slight impurity as an off-white solid (92%, over 3 steps).

Step 10: To a solution of 4-{2-[1-benzhydryl-5-chloro-2-(2-hydroxy-ethyl)-1H-indol-3-yl]-ethylamino)benzoic acid methyl ester (1.64 g, 3.04 mmol) in CH₂Cl₂ at 0° C. were added Et₃N (0.636 mL, 4.56 mmol) and MsCl (0.282 mL, 3.64 mmol). After stirring at the same temperature for 35 min, the reaction mixture was quenched with cold water. An extractive workup revealed the crude mesylate as an off-white solid (1.70 g, 90%).

Step 11: A solution of the crude mesylate (1.70 g, 2.75 mmol) and NaN₃ (89 mg, 13.8 mmol) in DMF (14 mL) was stirred at 80° C. for 6 h. The reaction mixture was diluted with EtOAc and subjected to an aqueous workup followed by flash column chromatography to yield the desired 4-{2-[2-(2-Azido-ethyl)-1-benzhydryl-5-chloro-1H-indol-3-yl]-ethylamino}-benzoic acid methyl ester (813 mg, 52% yield).

Step 12: To 4-{2-[2-(2-azido-ethyl)-1-benzhydryl-5-chloro-1H-indol-3-yl]-ethylamino}-benzoic acid methyl ester (400 mg, 0.709 mmol) in THF (4 mL) at 0° C. was added Ph₃P (223 mg, 0.851 mmol) in portions. The reaction mixture was stirred at rt for 11 h and 35° C. for 4 h before water (50 uL) was added and stirring continued overnight. The reaction mixture was diluted with EtOAc, dried with MgSO₄ and purified by flash column chromatography (EtOAc to 20%MeOH/EtOAc with 1% Et₃N) to give the desired 4-{2-[2-(2-Amino-ethyl)-1-benzhydryl-5-chloro-1H-indol-3-yl]-ethylamino}-benzoic acid methyl ester (201 mg, 53%) as a solid.

Synthesis of Intermediate No. 4 is also described below in Example 142, Steps 1–12.

Intermediate No. 5

4-({2-[2-(2-Amino-ethyl)-1-benzhydryl-5-chloro-1H-indol-3-yl]-ethyl}-methyl-amino)-benzoic acid methyl ester

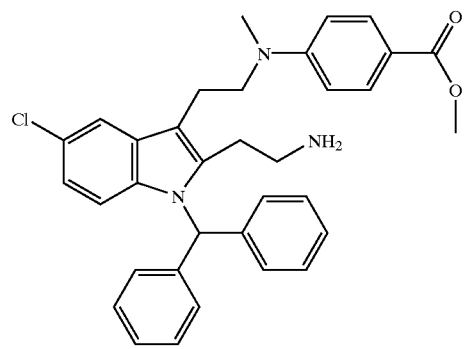

Step 1: Crude {1-Benzhydryl-2-[2-(tert-butyl-diphenyl-silanyloxy)-ethyl]-5-chloro-1H-indol-3-yl}-acetaldehyde from Intermediate No. 4 synthesis Step 7 was treated with 4-Methylamino-benzoic acid methyl ester according to the procedure in Intermediate No. 4 step 8 to yield the desired 4-[(2-{1-Benzhydryl-2-[2-(tert-butyl-diphenyl-silanyloxy)-ethyl]-5-chloro-1H-indol-3-yl}-ethyl)-methyl-amino]-benzoic acid methyl ester in 73% yield.

Step 2: The title compound was prepared according to the procedure described for Intermediate No 4 step 9. The crude 4-({(2-[1-Benzhydryl-5-chloro-2-(2-hydroxy-ethyl)-1H-indol-3-yl]-ethyl}methyl-amino)-benzoic acid methyl ester was used in the next step directly without further purification.

Step 3–6: 4-({2-[2-(2-Azido-ethyl)-1-benzhydryl-5-chloro-1H-indol-3-yl]-ethyl}-methyl-amino)-benzoic acid methyl ester was prepared according to the procedure described for Intermediate No. 4 steps 10–12 in 61% (3 steps).

Step 7: A solution of 4-({2-[2-(2-azido-ethyl)-1-benzhydryl-5-chloro-1H-indol-3-yl]-ethyl}methyl-amino)-benzoic acid methyl ester (410 mg, 0.709 mmol) and 10% Pd/C (155 mg) in MeOH:CH₂Cl₂(=7 mL:1 mL) was stirred under H₂ atmosphere (1 atm) for 2h15 min. The reaction mixture was filtered through celite and rinsed with MeOH and CH₂Cl₂. Flash column chromatography (CH₂Cl₂ to 8% MeOH/CH₂Cl₂) of the residue gave the desired 4-({2-[2-(2-Amino-ethyl)-1-benzhydryl-5-chloro-1H-indol-3-yl]-ethyl}-methyl-amino)-benzoic acid methyl ester in 78% yield (305 mg).

Synthesis of Intermediate No. 5 is also described below in Example 146, Steps 1–7.

The compounds of this invention may be used as intermediates in the synthesis of pharmaceutically useful compounds of formula V:

V

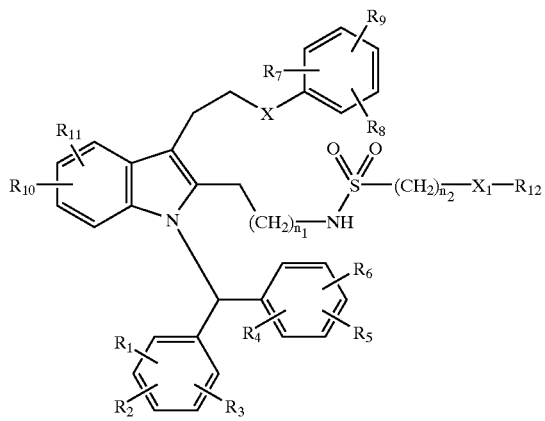

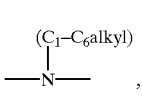

wherein:

X is a linking group selected from of —O—, —$CH_2$—, —$SO_2$—, —NH—, and —N($C_1$-$C_6$-alkyl)—;

$R_1$, $R_2$, $R_3$, $R_4$, $R_5$ and $R_6$ are each independently selected from H, halogen, —CN, —CHO, —$CF_3$, —$OCF_3$, —OH, —$C_1$-$C_6$ alkyl, $C_1$-$C_6$ alkoxy, —$NH_2$, —N($C_1$-$C_6$)$_2$, —NH($C_1$-$C_6$), —N—C(O)—($C_1$-$C_6$), —$NO_2$, or a 5- or 6-membered heterocyclic or heteroaromatic ring containing 1 or 2 heteroatoms selected from O, N or S;

$R_7$ and $R_8$ are independently selected from H, halogen, —CN, —CHO, —$CF_3$, —$OCF_3$, —OH, —$C_1$-$C_6$ alkyl, $C_1$-$C_6$ alkoxy, $C_1$-$C_6$ thioalkyl, —$NH_2$, —N($C_1$-$C_6$)$_2$, —NH($C_1$-$C_6$), —N—C(O)—($C_1$-$C_6$), or —$NO_2$;

$R_9$ is the formula —$(CH_2)_{n4}$—$CO_2H$ or a pharmaceutically acceptable acid mimic or mimetic, as defined above;

$R_{10}$ is selected from H, halogen, —CN, —CHO, —$CF_3$, —$OCF_3$, —OH, —$C_1$-$C_6$ alkyl, $C_1$-$C_6$ alkoxy, $C_1$-$C_6$ thioalkyl, —$NH_2$, —N($C_1$-$C_6$)$_2$, —NH($C_1$-$C_6$), —N—C(O)—($C_1$-$C_6$), or —$NO_2$;

$R_{11}$ is selected from H, halogen, —CN, —CHO, —$CF_3$, —$OCF_3$, —OH, —$C_1$-$C_6$ alkyl, $C_1$-$C_6$ alkoxy, $C_1$-$C_6$ thioalkyl, —$NH_2$, —N($C_1$-$C_6$)$_2$, —NH($C_1$-$C_6$), —N—C(O)—($C_1$-$C_6$), —$NO_2$, —N—C(O)—N($C_1$-$C_3$ alkyl)$_2$, —N—C(O)—NH($C_1$-$C_3$alkyl), —N—C(O)—O—($C_1$-$C_3$ alkyl), —$SO_2$—$C_3$-$C_6$ alkyl, —S—$C_3$-$C_6$ cycloalkyl, —S—$CH_2$—$C_3$-$C_6$ cycloalkyl, —$SO_2$-$C_3$-$C_6$ cycloalkyl, —$SO_2$—$CH_2$—$C_3$-$C_6$ cycloalkyl, $C_3$-$C_6$ cycloalkyl, —$CH_2$—$C_3$-$C_6$ cycloalkyl, —O—$C_3$-$C_6$ cycloalkyl, , —O—$CH_2$—$C_3$-$C_6$ cycloalkyl, phenyl, benzyl, benzyloxy, morpholino or other heterocycles such as pyrrolidino, piperidine, piperizine furan, thiophene, imidazole, tetrazole, pyrazine, pyrazolone, pyrazole, imidazole, oxazole or isoxazole, the rings of each of these $R_4$ groups each being optionally substituted by from 1 to 3 substituents selected from the group of H, halogen, —CN, —CHO, —$CF_3$, —OH, —$C_1$-$C_6$ alkyl, $C_1$-$C_6$ alkoxy, —$NH_2$, —N($C_1$-$C_6$)$_2$, —NH($C_1$-$C_6$), —N—C(O)—($C_1$-$C_6$), —$NO_2$, $SO_2$($C_1$-$C_3$ alkyl), —$SO_2NH$($C_1$-$C_3$ alkyl), —$SO_2N$($C_1$-$C_3$ alkyl)$_2$, or $OCF_3$;

$n_1$ is an integer from 1 to 3;

$n_2$ is an integer from 0 to 4;

$X_1$ is selected from a chemical bond, —S—, —O—, —S(O)—, —S(O)$_2$—, —NH—, —NHC(O)—, —C=C—

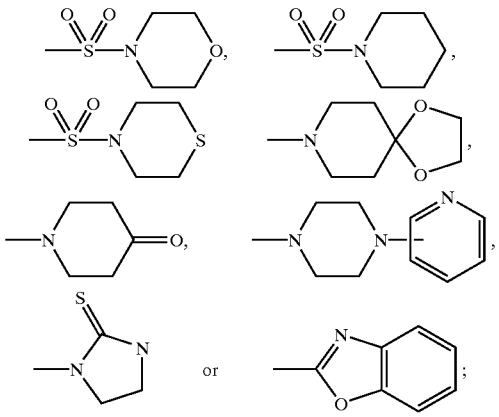

$R_{12}$ is a ring moiety selected from $C_1$-$C_6$ alkyl, $C_1$-$C_6$ fluorinated alkyl, $C_3$-$C_6$ cycloalkyl, tetrahydropyranyl, camphoryl, adamantyl, CN, —N($C_1$-$C_6$ alkyl)$_2$, phenyl, pyridinyl, pyrimidinyl, furyl, thienyl, napthyl, morpholinyl, triazolyl, pyrazolyl, piperidinyl, pyrrolidinyl, imidazolyl, piperizinyl, thiazolidinyl, thiomorpholinyl, tetrazole, indole, benzoxazole, benzofuran, imidazolidine-2-thione, 7,7-dimethyl-bicyclo[2.2.1]heptan-2-one or pyrrolyl groups, each optionally substituted by from 1 to 3, preferably 1 to 2, substituents independently selected from H, halogen, —CN, —CHO, —$CF_3$, —OH, —$C_1$-$C_6$ alkyl, $C_1$-$C_6$ alkoxy, —$NH_2$, —N($C_1$-$C_6$)$_2$, —NH($C_1$-$C_6$), —N—C(O)—($C_1$-$C_6$), —$NO_2$, —$SO_2$($C_1$-$C_3$ alkyl), —$SO_2NH_2$, —$SO_2NH$($C_1$-$C_3$ alkyl), —$SO_2N$($C_1$-$C_3$ alkyl)$_2$, $OCF_3$, —COOH, —$CH_2$—COOH, —$CH_2$—N($C_1$-$C_6$ alkyl), —$CH_2$—N($C_1$-$C_6$ alkyl)$_2$, —$CH_2$—$NH_2$, pyridine or or a pharmaceutically acceptable salt or ester form thereof.

Among the more preferred ester forms of the compounds of formula V wherein $R_9$ is the formula —$(CH_2)_{n4}$—$CO_2H$, are the $C_1$-$C_8$ alkyl esters, including straight, branched or cyclic alkyl groups, or benzyl esters.

The final pharmaceutically useful compounds of formula V, which may be prepared using the intermediate compounds of this invention, inhibit cPLA2 activity which is required for supplying arachidonic acid substrate to cyclooxygenase-1 or -2 and 5-lipoxygenase which in turn initiate the production of prostaglandins and leukotrienes respectively. In addition, $cPLA_2$ activity is essential for producing the lyso-phospholipid that is the precursor to PAF. Thus the final compounds are useful in the treatment and prevention of disease states in which leukotrienes, prostaglandins or PAF are involved. Moreover, in diseases where more than one of these agents plays a role, a $cPLA_2$ inhibitor would be expected to be more efficacious than leukotriene, prostaglandin or PAF receptor antagonists and also more effective than cyclooxygenase or 5-lipoxygenase inhibitors.

Therefore, the compounds of formula V, pharmaceutical compositions containing these compounds and methods of using such compounds described herein are useful in treating and preventing the disorders treated by cyclooxygenase-2, cycloxygenase-1, and 5-lipoxygenase inhibitors and also antagonists of the receptors for PAF, leukotrienes or prostaglandins. Diseases which may be treated include but are not limited to: pulmonary disorders including diseases such as asthma, chronic bronchitis, and related obstructive airway diseases; allergies and allergic reactions such as allergic rhinitis, contact dermatitis, allergic conjunctivitis, and the like; inflammation such as arthritis or inflammatory bowel diseases, skin disorders such as psoriasis, atopic eczema, acne, UV damage, burns and dermatittis; cardiovascular disorders such as atherosclerosis, angina, myocardial ischaemia, hypertension, platelet aggregation, and the like; and renal insufficiency induced by immunological or chemical. The compounds of formula V may also be cytoprotective, preventing damage to the gastrointestinal mucosa by noxious agents. These compounds will also be useful in the treatment of adult respiratory distress syndrome, endotoxin shock and ischeamia induced injury including myocardial or brain injury.

These compounds, compositions and methods will be especially useful in the treatment of arthritic disorders, including but not limited to rheumatoid arthritis, spondyloarthropathies, gouty arthritis, osteoarthritis, systemic lupus erythematosus and juvenile arthritis, and also in the treatment of post- operative inflammation including that following ophthalmic surgery such as cataract surgery or refractive surgery.

The pharmaceutical agents described above can be used as antipyretic agents. They may be utilized in methods of treating pain, particularly the pain associated with inflammation.

Compounds of formula V and pharmaceutically acceptable compositions thereof are useful in the treatment of menstrual cramps, pre-term labor, tendonitis, bursitis, allergic neuritis, cytomegalovirus infection, apoptosis, including HIV-induced apoptosis, lumbago, liver disease including hepatitis. They are also useful in treating gastrointestinal conditions such as inflammatory bowel disease, Crohn's disease, gastritis, irritable bowel syndrome and ulcerative colitis and for the prevention of treatment of cancer such as colorectal cancer. The pharmaceutical compounds and compositions described herein are also useful for the prevention or treatment of benign and malignant tumors/neoplasia including cancers such as colorectal cancer, brain cancer, bone cancer, epithelial cell-derived neoplasia (epithelial carcinoma) such as basal cell carcinoma, adenocarcinoma, gastrointestinal cancer, including lip cancer, mouth cancer, esophogeal cancer, small bowel cancer and stomach cancer, colon cancer, liver cancer, bladder cancer, pancreatic cancer, ovarian cancer, cervical cancer, lung cancer, breast cancer, and skin cancers, such as squamous cell and basal cell cancers, prostate cancer, renal cell carcinoma, and other known cancers that effect epithelial cells throughout the body. Neoplasias for which these compositions are contemplated to be particularly useful are gastrointestinal cancer, Barrett's esophagus, liver cancer, bladder cancer, pancreas cancer, ovarian cancer, prostatic cancer, cervical cancer, lung cancer, breast cancer, and skin cancer, such as squamous cell and basal cell cancers. The compounds and methods can also be used to treat the fibrosis occurring with radiation therapy. Such compositions can be used to treat subjects having adenomatous polyps, including those with familial adenomatous polyposis (FAP). Additionally, such compositions can be used to prevent polyps from forming in patients at risk of FAP. Compounds of this invention are useful in the treatment of cancers because of their anti-angiogenic effects.

The novel intermediate compounds of formula I and the final pharmaceutically useful compounds of formula V may be prepared by various methods which are set forth generally and illustrated specifically in the following synthetic methods and specific examples. The following examples are presented to illustrate certain embodiments of the present invention, but should not be construed as limiting the scope of this invention.

Method A

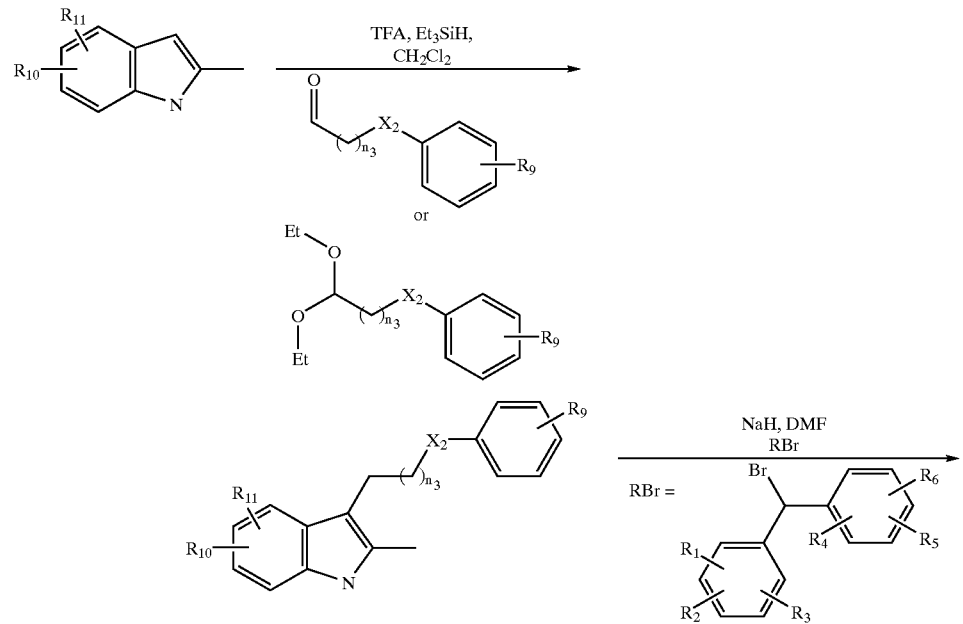

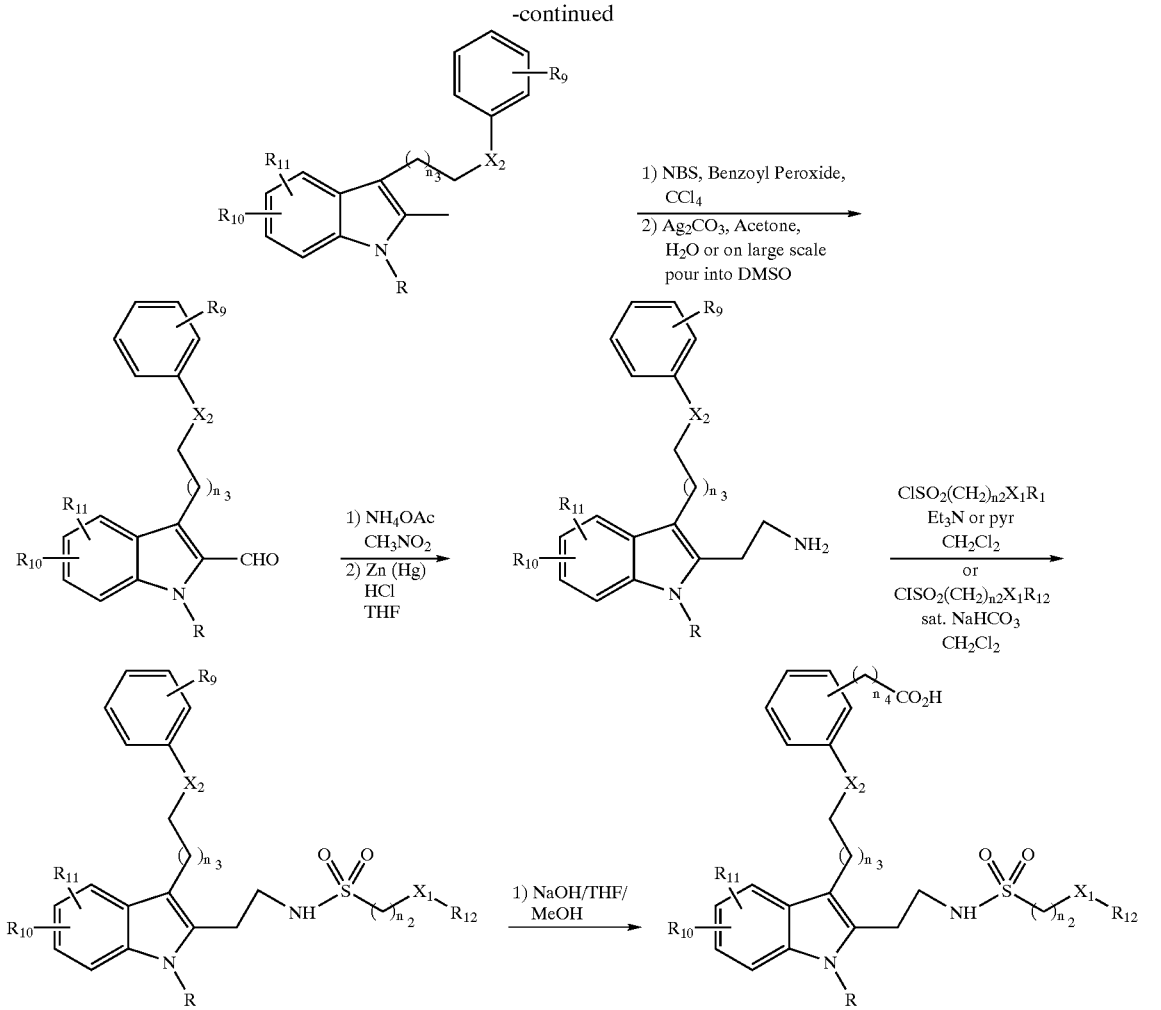

Method A

The initial indole of Method A may be alkylated at the C3 position with aldehydes or the corresponding acetals in the presence of a Lewis or Bronsted acid, such as boron triflouride etherate or triflouroacetic acid. In the synthetic scheme, above, X is as defined herein and Ph refers to the corresponding phenyl ring optionally substituted by $R_7$, $R_8$ and $R_9$. The indole nitrogen may then be alkylated by treatment with a strong base such as sodium bis(trimethylsilyl) amide, n-BuLi, sodium hydride or potassium hydride in a solvent such as DMF, DMSO or THF followed by exposure to the appropriate alkyl halide. The resulting product can be treated with carbon tetrabromide in carbon tetrachloride and a catalytic amount of benzoyl peroxide to effect dibromination of the C2 methyl group. The dibromide can then either be stirred with silver carbonate in acetone water or poured into DMSO and stirred. Both of these procedures generate the aldehyde which is then subjected to the nitro aldol reaction with nitromethane and a catalytic amount of ammonium acetate at reflux. The resulting vinyl nitro intermediate is reduced to the amine upon treatment with zinc mercury amalgam in a mixture of THF and conc. HCL at reflux. This amine can then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.). This method was used in the synthesis of Examples 1–887, 108–112, and 126–128.

Method B

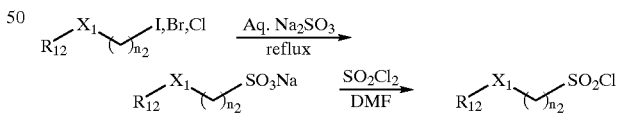

Method B

The initial halide of Method B is refluxed in aqueous sodium sulfite and a suitable cosolvent if necessary, such as alcohol, dioxane etc, for the required amount of time to form the desired sodium sulfonate. This intermediate was treated with thionyl chloride, phosphorous pentachloride or oxalyl chloride, in dichloromethane with a small amount of DMF and stirred for several hours at room temperature until the sulfonyl chloride is formed. The thus formed sulfonyl chloride is then used crude in Method A. This method was used in the synthesis of Examples 1–887, 108–112 and 126–128 when the sulfonyl chloride was not commercially available.

Example 1

4-[2-(1-Benzhydryl-2-{2[(benzylsulfonyl)amino] ethyl}-5-chloro-1H-indol-3-yl)ethoxyl]benzoic acid This synthesis is depicted in Method A Step 1: To 4-hydroxy-benzoic acid methyl ester (1.0 eq) in DMF (0.83 M) was added $K_2CO_3$ (2.0 eq) followed by 2-bromo-1,1-diethoxy-ethane and the reaction mixture was stirred at 110° C. for 2 days. TLC showed a new spot. The reaction mixture was diluted with ethyl acetate, washed with 1N NaOH, water, and brine, dried over sodium sulfate, and solvent was removed to afford desired product in 84% yield. This material was used in the next step without further purification.

Step 2: To the above product (1.0 eq) and 5-chloro-2-methyl indole (1.0 eq) in $CH_2Cl_2$ (0.12 M) was added triethylsilane (3.0 eq) followed by trifluoroacetic acid (3.0 eq). After being stirred overnight at room temperature, added water and trifluroacetic acid (1.0 eq) to the reaction mixture, stirred at room temperature for two days, diluted with $CH_2Cl_2$, washed with 1 N NaOH, water, brine, dried over sodium sulfate. Trituration of the material with $CH_2Cl_2$ and hexanes afforded the C3 alkylated indole in 92% yield Step 3: To the indole from above (1.0 eq) in DMF (0.36 M) at 25° C. was added NaH (1.2 eq, 60% dispersion in oil), and the brown solution was stirred at 0 to –5° C. for 1 h and then compound bromodiphenylmethane was added (1.1 eq), and then the reaction mixture was stirred overnight. It was then quenched with water, diluted with ethyl acetate, washed with water and brine, dried over sodium sulfate and purified by column chromatography to yield 72% of the desired product.

Step 4: To the N-alkylated indole from above (1.0 eq) in $CCl_4$ (0.2 M) was added N-bromosuccinimide (2.0 eq) and a catalytic amount of benzoyl peroxide. The solution was heated to reflux for 3 h, cooled to 25° C., filtered, and the solid was washed with $CCl_4$. The filtrate was concentrated to a foam, which was dried. The foam was dissolved in acetone, and $Ag_2CO_3$ (1.1 eq.) was added followed by water and the reaction mixture was stirred overnight at room temperature. It was filtered and washed with acetone. The filtrate was concentrated to a residue, to which was added water. This mixture was extracted with ethyl acetate, washed with brine, dried over sodium sulfate and then chromatographic purification on the residue gave the desired product in 85% yield. Alternatively the dibromide from the reaction with NBS could be poured into DMSO (10–20% concentration by weight) stirred for 30 minutes at room temperature. When the reaction was deemed complete it was poured into water and the resulting precipitate was isolated by filtration, the cake was washed with water and dried to yield an essentially quantitative yield.

Step 5: To the above aldehyde (1.0 equiv) in $CH_3NO_2$ (0.2 M) was added ammonium acetate (4 equiv) and the resulting mixture was heated to reflux for 4 h. The reaction mixture was then diluted with EtOAc and washed with brine. The aqueous phase was extracted with EtOAc. The combined organic extracts were washed with brine, dried over sodium sulfate, and concentrated until an orange crystalline solid precipitated. The mixture was refrigerated overnight and the nitroolefin (76% yield) was collected by filtration. Evaporation of the solution phase and purification of the residue by column chromatography (gradient elution 100% toluene→1% EtOAc-toluene) afforded an additional amount of the nitroolefin (23% yield).

Step 6: Zinc dust (20 equiv) was suspended in 5% aqueous HCl solution (8 M Zn/5% HCl). To this mixture was added $HgCl_2$ (0.28 equiv). The mixture was shaken for 10 min, the aqueous phase was decanted and replaced with fresh 5% HCl, and again the mixture was shaken for 5 min and the aqueous phase was removed. The zinc-mercury amalgam thus generated was then added to a mixture of the nitroolefin (1.0 equiv) and conc. HCl (80 equiv) in THF (0.04 M nitroolefin/THF). The mixture was maintained at a gentle reflux for 1 h. The formation of product was followed by TLC analysis. The mixture was cooled to room temperature and the solids were removed by filtration through Celite. Conc. $NH_4OH$ was added to the solution phase and the mixture was concentrated on the rotary evaporator. The residue was dissolved in $CH_2Cl_2$ and conc. $NH_4OH$. The aqueous phase was extracted with $CH_2Cl_2$, and the organic phase was washed with brine, dried over sodium sulfate, and concentrated. Purification by column chromatography afforded the desired product (65% yield).

Step 7: To methyl 4-{2-[2-(2-aminoethyl)-1-benzhydryl-5-chloro-1H-indol-3-yl]ethoxy}benzoate (1.0 equiv) and sat. $NaHCO_3$ (0.14 M) in $CH_2Cl_2$ (0.07 M) was added □-toluenesulfonyl chloride (1.0 equiv). After 1 h the mixture was poured into saturated sodium bicarbonate and extracted with $CH_2Cl_2$. The combined organic phase was washed with brine, dried over sodium sulfate and purified by column chromatography (gradient elution using 20% EtOAc-hexanes→50% EtOAc-hexanes) to afford 86% of the desired product.

Step 8: The resulting ester was hydrolyzed by stirring with 1N NaOH (5 equiv) in THF (0.07 M) and enough MeOH to produce a clear solution. The reaction was monitored by TLC (10% MeOH-$CH_2Cl_2$) for the disappearance of starting material. The mixture was heated in a 60 degrees C. oil bath for 2 hour. The mixture was concentrated, diluted with $H_2O$, and acidified to pH 2–4 using 1 M HCl. The aqueous phase was extracted with EtOAc and the organic phase was washed with brine, dried over sodium sulfate, and concentrated to afford the desired product in 92% yield. HRMS calc for $[C_{39}H_{35}ClN_2O_5.S+H]$ 679.2028 found 679.2031.

Example 2

4-[2-(1-Benzhydryl-5-chloro-2-{2-[(isopropylsulfonyl)amino]ethyl}-1H-indol-3-yl) ethoxy]benzoic acid Step 1: This compound was prepared from methyl 4-{2-[2-(2-aminoethyl)-1-benzhydryl-5-chloro-1H-indol-3-yl] ethoxy}benzoate (Step 5, Example 1) and isopropylsulfonyl chloride according to the procedure in Example 1 Step 7 in 55% yield.

Step 2: The ester intermediate was hydrolyzed according to Step 8 Example 1 to afford the title acid in 81% yield. HRMS calc for $[C_{35}H_{35}ClN_2O_5.S+H]$ 631.2028 found 631.2029.

Example 3

4-[2-(1-Benzhydryl-2-{2-[(butylsulfonyl)amino] ethyl}-5-chloro-1H-indol-3-yl)ethoxy]benzoic acid Step 1: This compound was prepared from methyl 4-{2-[2-(2-aminoethyl)-1-benzhydryl-5-chloro-1H-indol-3-yl] ethoxy}benzoate (Step 5, Example 1) and 1-butanesulfonyl chloride according to the procedure in Example 1 Step 7 in 61% yield.

Step 2: The ester intermediate was hydrolyzed according to Step 8 Example 1 to afford the title acid in 90% yield. HRMS calc for $[C_{36}H_{37}ClN_2O_5.S+H]$ 645.2185 found 645.2185.

Example 4

4-{2-[1-Benzhydryl-5-chloro-2-(2{[(1-methyl-1H-imidazol-4-yl)sulfonyl]amino}ethyl)-1H-indol-3-yl]ethoxy}benzoic acid Step 1: To methyl 4-{2-[2-(2-aminoethyl)-1-benzhydryl-5-chloro-1H-indol-3-yl]ethoxy}benzoate (Step 5, Example 1) (1.0 equiv) and Et$_3$N (3.0 equiv) or pyridine (3.0 equiv) in CH$_2$Cl$_2$ (0.05 M) was added 1-methylimidazole-4-sulfonyl chloride (1.2 equiv). The reaction was monitored by TLC (10% MeOH—CH$_2$Cl$_2$) and was heated if necessary. After 30 min the mixture was poured into saturated sodium bicarbonate and extracted with CH$_2$Cl$_2$. The combined organic phase was washed with brine, dried over sodium sulfate and purified by column chromatography to afford 92% of the desired product.

Step 2: The ester intermediate was hydrolyzed according to Step 8 Example 1 to afford the title acid in 89% yield. HRMS calc for [C$_{36}$H$_{33}$ClN$_4$O$_5$.S+H] 669.1933 found 669.1932.

Example 5

4-{2-[1-Benzhydryl-2-(2-{[(5-bromo6-chloro-3-pyridinyl)sulfonyl]amino}ethyl)-5-chloro-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and 3-bromo-2-chloropyridine-5-sulfonyl chloride according to the procedure in Example 1 Step 7 in 74% yield.

Step 2: The ester intermediate was hydrolyzed according to Step 8 Example 1 to afford the title acid in 98% yield. HRMS calc for [C$_{37}$H$_{30}$BrCl$_2$N$_3$O$_5$.S+H] 778.0539 found 778.0544.

Example 6

4-[2-(1-Benzhydryl-5-chloro-2-{2-[({[(1R)-7,7-dimethyl-2-oxobicyclo[2.2.1]hept-1-yl]methyl}sulfonyl)amino]ethyl}-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and (1R)-(−)-10-camphorsulfonyl chloride according to the procedure in Example 1 Step 7 in 77% yield.

Step 2: The ester intermediate was hydrolyzed according to Step 8 Example 1 to afford the title acid in 94% yield. HRMS calc for [C$_{42}$H$_{43}$ClN$_2$O$_6$.S+H] 739.2603 found 739.26.

Example 7

4-(2-(1-Benzhydryl-5-chloro-2-[2-({[(methylsulfonyl)methyl]sulfonyl}amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and (methanesulfonyl)methanesulfonyl chloride according to the procedure in Example 4 Step 1 in 43% yield.

Step 2: The ester intermediate was hydrolyzed according to Example 117 Step 2 to afford the title acid in 95% yield. HRMS calc for [C$_{34}$H$_{33}$ClN$_l$ $_{O7}$.S$_2$+H] 681.1491 found 681.1489.

Example 8

4-(2-{1-Benzhydryl-5-chloro-2-[2-({[(2-(1-naphthyl)ethyl]sulfonyl}amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and 2-(1-naphthyl)ethanesulfonyl chloride according to the procedure Example 1 Step 7 in 60% yield.

Step 2: The ester intermediate was hydrolyzed according to Step 8 Example 1 to afford the title acid in 100% yield. HRMS calc for [C$_{44}$H$_{39}$ClN$_l$ $_{O5}$.S+H] 743.2341 found 743.2338.

Example 9

4-{2-[1-Benzhydryl-5-chloro-2-(2-[({2-nitrobenzyl}-sulfonyl)amino]ethyl}-1H-indol-3-yl)ethoxy]benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and 2-nitro-□-toluenesulfonyl chloride according to the procedure in Example 1 Step 7 in 82% yield.

Step 2: The ester intermediate was hydrolyzed according to Step 8 Example 1 to afford the title acid in 85% yield. HRMS calc for [C$_{39}$H$_{34}$ClN$_3$O$_7$.S+H] 724.1879 found 724.1877.

Example 10

4-{2-[1-Benzhydryl-5-chloro-2-(2-{[(3,4-dichlorobenzyl)sulfonyl]amino}-ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and [(3,4-dichlorophenyl)-methyl]sulfonyl chloride according to the procedure in Example 1 Step 7 in 82% yield.

Step 2: The ester intermediate was hydrolyzed according to Step 8 Example 1 to afford the title acid in 86% yield. HRMS calc for [C$_{39}$H$_{33}$Cl$_3$N$_2$O$_5$.S+H] 747.1249 found 747.1249.

Example 11

4-{2-[1-Benzhydryl-5-chloro-2-(2-{[(3,5-dichlorobenzyl)sulfonyl]amino}-ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and [(3,5-dichlorophenyl)-methyl]sulfonyl chloride according to the procedure in Example 1 Step 7 in 100% yield.

Step 2: The ester intermediate was hydrolyzed according to Step 8 Example 1 to afford the title acid in 98% yield. HRMS calc for [C$_{39}$H$_{33}$Cl$_3$N$_2$O$_5$.S+H] 747.1249 found 747.1249.

Example 12

4-(2-{1-Benzhydryl-5chloro-2-(2-({[(3-(trifluoromethyl)benzyl]sulfonyl}-amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]

ethoxy}benzoate (Step 5, Example 1) and [[3-(trifluoromethyl)-phenyl]methyl]sulfonyl chloride according to the procedure in Example 1 Step 7 in 74% yield.

Step 2: The ester intermediate was hydrolyzed according to Step 8 Example 1 to afford the title acid in 86% yield. HRMS calc for $[C_{40}H_{34}ClF_3N_2O_5S+H]$ 747.1902 found 747.1904.

Example 13

4-(2-{1-Benzhydryl-5-chloro-2-(2-({[(4-(trifluoromethyl)benzyl]sulfonyl}-amino)ethyl]-1H-indol-3-yl}ethoxy)benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and [[4-(trifluoromethyl)phenyl]methyl]sulfonyl chloride according to the procedure in Example 1 Step 7 in 77% yield.

Step 2: The ester intermediate was hydrolyzed according to Step 8 Example 1 to afford the title acid in 83% yield. HRMS calc for $[C_{40}H_{34}ClF_3N_2O_5S+H]$ 747.1902 found 747.1901.

Example 14

4-{2-[1-Benzhydryl-5-chloro-2-(2-{[(4-fluorobenzyl)sulfonyl]amino}-ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and [(4-fluorophenyl)methyl]sulfonyl chloride according to the procedure in Example 1 Step 7 Step 1 in 86% yield.

Step 2: The ester intermediate was hydrolyzed according to Step 8 Example 1 to afford the title acid in 94% yield. HRMS calc for $[C_{39}H_{34}ClFN_2O_5S+H]$ 697.1934 found 697.1938.

Example 15

4-{2-[1-Benzhydryl-5-chloro-2-(2-{[(4-chlorobenzyl)sulfonyl]amino}-ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and [(4-chlorophenyl-)methyl]sulfonyl chloride according to the procedure in Example 1 Step 7 in 73% yield.

Step 2: The ester intermediate was hydrolyzed according to Step 8 Example 1 to afford the title acid in 99% yield. HRMS calc for $[C_{39}H_{34}Cl_2N_2O_5S+H]$ 713.1638 found 713.1643.

Example 16

2-(2{[(2-Aminobenzyl)sulfonyl]amino}ethyl)-4-(2-[1-benzhydryl-5-chloro-1H-indol-3-yl)ethoxy}benzoic acid Step 1: To methyl 4-{2-[1-benzhydryl-5-chloro-2-{2-[2-nitrobenzyl]benzyl}-sulfonyl)amino]ethyl}-1H-indol-3-yl)ethoxy]benzoate, Example 9, step 1, (1.0 equiv) in $CH_2Cl_2$ (0.014 M) was added a mixture of tin(II) chloride dihydrate (3.0 equiv) dissolved in concentrated HCl. After 16 h the mixture was basified (pH 10) with 3 N NaOH and extracted with $CH_2Cl_2$. The combined organic phase was washed with brine, dried over sodium sulfate and purified by column chromatography (gradient elution using 20% EtOAc-hexanes→50% EtOAc-hexanes) to afford 83% of the desired product.

Step 2: The ester intermediate was hydrolyzed according to Step 8 Example 1 to afford the title acid in 83% yield. HRMS calc for $[C_{39}H_{36}ClN_3O_5S+H]$ 694.2137 found 694.2136.

Example 17

4-{2-[1-Benzhydryl-5-chloro-2-(2-{[(dimethylamino)sulfonyl]amino}ethyl)-1H-indol-3-yl]ethoxy}benzoic acid Step 1: This compound was prepared from methyl 4-{2-[2-(2-aminoethyl)-1-benzhydryl-5-chloro-1H-indol-3-yl]ethoxy}benzoate (Step 5, Example 1) and dimethylsulfamoyl chloride according to the procedure in Example 1 Step 7 in 49% yield.

Step 2:. The ester intermediate was hydrolyzed according to Step 8 Example 1to afford the title acid in 95% yield. HRMS calc for $[C_{34}H_{34}ClN_3O_5S+H]$ 632.1981 found 632.1984.

Example 18

4-{2-[1-Benzhydryl-5-chloro-2-(2{[(3,4-difluorobenzyl)sulfonyl]amino}-ethyl)-1H-indol-3-yl]ethoxy}benzoic acid Step 1: To 3,4-difluorobenzyl bromide (1.0 equiv) in $H_2O$ (0.74 M) was added sodium sulfite (1.1 equiv). The mixture was heated to reflux for 16 hours then cooled to room temperature. The white precipitate was filtered and dried to afford 95% of the sodium sulfonate intermediate.

Step 2:. To 3,4-difluorobenzyl sodium sulfonate (7.6 equiv) in $CH_2Cl_2$ (0.76 M) was added DMF (5.6 equiv) and $SOCl_2$ (30 equiv). After 1 h the mixture was concentrated and azeotroped with toluene. The residue was suspended in $CH_2Cl_2$ (0.38 M) and methyl 4-{2-[2-(2-aminoethyl)-1-benzhydryl-5-chloro-1H-indol-3-yl]ethoxy}benzoate (Step 5, Example 1) (1.0 equiv) and sat. $NaHCO_3$ (0.76 M) were added. After 1 h the mixture was poured into $H_2O$ and extracted with $CH_2Cl_2$. The combined organic phase was washed with brine, dried over sodium sulfate and purified by column chromatography (gradient elution using 20% EtOAc-hexanes→40% EtOAc-hexanes) to afford 94% of the methyl ester intermediate.

Step 3: The methyl ester was hydrolyzed according to Step 8 Example 1 to afford the title acid in 93% yield. HRMS calc for $[C_{39}H_{33}ClF_2N_2O_5S+H]$ 715.184 found 715.1843.

Example 19

4-{2-[1-benzhydryl-5-chloro-2-(2{[(2-naphthylmethyl)sulfonyl]amino}ethyl)-1H-indol-3-yl]ethoxy}benzoic acid Step 1: The sulfonyl chloride intermediate was prepared from 2-(bromomethyl)naphthalene according to the procedure in Example 18 Step 1–2 in 34% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 58% yield.

Step 2: The ester intermediate was hydrolyzed according to Step 8 Example 1 to afford the title acid in 74% yield. HRMS calc for [$C_{43}H_{37}ClN_2O_5S$+H] 729.2185 found 729.2189.

Example 20

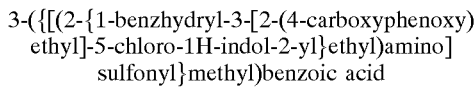
3-({[(2-{1-benzhydryl-3-[2-(4-carboxyphenoxy) ethyl]-5-chloro-1H-indol-2-yl}ethyl)amino] sulfonyl}methyl)benzoic acid Step 1: The sulfonyl chloride intermediate was prepared from methyl 3-(bromomethyl)benzoate according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 23% yield.

Step 2: The ester intermediate was hydrolyzed according to Step 8 Example 1 to afford the title diacid in 93% yield. HRMS calc for [$C_{40}H_{35}ClN_2O_7S$+H] 723.1926 found 723.1932

Example 21

4-(2-{1-benzhydryl-5-chloro-2-[2-({[(E)-2-phenylethenyl]sulfonyl}amino)ethyl'1H-indol-3-yl}ethoxy)benzoic acid Step 1: To the methyl 4-{2-[2-(2-aminoethyl)-1-benzhydryl-5-chloro-1H-indol-3-yl]ethoxy}benzoate (Step 5, Example 1) was added trans-□-styrenesulfonyl chloride according to the procedure in Example 1 Step 7 to generate the product in 66% yield.

Step 2—The ester intermediate was hydrolyzed according to Step 8 Example 1 to afford the title acid in 98% yield. HRMS calc for [$C_{40}H_{35}ClN_2O_5S$+H] 691.2028 found 691.2034.

Example 22

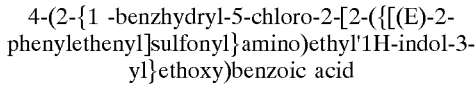
4-{2-[1-benzhydryl-5-chloro-2-(2-{[(trifluoromethyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 5, Example 1)was added trifluoromethylsulfonyl chloride according to the procedure in Example 1 Step 7 to generate the product in 49% yield.

Step2—The ester intermediate was hydrolyzed according to Step 8 Example 1 to afford the title acid in 100% yield. HRMS calc for [$C_{33}H_{28}ClF_3N_2O_5S$+H] 657.1432 found 657.1435.

Example 23

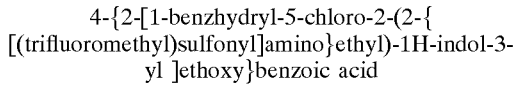
4-[2-(1-benzhydryl-5-chloro-2-{2-[(cyclopropylsulfonyl)amino]ethyl}-1H-indol-3-yl) ethoxy]benzoic acid Step 1: To the methyl 4-{2-[2-(2-aminoethyl)-1-benzhydryl-5-chloro-1H-indol-3-yl]ethoxy}benzoate (Step 5, Example 1)was added cyclopropanesulfonyl chloride according to the procedure in Example 1 Step 7 to generate the product in 75% yield.

Step2—The ester intermediate was hydrolyzed according to Step 8 Example 1 to afford the title acid in 84% yield. HRMS calc for [$C_{35}H_{33}ClN_2O_5S$+H] 629.1872 found 629.1874.

Example 24

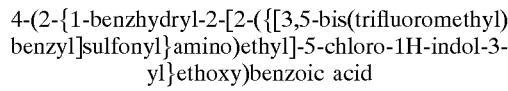
4-(2-{1-benzhydryl-2-[2-({[3,5-bis(trifluoromethyl) benzyl]sulfonyl}amino)ethyl]-5-chloro-1H-indol-3-yl}ethoxy)benzoic acid Step 1: To the methyl 4-{2-[2-(2-aminoethyl)-1-benzhydryl-5-chloro-1H-indol-3-yl]ethoxy}benzoate (Step 5, Example 1)was added 3,5-bis(trifluoromethyl) benzylsulfonyl according to the procedure in Example 1 Step 7 to generate the product in 79% yield.

Step2—The ester intermediate was hydrolyzed according to Step 8 Example 1 to afford the title acid in 81% yield. HRMS calc for [$C_{41}H_{33}ClF_6N_2O_5S$+H] 815.1776 found 815.1776.

Example 25

2-{[(2-{1-benzhydryl-3-[2-(4-carboxyphenoxy) ethyl]-5-chloro-1H-indol-2-yl}ethyl)amino] sulfonyl}benzoic acid Step 1: To the methyl 4-{2-[2-(2-aminoethyl)-1-benzhydryl-5-chloro-1H-indol-3-yl]ethoxy}benzoate (Step 5, Example 1)was added methyl (2-chlorosulfonyl)benzoate according to the procedure in Example 1 Step 7 to generate the product in 100% yield.

Step2—The ester intermediate was hydrolyzed according to Step 8 Example 1 to afford the title acid in 61% yield. HRMS calc for [$C_{39}H_{33}ClN_2O_7S$+H] 709.177 found 709.1772.

Example 26

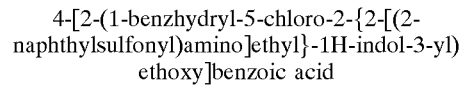
4-[2-(1-benzhydryl-5-chloro-2-{2-[(2-naphthylsulfonyl)amino]ethyl}-1H-indol-3-yl) ethoxy]benzoic acid Step 1: To the methyl 4-{2-[2-(2-aminoethyl)-1-benzhydryl-5-chloro-1H-indol-3-yl]ethoxy}benzoate (Step 5, Example 1)was added 2-naphthalenesulfonyl chloride according to the procedure in Example 1 Step 7 to generate the product in 53% yield.

Step2—The ester intermediate was hydrolyzed according to Step 8 Example 1 to afford the title acid in 100% yield. HRMS calc for [$C_{42}H_{35}ClN_2O_5S$+H] 715.2028 found 715.2034.

Example 27

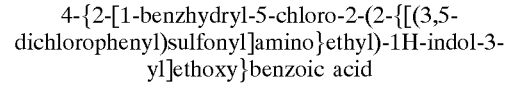
4-{2-[1-benzhydryl-5-chloro-2-(2-{[(3,5-dichlorophenyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 5, Example 1)was added 3,5-dichlorobenzenesulfonyl chloride according to the procedure in Example 1 Step 7 to generate the product in 60% yield.

Step2—The ester intermediate was hydrolyzed according to Step 8 Example 1 to afford the title acid in 88% yield. HRMS calc for [$C_{38}H_{31}Cl_3N_2O_5S$+H] 733.1092 found 733.1096.

Example 28

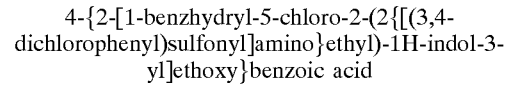
4-{2-[1-benzhydryl-5-chloro-2-(2{[(3,4-dichlorophenyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 5, Example 1)was added 3,4-dichlorobenzenesulfonyl chloride according to the procedure in Example 1 Step 7 to generate the product in 60% yield.

Step2—The ester intermediate was hydrolyzed according to Step 8 Example 1 to afford the title acid in 80% yield. HRMS calc for $[C_{38}H_{31}Cl_3N_2O_5S+H]$ 733.1092 found 733.1094.

Example 29

4-{2-[1-benzhydryl-5-chloro-2-(2-{[(2,3-dichlorobenzyl)sulfonyl]amino}ethyl)-1H indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 5, Example 1)was added (2,3-dichlorophenyl)-methyl] sulfonyl chloride according to the procedure in Example 1 Step 7 to generate the product in 50% yield.

Step2—The resulting ester was hydrolyzed by stirring with KOH (67 mg, 5 equiv.) in THF (5 mL) MeOH (5 mL) and $H_2O$ (2 mL). The reaction was monitored by TLC (10% MeOH—$CH_2Cl_2$) for the disappearance of starting material. The mixture was stirred overnight at room temperature and then concentrated, diluted with $H_2O$, and acidified to pH 2–4 using 1 M HCl. The aqueous phase was extracted with EtOAc and the organic phase was washed with brine, dried over sodium sulfate, and concentrated to afford the desired product in 98% yield. HRMS calc for $[C_{39}H_{33}Cl_3N_2O_5S+H]$ 747.1249 found 747.1254.

Example 30

4-{2-[1-benzhydryl-5-chloro-2-(2-{[(2,4-dichlorobenzyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 5, Example 1)was added (2,4-dichlorophenyl)-methyl] sulfonyl chloride according to the procedure in Example 1 Step 7 to generate the product in 98% yield.

Step2—The ester intermediate was hydrolyzed according to Step 2 Example 29 to afford the title acid in 90% yield. HRMS calc for $[C_{39}H_{33}Cl_3N_2O_5S+H]$ 747.1249 found 747.1255.

Example 31

4-{2-[1-benzhydryl-5-chloro-2-(2{[(2,4-dichlorobenzyl)sulfonyl]amino}ethyl)-1H indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 5, Example 1) was added (2-chlorophenyl)-methyl]sulfonyl chloride according to the procedure in Example 1 Step 7 to generate the product in 86% yield.

Step2—The ester intermediate was hydrolyzed according to Step 2 Example 29 to afford the title acid in 90% yield. HRMS calc for $[C_{39}H_{34}Cl_2N_2O_5S+H]$ 713.1638 found 713.1644.

Example 32

4-{2-[1-benzhydryl-5-chloro-2-(2-{[(4-chloro-2-nitrobenzyl)sulfonyl]amino}ethyl)-1H-indol-3-yl] ethoxy}benzoic acid Step 1: To the methyl 4-{2-[2-(2-aminoethyl)-1-benzhydryl-5-chloro-1H-indol-3-yl]ethoxy}benzoate (Step 5, Example 1)was added [(4-chloro-2-nitro)-methyl] sulfonyl chloride according to the procedure in Example 1 Step 7 to generate the product in 74% yield.

Step2—The ester intermediate was hydrolyzed according to Step 2 Example 29 to afford the title acid in 90% yield. HRMS calc for $[C_{39}H_{33}Cl_2N_3O_7S+H]$ 758.1489 found 758.1494.

Method I

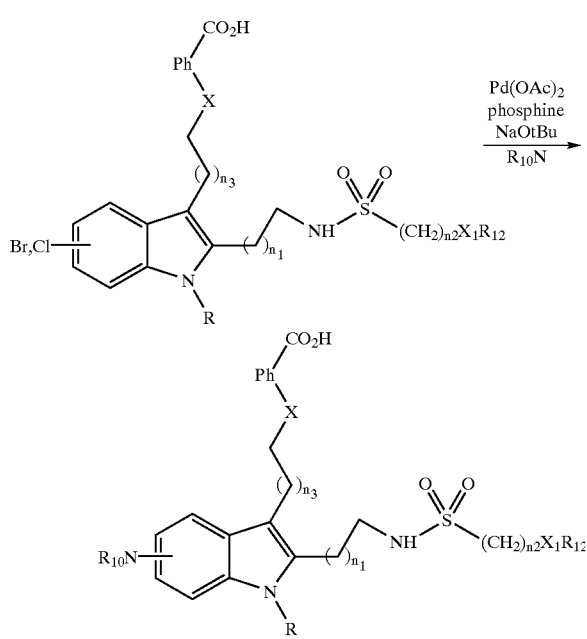

The acid resulting from Method A, or any subsequent method could be used as a subtrate for palladium catalyzed amination reaction using a base, an amine, a phosphine ligand and palldium reagent.

Example 33

4-[2-(1-benzhydryl-2-{2-[(benzylsulfonyl)amino] ethyl}-5-morpholin-4-yl-1H-indol-'3-yl)ethoxy] benzoic acid Step 1—A flask was charged with tris (dibenzylideneacetone)dipalladium(0) (0.01 eq.), 2-(di-t-butylphosphino)biphenyl (0.04 eq.), sodium t-butoxide (2.4 eq.) and the acid from step 8 (1.0 eq.). 1.5 ml toluene (1.0 M) was added to the flask followed by morpholine (1.2 eq.) The reaction was heated to reflux for five hours. The reaction mixture was partitioned between 5% hydrochloric acid and dietheyl ether. The organic layer was washed with distilled water, followed by brine, dried over sodium sulfate and concentrated. The product was purified by preparatory LC-MS to afford 7.8% of the desired product. HRMS calc for $[C_{43}H_{43}N_3O_6S+H]$ 730.2945 found 730.2945.

Example 34

4-{2-[1-Benzhydryl-5-chloro-2-(2-{[(2-cyanobenzyl)sulfonyl]amino}ethyl)-1H-indol-3-yl] ethoxy}benzoic acid Step 1: (2-Cyano-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester and (2-cyano-phenyl)

methanesulfonyl chloride according to Example 1 Step 7 as a white solid in 72% yield.

Step3—The ester intermediate was hydrolyzed according to Step 8 Example to afford the title acid in 74% yield. MS (ES) m/z (M−1) 702.0;HRMS Calcd. for $C_{40}H_{35}ClN_3O_5S$ (M+1): 704.1980. Found: 704.1984. Anal. Calcd. for $C_{40}H_{34}ClN_3O_5S$: C, 68.22;H, 4.87; N, 5.97. Found: C, 67.92;H, 5.11; N, 5.54.

Example 35

4-{2-[1-Benzhydryl-5-chloro-2-(2-{[(2-cyanobenzyl)sulfonyl]amino}ethyl)-1H-indol-3-yl] ethoxy)benzoic acid Step 1: The sulfonyl chloride intermediate was prepared from 3,5-difluorobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 78% yield.

Step 2: The ester intermediate was hydrolyzed according to Step 8 Example 1 to afford the title diacid in 83% yield. HRMS calc for $[C_{39}H_{33}ClF_2N_2O_5S+H]$ 715.184 found 715.1842.

Example 36

4-{2-[1-Benzhydryl-5-chloro-2-(2-{[(3-cyanobenzyl)sulfonyl]amino}ethyl)-1H-indol-3-yl] ethoxy}benzoic acid Step 1: (3-Cyano-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy)benzoic acid methyl ester and (2-cyano-phenyl) methanesulfonyl chloride according to Example 1 Step 7.

Step3—The ester intermediate was hydrolyzed according to Step 8 Example 1 to afford the title acid in 81% yield. MS (ES) m/z (M−1) 702.1;HRMS Calcd. for $C_{40}H_{33}ClN_3O_5S$ (M-1):702.1834. Found: 702.1833. Anal. Calcd. for $C_{40}H_{34}ClN_3O_5S.0.8H_2O$: C, 67.00;H, 5.00; N, 5.86. Found: C, 67.22;H. 5.19; N, 5.44.

Example 37

4-{2-[1-Benzhydryl-5-chloro-2-(2-{[(4-cyanobenzyl)sulfonyl]amino}ethyl)-1H-indol-3-yl] ethoxy}benzoic acid Step 1(4-Cyano-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester and (2-cyano-phenyl) methanesulfonyl chloride according to Example 1 Step 7.

Step3—The ester intermediate was hydrolyzed according to Step 8 Example 1 to afford the title acid in 77% yield. MS (ES) m/z (M−1) 702.1;HRMS Calcd. for $C_{40}H_{35}ClN_3O_5S$ (M+1): 704.1980. Found: 704.1981. Anal. Calcd. for $C_{40}H_{34}ClN_3O_5S$: C, 68.22;H, 4.87; N, 5.97. Found: C, 68.09;H, 4.97; N, 5.73.

Example 38

4-(2-{1-Benzhydryl-5-chloro-2-[2-({[4-(1piperidinylsulfonyl)benzyl]sulfonyl}amino)ethyl]-1H-indol-3-yl}ethoxy)benzoic acid Step 1: [4-(Piperidine-1-sulfonyl)-phenyl]-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}benzoic acid methyl ester and (2-cyano-phenyl) methanesulfonyl chloride according to Example 1 Step 7.

Step3—The ester intermediate was hydrolyzed according to Step 8 Example 1 to afford the title acid in 73% yield. MS (ES) m/z (M−1) 824.2;HRMS Calcd. for $C_{44}H_{43}ClN_3O_7S_2$ (M-1):824.2236. Found: 824.2246. Anal. Calcd. for $C_{44}H_{44}ClN_3O_7S_2.0.5H_2O$: C, 63.25;H, 5.43; N, 5.03. Found: C, 62.85;H, 5.64; N, 4.64.

Example 39

4-(2-{2-[2-({[4-(Aminosulfonyl)benzyl] sulfonyl}amino)ethyl]-1-benzhydryl-5-chloro-1H-indol-3-yl}ethoxy)benzoic acid Step 1: (4-Sulfamoyl-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy)-benzoic acid methyl ester and (2-cyano-phenyl) methanesulfonyl chloride according to Example 1 Step 7.

Step3—The ester intermediate was hydrolyzed according to Step 8 Example 1 to afford the title acid in 69% yield. MS (ES) m/z (M−1) 755.9;HRMS Calcd. for $C_{39}H_{35}ClN_3O_7S_2$ (M-1): 756.1613. Found: 756.1612. Anal. Calcd. for $C_{39}H_{36}ClN_3O_7S_2$: C, 61.77;H, 4.79; N, 5.54. Found: C, 61.93;H, 5.12; N, 5.19.

Example 40

4-(2-{1-Benzhydryl-5-chloro-2-[2-(4-methanesulfonyl-phenylmethanesulfonylamino)-ethyl]-1H-indol-3-yl}-ethoxy)-benzoic acid Step 1: ((4-Methanesulfonyl-phenyl)-methanesulfonyl chloride was prepared according to Example 18 Step 1–2 (crude yield 100%).

Step 2: The title compound was prepared from 4-{2-[2-(2-amino-ethyl)-1-benzhydryl-5-chloro-1H-indol-3-yl]-ethoxy}-benzoic acid methyl ester and (2-cyano-phenyl) methanesulfonyl chloride according to Example 1 Step 7.

Step3—The ester intermediate was hydrolyzed according to Step 8 Example 1 to afford the title acid in 75% yield. MS (ES) m/z (M−1) 755.0;HRMS Calcd. for $C_{40}H_{38}ClN_2O_7S_2$ (M+1): 757.1804. Found: 757.1804. Anal. Calcd. for $C_{40}H_{37}ClN_2O_7S_2H_2O$: C, 61.96;H, 5.07; N, 3.61. Found: C, 61.82;H, 5.10; N, 3.48.

Example 41

4-(2-{1-Benzhydryl-5-chloro-2-[2-(4-diethylsulfamoyl-phenylmethanesulfonylamino) -ethyl]-1H-indol-3-yl}-ethoxy)-benzoic acid Step 1: (4-Diethylsulfamoyl-phenyl)-methanesulfonyl chloride was prepared according to Example 18 Step 1–2 (crude yield 100%).

Step 2: The title compound was prepared from 4-2-[2-(2-amino-ethyl)-1-benzhydryl-5-chloro-1H-indol-3-yl]-ethoxy}-benzoic acid methyl ester and (2-cyano-phenyl)
methanesulfonyl chloride according to Example 1 Step 7.

Step3—The ester intermediate was hydrolyzed according to Step 8 Example 1 to afford the title acid in 66% yield. MS (ES) m/z (M−1) 812.1;HRMS Calcd. for $C_{43}H_{45}ClN_3O_7S_2$ (M+1): 814.2382. Found: 814.2385. Anal. Calcd. for $C_{43}H_{44}ClN_3O_7S_2.0.3H_2O$: C, 62.99;H, 5.48; N. 5.14. Found: C, 62.91;H, 5.67; N, 4.79.

Example 42

4-{3-[1-Benzhydryl-5-chloro-2-(2-phenylmethanesulfonylamino-ethyl)-1H-indol-3-yl]-propyl)-benzoic acid Step 1: A mixture of methyl-4-iodobenzoate (5.3 g, 20.2 mmol), allyl alcohol (1.78 g, 30.3 mmol), $NaHCO_3$ (4.249, 50.5 mmol), $Pd(OAc)_2$ (0.14 g,0.60 mmol), $(n-Bu)_4NBr$ (6.55 g, 20.2 mmol) and 4-A molecular Sieves (4.1 g) in anhydrous DMF (69 mL) was stirred at room temperature for 4 days. The reaction mixture was filtered through celite and the filtrate poured onto water and extracted with EtOAc. Organic layer was washed with brine, dried ($Na_2SO_4$), and concentrated under vaccum. Flash chromatography (silica gel, 10–20% EtOAc-hexanes) gave 2.11 g (85% based on the recovered starting material) of the desired 4-(3-Oxo-propyl)-benzoic acid methyl ester as a clear oil.

Step 2: To a solution of 5-chloro-2-methylindole (0.86 g, 5.2 mmol) and 4-(3-Oxo-propyl)-benzoic acid methyl ester (1.0 g, 5.2 mmol) in methylene chloride (50 mL), was added TFA (1.78 g, 15.6 mmol), followed by triethylsilane (1.81 g, 15.6 mmol). The reaction mixture was stirred overnight, quenched with sat. $NaHCO_3$ solution (50 mL), and the organic layer was washed with sat. $NaHCO_3$ solution, water, brine, and dried ($Na_2SO_4$). Solvent was removed under reduced pressure, and the residue was purified by flash column chromatography with 10–20% EtOAc/hexanes to yield the desired product in 94% (1.67 g) yield.

Step 3: To a solution of the product from step 2 (1.66 g, 4.86 mmol) in DMF (20 mL) was added NaH (60% in mineral oil,0.24 g, 5.83 mmol) under $N_2$ atmosphere. The mixture was stirred for 1 h at room temperature, followed by the dropwise addition of benzhydryl bromide (1.8 g, 7.29 mmol) in DMF (5 mL). This reaction mixture was stirred overnight at room temperature. Water (500 mL) was added to reaction mixture, it was extracted with EtOAc, washed with brine, dried ($Na_2SO_4$), and concentrated under reduced pressure to a brown syrup, which was purified by silica-gel chromatography using 10% EtOAc/hexanes as eluent to isolate 4 as, a white solid in 59% (1.47 g) yield.

Step 4: The product from above (1.46 g, 2.87 mmol) was dissolved in $CCl_4$ (14.5 mL), followed by the addition of NBS (1.02 g, 5.73 mmol) and benzoyl peroxide (2 mg). The reaction mixture was heated to reflux for 1 h (until all the starting material disappeared). This mixture was cooled to room temperature, filtered and the solid was washed with $CCl_4$. The filtrate was evaporated to a brown residue, which was dissolved in acetone (40 mL) and water (4 mL), was added $Ag_2CO_3$ (1.75 g, 3.16 mmol) was then added to this solution and after being stirred overnight at room temperature, it was filtered through celite, the solvent was evaporated under reduced pressure, and water was added to the residue. It was extracted with EtOAc, washed with brine, dried ($Na_2SO_4$), and evaporated to a syrup, which was purified by 10% EtOAc/hexanes to isolate the 2-formyl indole (1.13 g) in 75% yield. Alternatively the dibromide from the reaction with NBS could be poured into DMSO (10–20% concentration by weight) and stirred for 30 minutes at room temperature. When the reaction was deemed complete it was poured into water and the resulting precipitate was isolated by filtration, the cake was washed with water and dried to yield an essentially quantitative yield.

Step 5: To a solution of the 2 formyl indo/w from above (0.52 g, 1 mmol) in $CH_3NO_2$ (6.2 mL) was added $NH_4OAC$ (0.077 g, 1 mmol), the mixture was heated to reflux for 1 h, $NH_4OAC$ (0.077 g, 1 mmol) was then added, heating at reflux was continued for an additional 1 h, $NH_4OAc$ (0.077 g, 1 mmol) was added again and the heating continued for further 1 h. The reaction mixture was allowed to attain room temperature, EtOAc (50 mL) was added, followed by the addition of 100 mL water. The aqueous layer was extracted with EtOAc, and the combined organic layers were washed with brine, dried ($Na_2SO_4$), and evaporated to a yellow foam, which was subjected to chromatographic purification using 10% EtOAc/hexanes as an eluent to yield 6 as a yellow foam in 68% yield (0.38 g).

Step 6 : Zn(Hg) was made by adding $HgCl_2$ (3.4 g, 7.2 mmol) to a mixture of Zn-dust (34.68 g, 530.35 mmol) and 5% HCl (38 mL) in a 100 mL beaker, this mixture was stirred vigorously for 10 min. Aqueous phase was decanted and added 38 mL of 5% HCl again and the mixture was stirred for 10 min. Aqueous phase was decanted. This solid was added to the vinyl nitro compound 6 (15 g, 26.57 mmol) in THF (660 mL) and conc. HCl (64.5 mL). This mixture was stirred at room temperature for 1 h, then at reflux for 15 min. The reaction mixture was cooled to room temperature and filtered through celite. Aq. $NH_4OH$ solution (200 mL) was added to the filtrate, stirred for 15 min and THF was removed under reduced pressure. The aqueous layer was extracted with $CH_2Cl_2$, combined organic layer was washed with brine, dried (Na2SO4) and concentrated to a brown foam, which was purified by column chromatography by eluting the column with $CHCl_3$ in the beginning to remove non-polar impurities then with 2% $MeOH/CHCl_3$ to isolate the desired amine in 46% yield (6.1 g)

Step 7: To the amine(1.0 equiv.) and sat. $NaHCO_3$ (0.14 M) in $CH_2Cl_2$ (0.07 M) was added □-toluenesulfonyl chloride (1.0 equiv.). After 1 h the mixture was poured into saturated sodium bicarbonate and extracted with $CH_2Cl_2$. The combined organic phase was washed with brine, dried over sodium sulfate and purified by column chromatography to afford 84% of the desired product.

Step 8: The resulting ester was hydrolyzed by stirring with 1N NaOH (5 equiv.) in THF (0.07 M) and enough MeOH to produce a clear solution. The reaction was monitored by TLC (10% MeOH-$CH_2Cl_2$) for the disappearance of starting material. The mixture was stirred overnight at room temperature and then. concentrated, diluted with $H_2O$, and acidified to pH 24 using 1 M HCl. The aqueous phase was extracted with EtOAc and the organic phase was washed with brine, dried over sodium sulfate, and concentrated to afford the desired product in 100% yield. HRMS calc for $[C_{40}H_{37}ClN_2O_4S+H]$ 677.2235 found 677.224.

Example 43

4-{3-[1-benzhydryl-5-chloro-2-(2-{[(3,5-dichlorobenzyl)sulfonyl]amino}ethyl)-1H-indol-3-yl]propyl}benzoic acid Step 1: This compound was prepared from the intermediate in Example 42 step 6 and (3,5-dichlorophenyl)-methyl]

sulfonyl chloride according to the procedure in Example 43 Step 7 which yielded 98% of the desired product.

Step 2: The ester intermediate was hydrolyzed according to Step 8 Example 43 to afford the title acid in 100% yield. HRMS calc for $[C_{40}H_{35}Cl_3N_2O_4S+H]$ 745.1456 found 745.1458.

Example 44

4-{3-[1-benzhydryl-5-chloro-2-(2-{[(3,4-dichlorobenzyl)sulfonyl]amino}ethyl)-1H-indol-3-yl]propyl}benzoic acid Step 1: This compound was prepared from the intermediate in Example 42 step 6 and (3,4-dichlorophenyl)-methyl] sulfonyl chloride according to the procedure in Example 43 Step 7 which yielded 96% of the desired product.

Step 2: The ester intermediate was hydrolyzed according to Step 8 Example 43 to afford the title acid in 98% yield. HRMS calc for $[C_{40}H_{35}Cl_3N_2O_4S+H]$ 745.1456 found 745.1458.

Example 45

4-[2-(1-benzhydryl-5-chloro-2-(2-[(methylsulfonyl)amino]ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 5, Example 1)was added methanesulfonyl chloride according to the procedure in Example 4 Step 1 to generate the product in 92% yield.

Step 2: The ester intermediate was hydrolyzed according to Step 8 Example 1 to afford the title acid in 100% yield. HRMS calc for $[C_{33}H_{31}ClN_2O_5S+H]$ 603.1715 found 603.1717.

Example 46

4-[2-(1-benzhydryl-5-chloro-2-{2-[(phenylsulfonyl)amino]ethyl}-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 5, Example 1)was added benzenesulfonyl chloride according to the procedure in Example 4 Step 1 to generate the product in 90% yield.

Step 2: The ester intermediate was hydrolyzed according to Step 8 Example 1 to afford the title acid in 90% yield. HRMS calc for $[C_{38}H_{33}ClN_2O_5S+H]$ 665.1872 found 665.1869

Example 47

4-(2-{1-benzhydryl-5-chloro-2-[2-({[3-(trifluoromethyl)benzyl]sulfonyl}amino)ethyl]-1H-indol-3-yl}ethoxy)benzoic acid Step 1: To the methyl 4-{2-[2-(2-aminoethyl)-1-benzhydryl-5-chloro-1H-indol-3-yl]ethoxy}benzoate (Step 5, Example 1)was added ([3-(trifluoromethyl)phenyl]methyl}sulfonyl chloride according to the procedure in Example 1 Step 7 to generate the product in 74% yield.

Step 2: The ester intermediate was hydrolyzed according to Step 8 Example 1 to afford the title acid in 86% yield. HRMS calc for $[C_{40}H_{34}ClF_3N_2O_5S+H]$ 747.1902 found 747.1904

Example 48

2-{[(2-{[(2-{1-benzhydryl-3-[2-(4-carboxyphenoxy)ethyl]-5-chloro-1H-indol-2-yl}ethyl)amino]sulfonyl}ethyl)amino]carbonyl}benzoic acid Step 1: To the methyl 4-{2-[2-(2-aminoethyl)-1-benzhydryl-5-chloro-1H-indol-3-yl]ethoxy}benzoate (Step 5, Example 1)was added 2-phthalimidoethanesulfonyl chloride according to the procedure in Example 1 Step 7 to generate the product in 78% yield.

Step 2: The ester intermediate was hydrolyzed according to Step 8 Example 1 to afford the title acid in 99% yield. HRMS calc for $[C_{42}H_{38}ClN_3O_8S+H]$ 780.2141 found 780.2148

Example 49

4-{2-[{1-benzhydryl-5-chloro-2-(2-{[(3-pyridinylmethyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 5, Example 1) was added (3-pyridylmethyl)sulfonyl chloride according to the procedure in Example 1 Step 7 to generate the product in 52% yield.

Step 2: The ester intermediate was hydrolyzed according to Step 8 Example 1 to afford the title acid in 94% yield. HRMS calc for $[C_{38}H_{34}ClN_3O_5S-H]$ 678.18349 found 678.18277.

Example 50

4-{2-[{1-benzhydryl-5-chloro-2-(2-{[(4-pyridinylmethyl)sulfonyl]amino}ethyl)-1H-indol-3-yl]ethoxy}benzoic acid Step 1: To the methyl 4-{-2-[2-(2-aminoethyl)-1-benzhydryl-5-chloro-1H-indol-3-yl]ethoxy}benzoate (Step 5, Example 1)was added (4-pyridylmethyl)sulfonyl chloride according to the procedure in Example 1 Step 7 to generate the product in 57% yield.

Step 2: The ester intermediate was hydrolyzed according to Step 8 Example 1 to afford the title acid in 100% yield. m/z (M−1) HRMS calc for $[C_{38}H_{34}ClN_3O_5S-H]$ 678.18349 found 678.18249

Example 51

4-{2-[{1-benzhydryl-5-chloro-2-(2-{[(2-pyridinylmethyl)sulfonyl]amino}ethyl)-1H-indol-3-yl]ethoxy}benzoic acid Step 1: To the methyl 4-{2-[2-(2-aminoethyl)-1-benzhydryl-5-chloro-1H-indol-3-yl]ethoxy}benzoate (Step 5, Example 1)was added (2-pyridylmethyl)sulfonyl chloride according to the procedure in Example 1 Step 7 to generate the product in 42% yield.

Step 2: The ester intermediate was hydrolyzed according to Step 8 Example 1 to afford the title acid in 56% yield. HRMS calc for $[C_{38}H_{34}ClN_3O_5S-H]$ 678.18349 found 678.18312

Example 52

4-{3-[1-benzhydryl-5-chloro-2-(2-{[(2,6-dimethylbenzyl)sulfonyl]amino}ethyl)-1H-indoly-3-yl]propyl}benzoic acid Step 1: The sulfonyl chloride intermediate was prepared from 2,6-dimethylbenzyl chloride according to the procedure in Example 18 Step 1–2 in 100% yield.

Step 2: The methyl ester was prepared from the sulfonyl chloride and the intermediate in Example 42 step 6 according to the procedure in Example 42 Step 7 in 30% yield.

Step 3: The ester intermediate was hydrolyzed according to Step 8 Example 43 to afford the title acid in 100% yield. HRMS calc for $[C_{42}H_{41}ClN_2O_4S -H]$ 703.24028 found 703.23973

Example 53

4-{2-[1-benzhydryl-5-chloro-2-(2-{[(cyclohexylmethyl)sulfonyl]amino}ethyl)-1H-indol-3-yl]ethoxy}benzoic acid Step 1: The sulfonyl chloride intermediate was prepared from (bromomethyl)cyclohexane according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 20% yield.

Step 3: The ester intermediate was hydrolyzed according to Step 8 Example 1 to afford the title acid in 73% yield. HRMS calc for [$C_{39}H_{41}ClN_2O_5S$–H] 683.23519 found 683.23474

Example 54

4-{2-[1-benzhydryl-5-chloro-2-(2-{[(4-nitrobenzyl)sulfonyl]amino}ethyl)-1H-indol-3-yl]ethoxy}benzoic acid Step 1: The sulfonyl chloride intermediate was prepared from 4-nitrobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 80% yield.

Step 3: The ester intermediate was hydrolyzed according to Step 8 Example 1 to afford the title compound in 90% yield. HRMS calc for [$C_{39}H_{34}ClN_3O_7S$+H] 724.1879 found 724.1884.

Example 55

4-{2-[1-benzhydryl-5-chloro-2-(2-{[(3-nitrobenzyl)sulfonyl]amino}ethyl)-1H-indol-3-yl]ethoxy}benzoic acid Step 1: The sulfonyl chloride intermediate w as prepared from 3-nitrobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 85% yield.

Step 3: The ester intermediate was hydrolyzed according to Step 8 Example 1 to afford the title compound in 85% yield. HRMS calc for [$C_{39}H_{34}ClN_3O_7S$+H] 724.1879 found 724.1885.

Example 56

4-{2-[1-Benzhydryl-5-chloro-2-{2-[({2-nitrobenzyl}-sulfonyl)amino]ethyl}-1H-indol-3-yl)propyl] benzoic acid Step 1: To the methyl 4-{2-[2-(2-aminoethyl)-1-benzhydryl-5-chloro-1H-indol-3-yl]propyl}benzoate (Step 6, Example 42) was added and 2-nitro-□-toluenesulfonyl chloride according to the procedure in Example 1 Step 7 to generate the product in 65% yield.

Step 2: The ester intermediate was hydrolyzed according to Step 8 Example 1 to afford the title acid in 100% yield. HRMS calc for [$C_{40}H_{36}ClN_3O_6S$+H] 722.2086 found 722.2088.

Example 57

4-{3-[1-benzhydryl-5-chloro-2-(2-{[(4-fluorobenzyl)sulfonyl]amino}ethyl)-1H-indol-3-yl]propyl]benzoic acid Step 1: To the methyl 4-{2-[2-(2-aminoethyl)-1-benzhydryl-5-chloro-1H-indol-3-yl]propyl}benzoate (Step 6, Example 42) was added and (4-Fluoro-phenyl)-methanesulfonyl chlorideaccording to the procedure in Example 1 Step 7 to generate the product in 77% yield.

Step 2: The ester intermediate was hydrolyzed according to Step 8 Example 1 to afford the title acid in 68% yield. HRMS calc for [$C_{40}H_{36}ClFN_2O_4S$+H] 695.2141 found 695.2145.

Example 58

4-(3-{1-benzhydryl-5-chloro-2-[2-({[4-(trifluoromethyl)benzyl]sulfonyl}amino)ethyl]-1H-indol-3-yl}propyl)benzoic acid Step 1: To the methyl 4-{2-[2-(2-aminoethyl)-1-benzhydryl-5-chloro-1H-indol-3-yl]propyl}benzoate (Step 6, Example 42) was added and (4-Trifluoromethyl-phenyl)-methanesulfonyl chloride according to the procedure in Example 1 Step 7 to generate the product in 50% yield.

Step 2: The ester intermediate was hydrolyzed according to Step 8 Example 1 to afford the title acid in 100% yield. HRMS calc for [$C_{41}H_{36}ClF_3N_2O_4S$+H] 745.2109 found 745.2114.

Example 59

4-(3-{1-benzhydryl-5-chloro-2-[2-({[3-(trifluoromethyl)benzyl]sulfonyl}amino)ethyl]-1H-indol-3-yl}propyl)benzoic acid Step 1: To methyl 4-{2-[2-(2-aminoethyl)-1-benzhydryl-5-chloro-1H-indol-3-yl]propyl}benzoate (Step 6, Example 42) was added and (3-Trifluoromethyl-phenyl)-methanesulfonyl chloride according to the procedure in Example 1 Step 7 to generate the product in 56% yield.

Step 2: The ester intermediate was hydrolyzed according to Step 8 Example 1 to afford the title acid in 82% yield. HRMS calc for [$C_{41}H_{36}ClF_3N_2O_4S$+H] 745.2109 found 745.211.

Example 60

4-{3-[1-benzhydryl-5-chloro-2-(2-{[(4-chlorobenzyl)sulfonyl]amino}ethyl)-1H-indol-3-yl[propyl}benzoic acid Step 1: To the methyl methyl 4-{2-[2-(2-aminoethyl)-1-benzhydryl-5-chloro-1H-indol-3-yl]propyl}benzoate (Step 6, Example 42) was added and (4-chlorophenyl)-methanesulfonyl chloride according to the procedure in Example 1 Step 7 to generate the product in 74% yield.

Step 2: The ester intermediate was hydrolyzed according to Step 8 Example 1 to afford the title acid in 79% yield. HRMS calc for [$C_{40}H_{36}Cl_2N_2O_4S$+H] 711.1846 found 711.1847.

Example 61

4-{3-[1-benzhydryl-5-chloro-2-(2-{[(2-pyridinylmethyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added pyridin-2-yl-methanesulfonyl chloride chloride according to the procedure in Example 4 Step 1 to generate the product in 75% yield.

Step 2: The ester intermediate was hydrolyzed according to Step 8 Example 1 to afford the title acid in 96% yield. HRMS calc for $[C_{39}H_{36}ClN_3O_4S+H]$ 678.2188 found 678.2187.

Example 62

4-(3-[1-benzhydryl-5-chloro-2-(2-{[(3-pyridinylmethyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added pyridin-3-yl-methanesulfonyl chloride chloride according to the procedure in Example 4 Step 1 to generate the product in 75% yield.

Step 2: The ester intermediate was hydrolyzed according to Step 8 Example 1 to afford the title acid in 88% yield.

Example 63

4-{3-[1-benzhydryl-5-chloro-2-(2-{[(4-pyridinylmethyl)sulfonyl]amino}ethyl)-1H-indol-3-yl]propyl}benzoic acid Step 1: To the methyl 4-{2-[2-(2-aminoethyl)-1-benzhydryl-5-chloro-1H-indol-3-yl]propyl}benzoate (Step 6, Example 42) was added pyridin-4-yl-methanesulfonyl chloride chloride according to the procedure in Example 4 Step 1 to generate the product in 75% yield.

Step 2: The ester intermediate was hydrolyzed according to Step 8 Example 1 to afford the title acid in. 77% yield. HRMS calc for $[C_{39}H_{36}ClN_3O_4S-H]$ 676.20423 found 676.20405

Example 64

4-{3-[1-benzhydryl-5-chloro-2-(2{[(2-chlorobenzyl)sulfonyl]amino}ethyl)-1H-indol-3-yl]propyl}benzoic acid Step 1: The sulfonyl chloride intermediate was prepared from 3-chlorobenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 10% yield.

Step 3: The ester intermediate was hydrolyzed according to Step 8 Example 1 to afford the title compound in 100% yield. HRMS calc for $[C_{40}H_{36}Cl_2N_2O_4S-H]$ 709.17000 found 709.16961

Example 65

4-{3-[1-benzhydryl-5-chloro-2-(2-{[(3-nitrobenzyl)sulfonyl]amino}ethyl)-1H-indol-3-yl]propyl}benzoic acid Step 1: The sulfonyl chloride intermediate was prepared from 3-nitrobenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 43% yield.

Step 3: The ester intermediate was hydrolyzed according to Step 8 Example 1 to afford the title compound in 88% yield. HRMS calc for $[C_{40}H_{36}ClN_3O_6S-H]$ 720.19405 found 720.19398

Example 66

4-{3-[1-benzhydryl-5chloro-2-(2{[(3-chlorobenzyl)sulfonyl]amino}ethyl)-1H-indol-3-yl]propyl}benzoic acid Step 1: The sulfonyl chloride intermediate was prepared from 3-chlorobenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 27% yield.

Step 3: The ester intermediate was hydrolyzed according to Step 8 Example 1 to afford the title compound in 93% yield. HRMS calc for $[C_{40}H_{36}Cl_2N_2O_4S-H]$ 709.17000 found 709.16963

Example 67

4-{3-[1-benzhydryl-5-chloro-2-(2-{[(2,5-dichlorobenzyl)sulfonyl]amino}ethyl)-1H-indol-3-yl]propyl}benzoic acid Step 1: The sulfonyl chloride intermediate was prepared from 2,5-dichlorobenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 59% yield.

Step 3: The ester intermediate was hydrolyzed according to Step 8 Example 1 to afford the title compound in 100% yield. HRMS calc for $[C_{40}H_{35}Cl_3N_2O_4S-H]$ 743.13103 found 743.13079

Example 68

4-{3-[1-benzhydryl-5-chloro-2-(2-{[(3-methoxybenzyl)sulfonyl]amino}ethyl)-1H-indol-3-yl]propyl}benzoic acid Step 1: The sulfonyl chloride intermediate was prepared from 3-methoxybenzyl bromide according to the procedure in Example 18 Step 1–2.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 6, Example 42) according to the procedure in Example 1 Step 7 in 20% yield.

Step 3: The ester intermediate was hydrolyzed according to Step 8 Example 1 to afford the title compound in 100% yield. HRMS calc for $[C_{41}H_{39}ClN_2O_5S-H]$ 705.21954 found 705.21909

Example 69

4-{3-[2-(2-{[(2-aminobenzyl)sulfonyl]amino}ethyl)-1-benzhydryl-5-chloro-1H-indol-3-yl]propyl}benzoic acid Step 1: The intermediate from Step 1 Example 56 was treated with $SnCl_2$ according to the procedure in Step 1 Example 16 to yield the amino ester in 99% yield.

Step 2: The ester intermediate was hydrolyzed according to Step 8 Example 1 to afford the title acid in 100% yield. HRMS calc for $[C_{40}H_{38}ClN_3O_4S-H]$ 690.21988 found 690.21941

Example 70

4-{3-[1-Benzhydryl-5-chloro-2-(2-{[(2-methylbenzyl)sulfonyl]amino}ethyl)-1H-indol-3-yl]propyl}benzoic acid Step 1: The sulfonyl chloride intermediate was prepared from 2-Methylbenzyl bromide according to the procedure in Example 18 Step 1–2 in quantitative yield.

Step 2: The methyl ester was prepared from the sulfonyl chloride and the intermediate in Example 42 step 6 according to the procedure in Example 42 Step 7 in 50% yield.

Step 2: The ester intermediate was hydrolyzed according to Step 8 Example 43 to afford the title acid in 93% yield. HRMS calc for $[C_{41}H_{39}ClN_2O_4S-H]$ 689.22463 found 689.22421

Example 71

4-{2-[1-Benzhydryl-5-chloro-2-(2-{[(4-trifluorometoxybenzyl)sulfonyl]amino}ethyl)-1H-indol-3-yl]ethoxy}benzoic acid Step 1: The sulfonyl chloride intermediate was prepared from 4-Trifluorometoxybenzyl bromide according to the procedure in Example 18 Step 1–2 in quantitative yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 48% yield.

Step 2: The ester intermediate was hydrolyzed according to Step 8 Example 1 to afford the title acid in 85% yield. HRMS calc for $[C_{40}H_{34}ClF_3N_2O_6S-H]$ 761.17054 found 761.17031

Example 72

4-{2-[1-Benzhydryl-5-chloro-2-(2-{[(2-fluoro-6-nitrobenzyl)sulfonyl]amino}ethyl)-1H-indol-3-yl]ethoxy)benzoic acid Step 1: The sulfonyl chloride intermediate was prepared from 2-Fluoro, 6-nitrobenzyl, bromide according to the procedure in Example 18 Step 1–2 in quantitative yield.

Step 2: The methyl ester was prepared from the sulfonyl chloride and methyl 4-{2-[2-(2-aminoethyl)-1-benzhydryl-5-chloro-1H-indol-3-yl]ethoxy)benzoate (Step 5, Example 1) according to the procedure in Example 1 Step 7 in 91% yield.

Step 2: The ester intermediate was hydrolyzed according to Step 8 Example 1 to afford the title acid in 100% yield. m/z (M-1) 740.05

Example 73

4-{2-[1-Benzhydryl-5-chloro-2-(2-{[(2-dichlorobenzyl)sulfonyl]amino}ethyl)-1H-indol-3-yl]ethoxy}benzoic acid Step 1:. The c chloride intermediate was prepared from 3,5-dichlorobenzyl bromide according to the procedure in Example 18 Step 1–2 in theoritical yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 100% yield.

Step 2: The ester intermediate was hydrolyzed according to Step 8 Example 1 to afford the title acid in 81% yield. m/z (M-1) 747.2.HRMS calc for $[C_{39}H_{33}Cl_3N_2O_5S-H]$ 745.11030 found 745.10954.

Example 74

4-{2-[1-Benzhydryl-5-chloro-2-(2[(2,6-difluorobenzyl)sulfonyl]amino}ethyl)-1H-indol-3-yl]ethoxy}benzoic acid Step 1: The sulfonyl chloride intermediate was prepared from 2,6-difluorobenzyl bromide according to the procedure in Example 18 Step 1–2 in 95% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 86% yield.

Step 2: The ester intermediate was hydrolyzed according to Step 8 Example 1 to afford the title acid in 71% yield. m/z (M-1)714.HRMS calc for $[C_{39}H_{33}ClF_2N_2O_5S-H]$ 713.16940 found 713.16906

Example 75

4-(2-{1-benzhydryl-5-chloro-2-[2-({[(6-chloro-3-pyridinyl)methyl]sulfonyl}amino)ethyl]-1H-indol-3-yl}ethoxy)benzoic acid Step 1: (6-chloro-3-pyridinyl)-methanol (1.0 eq.) was taken up in dichloromethane and stirred overnight with carbon tetrabromide (1.5 eq.) and 1,3-bis (diphenylphosphino)propane (0.75 eq.) Ether was added to the solution and filtration followed by concentration of the filtrate afforded (6-chloro-3-bromomethyl) pyridine in 62% yield.

Step 2: The sulfonyl chloride intermediate was prepared from the product of Step 1 according to the procedure in Example 18 steps 1–2.

Step 3: The methyl ester was prepared from the sulfonyl chloride and methy 4-{2-[2-(2-aminoethyl)-1-benzhydryl-5-chloro-1H-indol-3-yl]ethoxy}benzoate (Step 5, Example 1) according to the procedure in Example 1 Step 7 in 78% yield Step 4: The ester intermediate was hydrolyzed according to Step 8 Example 1 to afford the title acid in 89% yield. HRMS calc for $[C_{38}H_{33}Cl_2N_3O_5S-H]$ 712.14452 found 712.14420.

Example 76

4-(2-{1-benzhydryl-5-chloro-2-[2-({[(5,6-dichloro-2-[pyridinyl)methyl]sulfonyl}amino)ethyl]-1H-indol-3-yl}ethoxy)benzoic acid Step 1: 5,6-dichloro-3-pyridinemethanol (1.0 eq.) was taken up in dichloromethane and stirred overnight with carbon tetrabromide (1.5 eq.) and 1,3-bis (diphenylphosphino)propane (0.75 eq.) Ether was added to the solution and filtration followed by concentration of the filtrate afforded the 5,6-dichloro-3-bromomethylpyridine in 130% yield.

Step 2: The sulfonyl chloride intermediate was prepared from the product of Step 1 according to the procedure in Example 18 steps 1–2 in 81% yield Step 3: The methyl ester was prepared from the sulfonyl chloride and methy 4-{2-[2-(2-aminoethl)-1-benzhydryl-5-chloro-1H-indol-3-yl]ethoxy}benzoate (Step 5, Example 1) according to the procedure in Example 1 Step 7 in 79% yield Step 4: The ester intermediate was hydrolyzed according to Step 8 Example 1 to afford the title acid in 109% yield. HRMS calc for $[C_{38}H_{32}Cl_3N_3O_5S-H]$ 746.10554 found 746.10549.

Example 77

4-{2-[1-Benzhydryl-5chloro-2-(2-{[(3-methoxybenzyl)sulfonyl]amino}ethyl)-1H-indol-3-yl]ethoxy}benzoic acid Step 1: The sulfonyl chloride intermediate was prepared from 3-methoxybenzyl bromide according to the procedure in Example 18 Step 1–2 in 68% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 68% yield.

Step 2: The ester intermediate was hydrolyzed according to Step 8 Example 1 to afford the title diacid in 93% yield. m/z (M−1) 707.0

Example 78

4-{2-[1-Benzhydryl-5-chloro-2-(2-{[(3,5-dimethylbenzyl)sulfonyl]amino}ethyl)-1H-indol-3-yl]ethoxy)benzoic acid Step 1: The sulfonyl chloride intermediate was prepared from 3,5-dimethylbenzyl bromide according to the procedure in Example 18 Step 1–2 in 38% yield.

Step 2: The methyl ester was prepared from the sulfonyl chloride and methyl 4-{2-[2-(2-aminoethyl)-1-benzhydryl-5-chloro-1H-indol-3-yl]ethoxy)benzoate (Step 5, Example 1) according to the procedure in Example 1 Step 7 in 38% yield.

Step 2: The ester intermediate was hydrolyzed according to Step 8 Example 1 to afford the title diacid in 88% yield. m/z (M−1)705.0 HRMS calc for $[C_{41}H_{39}ClN_2O_5S-H]$ 705.21954 found 705.21916.

Example 79

4-{2-[1-Benzhydryl-5-chloro-2-(2-{[(2-methylbenzyl)sulfonyl]amino}ethyl)-1H-indol3-yl]ethoxy}benzoic acid Step 1: The sulfonyl chloride intermediate was prepared from 2-methylbenzyl bromide according to the procedure in Example 18 Step 1–2 in 35% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 35% yield.

Step 2: The ester intermediate was hydrolyzed according to Step 8 Example 1 to afford the title diacid in 90% yield. m/z (M−1)691.0.HRMS calc for $[C_{40_1}H_{37}ClN_2O_5S-H]$ 691.20389 found 691.20350

Example 80

4-{2-[1-Benzhydryl-5-chloro-2-(2-{[(2,6-dichlorobenzyl)sulfonyl]amino}ethyl)-1H-indol-3-yl]ethoxy}benzoic acid Step 1: The sulfonyl chloride intermediate was prepared from 2,6-dichlorobenzyl bromide according to the procedure in Example 18 Step 1–2 in 3% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7 in 3% yield.

Step 2: The ester intermediate was hydrolyzed according to Step 8 Example 1 to afford the title diacid in 92% yield. m/z (M−1)745.0

Method C

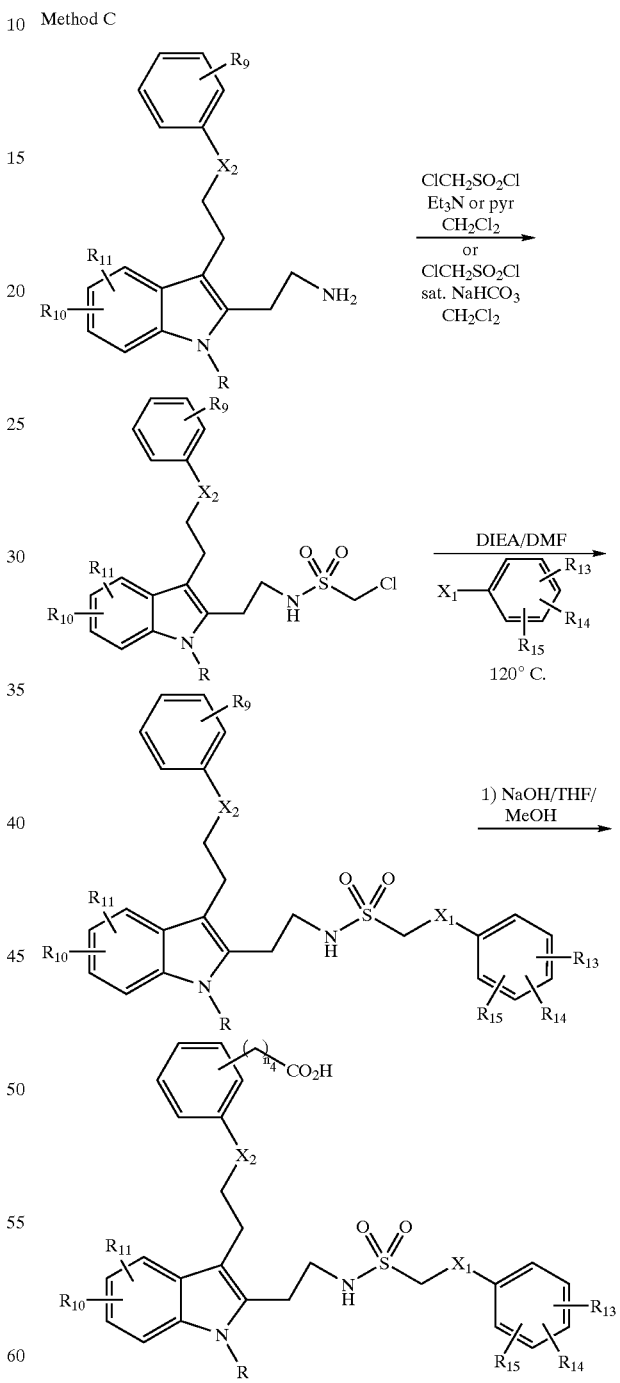

The intermediate amine, synthesized using method A, was treated with chloromethylsulfonyl chloride either under Schott and Baumman conditions or under anhydrous conditions with an organic base yielded a chloromethyl sulfonamide intermediate. This intermediate could be treated with a variety of nucleophiles in DMF with a suitable organic base, Hunigs base, triethylamine etc, and heated until the reaction was complete. The resulting intermediates where then hydrolyzed to yield the final compound. $R_{13}$, $R_{14}$ and $R_{15}$ in the scheme for Method C, above, represent the optional substitution defined above for $R_{12}$.

Examples 81–86 and 118–121 were synthesized using Method C.

Example 81

4-(2-{1-benzhydryl-5-chloro-2-[2-({ [(phenylsulfanyl) methyl]sulfonyl}amino) ethyl]-1H-indol-3-yl}ethoxy)benzoic acid The title compound was synthesized as depicted in Method C.

Step 1: To the methyl 4-{2-[2-(2-aminoethyl)-1-benzhydryl-5-chloro-1H-indol-3-yl]ethoxy}benzoate (Step 5, Example 1) was added chloromethanesulfonyl chloride according to the procedure in Example 1 Step 7 to generate the product in 99% yield.

Step 2: To methyl 4-{2-[1-benzhydryl-5-chloro-2-(2{[(chloromethyl)sulfonyl]amino}ethyl)-1H-indol-3-yl] ethoxy}benzoate (0.080M, 1.0 equiv.) and $^{i}Pr_2NEt$ (3.4 equiv.) in N,N-dimethylformamide was added thiophenol (2.1–2.5 equiv.) and the mixture was stirred at 120° C. for 3.5 days. The reaction mixture was diluted with EtOAc and washed with water and brine. The combined organic phase was dried over magnesium sulfate and purified by flash chromatography.

Step 3: The ester intermediate was hydrolyzed according to Step 8 Example 1 to afford the title acid in 93% yield. m/z (M-1) 709.11. HRMS calc for $[C_{39}H_{35}ClN_2O_5S_2$-H] 709.16031 found 709.15999.

Example 82

4-(2-{1-benzhydryl-5-chloro-2-[2(2,6-dimethyl-phenylsulfanylmethanesulfonylamino)-ethyl]-]-1H-indol-3-yl}-ethoxy)-benzoic acid Step 1: To methyl 4-{2-[1-benzhydryl-5-chloro-2-(2-{ [(chloromethyl)sulfonyl]amino}ethyl)-'1H-indol-3-yl] ethoxy}benzoate, Example 81 step 1, was added 2,6-dimethylthiophenol according to the procedure in Example 81 step 2 and 3. The product was purified by the flash chromatography with 25% EtOAc/hexane in 32% yield.

Step 2: The ester intermediate was hydrolyzed according to Step 8 Example 43 to afford the title acid in 80% yield. m/z (M-1)751.0. HRMS calc for $[C_{41}H_{39}ClN_2O_5S_2$ -H] 737.19161 found 737.19128.

Example 83

4-(2-(1-benzhydryl-5-chloro-2-[2-(2-methoxy-phenylsulfanylmethanesulfonylamino)-ethyl]-]-1H-indol-3-yl}-ethoxy)-benzoic acid Step 1:To methyl 4-{2-[1-benzhydryl-5-chloro-2-(2-{ [(chloromethyl)sulfonyl]amino}ethyl)-'1H-indol-3-yl] ethoxy}benzoate, Example 81 step 1, was added 2-methoxythiophenol according to the procedure in Example 81 step 2 and 3. The product was purified by the flash chromatography 30% EtOAc/hexane in 36% yield.

Step 2: The ester intermediate was hydrolyzed according to Step 8 Example 43 to afford the title acid in 94% yield. m/z (M-1) 753.3. HRMS calc for $[C_{40}H_{37}ClN_2O_6S_2$ -H] 739.17088 found 739.17052.

Example 84

4-(2-{1-benzhydryl-5-chloro-2-[2-(2-chloro-6-methyl-phenylsulfanylmethanesulfonylamino)-ethyl]-]-1H-indol-3-yl}-ethoxy)-benzoic acid Step 1: To methyl 4-2-[1-benzhydryl-5-chloro-2-(2-{ [(chloromethyl)sulfonyl]amino}ethyl)-'1H-indol-3-yl] ethoxy}benzoate, Example 81 step 1, was added 2-chloro-6-methylthiophenol according to the procedure in Example 81 step 2 and 3. The product was purified by the flash chromatography 25% EtOAc/hexane in 46% yield.

Step 2: The ester intermediate was hydrolyzed according to Step 8 Example 43 to afford the title acid in 100% yield. m/z (M-1)771.2. HRMS calc for $[C_{40}H_{36}Cl_2N_2O_5S_2$-H] 757.13699 found 757.13730.

Example 85

4-(2-{1-benzhydryl-5-chloro-2-[2-(3,5-dichloro-phenylsulfanylmethanesulfonylamino)-ethyl]-]-1H-indol-3-yl}-ethoxy)-benzoic acid Step 1: To methyl 4-2-[1-benzhydryl-5-chloro-2-(2-{ [(chloromethyl)sulfonyl]amino}ethyl)-'1H-indol-3-yl] ethoxy}benzoate, Example 81 step 1, was added 3,5-dichlorothiophenol according to the procedure in Example 81 step 2 and 3. The product was purified by the flash chromatography 25% EtOAc/hexane in 40% yield.

Step 2: The ester intermediate was hydrolyzed according to Step 8 Example 43 to afford the title acid in 98% yield. m/z (M-1)793.2. HRMS calc for $[C_{39}H_{33}Cl_3N_2O_5S_2$-H] 777.08237 found 777.08159.

Example 86

4-(2-{1-benzhydryl-5-chloro-2-[2-(3,4-dimethoxy-phenylsulfanylmethanesulfonylamino)-ethyl]-]-1H-indol-3-yl}-ethoxy)-benzoic acid Step 1: To methyl 4-{2-[1-benzhydryl-5-chloro-2-(2-{ [(chloromethyl)sulfonyl]amino}ethyl)-'1H-indol-3-yl] ethoxy}benzoate, Example 81 step 1, was added 3,4-dimethoxythiophenol according to the procedure in Example 81 step 2 and 3. The product was purified by the flash chromatography with 35% EtOAc/hexane in 40% yield.

Step 2: The ester intermediate was hydrolyzed according to Step 8 Example 43 to afford the title acid in 99% yield. m/z (M-1)783.3. HRMS calc for $[C_{41}H_{39}ClN_2O_7S_2$-H] 769.18144 found 769.18120.

Method D

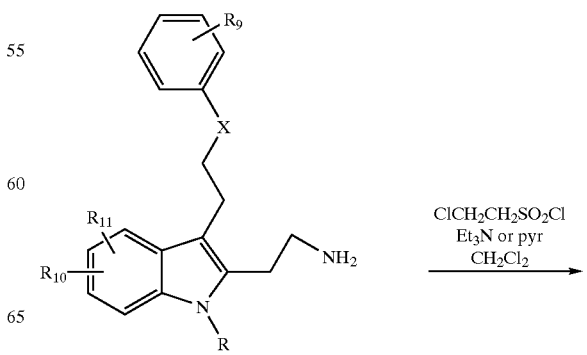

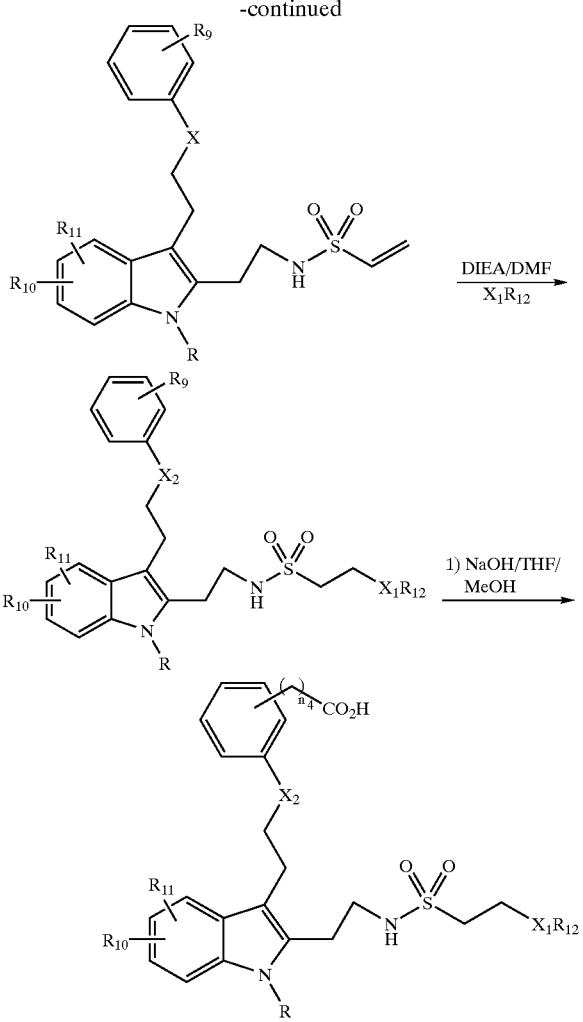

The intermediate amine, synthesized using method A, was treated with chloroethanesulfonyl chloride under anhydrous conditions with an organic base yielded a vinyl sulfonamide intermediate. This intermediate could be treated with a variety of nucleophiles in DMF with a suitable organic base, Hunigs base, triethylamine etc, and heated until the reaction was complete. The resulting intermediates where then hydrolyzed to yield the final compound.

Examples 87–99 and 100–105, 113–117, 122–125 and 139 were synthesized with Method D.

Example 87

4-(2-{1-Benzhydryl-5-chloro-2-[2-(2-morpholin-4-ylethanesulfonylamino)-ethyl]-1H-indol-3-yl}-ethoxy)-benzoic acid The title compound was synthesis as depicted in Method D Step 1: To methyl 4-2-[2-(2-aminoethyl)-1-benzhydryl-5-chloro-1H-indol-3-yl]ethoxy}benzoate (0.16M, 1.0 equiv.), Step 5, Example 1, and triethylamine (2.3 equiv.) in THF was added 2-chloroethanesulfonyl chloride (1.2 eq) dropwise. After 4 h the mixture was poured into brine and extracted with EtOAc. The combined organic phase was dried over magnesium sulfate and purified by column chromatography to afford 75% of the vinyl sulfonamide.

Step 2: To the product from step 1 in 1-propanol was added morpholine. After 5 h the reaction mixture was evaporated to dryness before redissolving in EtOAc. The organic phase was washed with brine, dried over magnesium sulfate, and purified by column chromatography to give the desired methyl ester in 89% yield.

Step 3: The ester intermediate was hydrolyzed according to Step 8 Example 1 to afford the title acid in 89% yield. m/z (M-1) 702.17. HRMS calc for $[C_{38}H_{40}ClN_3O_6S$ -H] 700.2535 found 700.22500.

Example 88

4-(2-{1-Benzhydryl-5-chloro-2-[2-(2-pyrazol-1-yl-ethanesulfonylamino)-ethyl]-1H-indol-3-yl}-ethoxy)-benzoic acid Step 1: The compound was prepared from the intermediate from Example 87 step 1 and 1H-pyrazole according to the procedure in Example 87 step 2 except that it was heated at 80° C. for 18 h, in 90% yield.

Step 2: The ester intermediate was hydrolyzed according to Step 8 Example 1 to afford the title acid in 61% yield. m/z (M-1) 681.24. HRMS calc for $[C_{37}H_{35}ClN_4O_5S$ -H] 681.19439 found 681.19407.

Example 89

4-(2-{1-Benzhydryl-5-chloro-2-[2-(2-phenylamino-ethanesulfonylamino)-ethyl]-1H-indol-3-yl}-ethoxy)-benzoic acid Step 1: The compound was prepared from the intermediate from Example 87 step 1 and aniline according to the procedure in Example 87 step 2 except that it was heated at 80° C. for 8 days, in 50% yield.

Step 2: The ester intermediate was hydrolyzed according to Step 8 Example 1 to afford the title acid in 98% yield. m/z (M-1) 706.26. HRMS calc for $[C_{40}H_{38}ClN_3O_5S$ -H] 706.21479 found 706.21452.

Example 90

4-(2-{1-benzhydryl-5-chloro-2-[2-({[2-(1,4-dioxa-8-azaspiro[4.5]dec-8-yl)ethyl]sulfonyl}amino)ethyl]-1H-indol-3-yl}ethoxy)benzoic acid Step 1: The compound was prepared from the intermediate from Example 87 step 1 and 1,4-dioxa-8-aza-spiro[4.5] decane according to the procedure in Example 87 step 2 except that it was stirred overnight, in 82% yield.

Step 2: The ester intermediate was hydrolyzed according to Step 8 Example 1 to afford the title acid in 100% yield. m/z (M-1) 756.2. HRMS calc for $[C_{41}H_{44}ClN_3O_7S$ -H] 756.25157 found 756.25142.

Example 91

4-[2-(1-benzhydryl-5-chloro-2-{2-[({2-[4-(2-pyridinyl)-1-piperazinyl]ethyl}sulfonyl)amino]ethyl}-1H-indol-3-yl)ethoxy]benzoic acid Step 1: The compound was prepared from the intermediate from Example 87 step 1 and 1-Pyridin-2-yl-piperazine according to the procedure in Example 87 step 2 except that it was stirred overnight, in 86% yield.

Step 2: The ester intermediate was hydrolyzed according to Step 8 Example 1 to afford the title acid in 100% yield. m/z (M-1) 776.2. HRMS calc for $[C_{43}H_{44}ClN_5O_5S$ -H] 776.26789 found 776.26750.

Example 92

4-(2-{1-benzhydryl-5-chloro-2-[2-({[2-(1H-1,2,4-triazol-1-yl)ethyl]sulfonyl}amino)ethyl]-1H-indol-3-yl}ethoxy)benzoic acid Step 1: The compound was prepared from the intermediate from Example 87 step 1 and 1H-[1,2,4]triazole according to the procedure in Example 87 step 2 except that it was refluxed for 4 days, in 64% yield Step 2: The ester intermediate was hydrolyzed according to Step 8 Example 1 to afford the title acid in 100% yield. m/z (M-1) 682.1. HRMS calc for $[C_{36}H_{34}ClN_5O_5S$-H$]$ 682.18964 found 682.18964.

Example 93

4-(2-{1-benzhydryl-5-chloro-2-[2-({[2-(3,5-dimethyl-1H-pyrazol-1-yl)ethyl]sulfonyl}amino)ethyl]-1H-indol-3-yl}ethoxy)benzoic acid Step 1: The compound was prepared from the intermediate from Example 87 step 1 and 3,5-dimethyl-1H-pyrazole according to the procedure in Example 87 step 2 except that it was refluxed for refluxed 24 hours, in 95% yield.

Step 2: The ester intermediate was hydrolyzed according to Step 8 Example 1 to afford the title acid in 62% yield. m/z (M-1) 709.2. HRMS calc for $[C_{39}H_{39}ClN_4O_5S$-H$]$ 709.22569 found 709.22532.

Example 94

4-(2-{1-benzhydryl-5-chloro-2-[2-({[2-(3-methyl-1H-pyrazol-1-yl)ethyl]sulfonyl}amino)ethyl]-1H-indol-3-yl}ethoxy)benzoic acid Step 1: The compound was prepared from the intermediate from Example 87 step 1 and 3-methyl-1H-pyrazole according to the procedure in Example 87 step 2 except that it was stirred overnight, in 88% yield.

Step 2: The ester intermediate was hydrolyzed according to Step 8 Example 1, except that the pH was adjusted to 4–5, to afford the title acid in 86% yield. m/z (M-1) 695.2. HRMS calc for $[C_{38}H_{37}ClN_4O_5S$ -H$]$ 695.21004 found 695.20951.

Example 95

4-(2-{1-benzhydryl-5-chloro-2-[2-({[2-(4-methyl-1H-pyrazol-1-yl)ethyl]sulfonyl}amino)ethyl]-1H-indol-3-yl}ethoxy)benzoic acid Step 1: The compound was prepared from the intermediate from Example 87 step 1 and 4-methyl-1H-pyrazole according to the procedure in Example 87 step 2 except that it was refluxed for 2 days, in 81% yield.

Step 2: The ester intermediate was hydrolyzed according to Step 8 Example 1, except that the pH was adjusted to 4–5, to afford the title acid in 93% yield. m/z (M-1) 695.2. HRMS calc for $[C_{38}H_{37}ClN_4O_5S$ -H$]$ 695.21004 found 695.20954.

Example 96

4-[2-(1-benzhydryl-5-chloro-2-{2-[({2-[(2R,6S)-2,6-dimethyl-1-piperidinyl]ethyl}sulfonyl)amino]ethyl}-1H-indol-3-yl)ethoxy]benzoic acid Step 1: The compound was prepared from the intermediate from Example 87 step 1 and 2,6-dimethyl-piperidine according to the procedure in Example 87 step 2 except that it was heated at 70° C. overnight, in 54% yield.

Step 2: The ester intermediate was hydrolyzed according to Step 8 Example 1, except that the pH was adjusted to 4–5, to afford the title acid in 79% yield. m/z (M-1) 726.3. HRMS calc for $[C_{41}H_{46}ClN_3O_5S$ -H$]$ 726.27739 found 726.27720.

Example 97

4-(2-{1-benzhydryl-5-chloro-2-[2-({[2-(2-thioxo-1-imidazolidinyl)ethyl]sulfonyl}amino)ethyl]-1H-indol-3-yl}ethoxy)benzoic acid Step 1: The compound was prepared from the intermediate from Example 87 step 1 and imidazolidine-2-thione according to the procedure in Example 87 step 2 except that it was refluxed for 3 days, in 17% yield.

Step 2: The ester intermediate was hydrolyzed according to Step 8 Example 1, except that the pH was adjusted to 4–5, to afford the title acid in 88% yield. m/z (M-1) 715.3. HRMS calc for $[C_{37}H_{37}ClN_4O_5S$ -H$]$ 715.18211 found 715.18161.

Example 98

4-(2-{1-benzhydryl-5-chloro-2-[2-({[2-(1,3-thiazolidin-3-yl)ethyl]sulfonyl}amino)ethyl]-1H-indol-3-yl}ethoxy)benzoic acid Step 1: The compound was prepared from the intermediate from Example 87 step 1 and thiazolidine according to the procedure in Example 87 step 2 except that it was refluxed overnight, in 33% yield.

Step 2: The ester intermediate was hydrolyzed according to Step 8 Example 1, except that the pH was adjusted to 4–5, to afford the title acid in 93% yield. m/z (M-1) 702.3. HRMS calc for $[C_{37}H_{38}ClN_3O_5S_2$ -H$]$ 702.18686 found 702.18659.

Example 99

4-(2-{1-benzhydryl-5-chloro-2-[2-2-[1,2,3]triazol-1-yl-ethanesulfonylamino)-ethyl]-1H-indol-3-yl}ethoxy)benzoic acid Step 1: The compound was prepared from the intermediate from Example 87 step 1 and 1H-[1,2,3]triazole according to the procedure in Example 87 step 2 except that it was refluxed for 5 days, in 23% yield.

Step 2: The ester intermediate was hydrolyzed according to Step 8 Example 1, except that the pH was adjusted to 4–5, to afford the title acid in 100% yield. m/z (M-1) 682.0. HRMS calc for $[C_{36}H34ClN_5O_5S$ -H$]$ 682.18964 found 682.18933.

Example 100

4-(3-{1-Benzhydryl-5-chloro-2-[2-(2-morpholin-4-yl-ethanesulfonylamino)-ethyl]-1H-indol-3-yl}-propyl)-benzoic acid Step 1: To methyl 4-(2-[2-(2-aminoethyl)-1-benzhydryl-5-chloro-1H-indol-3-yl]propyl}benzoate , Step 6, Example 42, (0.16M, 1.0 equiv.) and triethylamine (2.3 equiv.) in THF was added 2-chloroethanesulfonyl chloride (1.2 eq) dropwise. After 4 h the mixture was poured into brine and extracted with EtOAc. The combined organic phase was dried over magnesium sulfate and purified by column chromatography to afford the vinyl sulfonamide.

Step 2: To the product from step 1 in 1-propanol was added morpholine. After 5 h the reaction mixture was evaporated to dryness before redissolving in EtOAc. The organic phase was washed with brine, dried over magnesium sulfate, and purified by column chromatography to give the desired methyl ester in 100% yield.

Step 3: The ester intermediate was hydrolyzed according to Step 8 Example 1 to afford the title acid in 85% yield. m/z (M-1) 698.12. HRMS calc for $[C_{39}H_{42}ClN_3O_5S$ -H] 698.24609 found 698.24581.

Example 101

4-[3-(1-Benzhydryl-5-chloro-2-{2-[2-(2,6-dimethyl-piperidin-1-yl)-ethanesulfonylamino]-ethyl}-1H-indol-3-yl)-propyl]-benzoic acid Step 1: The compound was prepared from the intermediate from Example 100 step 1 and 2,6-dimethylpiperdine according to the procedure in Example 100 step 2 except that it was refluxed for heated at 80° C. for 1d17h, in 59% yield.

Step 2: The ester intermediate was hydrolyzed according to Step 8 Example 1 to afford the title acid in 86% yield. m/z (M-1) 724.20. HRMS calc for $[C_{42}H_{48}ClN_3O_4S$ -H] 724.29813 found 724.29776.

Example 102

4-[3-(1-Benzhydryl-5-chloro-2-{2-[2-(3,5-dimethyl-pyrazol-1-yl)-ethanesulfonylaminol-ethyl}-1H-indol-3-yl)-propyl]-benzoic acid Step 1: The compound was prepared from the intermediate from Example 100 step 1 and 3,5-dimethyl-1H-pyrazole according to the procedure in Example 100 step 2 except that it was refluxed for heated at 80° C. for 1 d, in quantitative yield.

Step 2- The ester intermediate was hydrolyzed according to Step 8 Example 1 to afford the title acid in 89% yield. m/z (M-1) 707.16. HRMS calc for $[C_{40}H_{41}ClN_4O_4S$ -H] 707.24642 found 707.24597.

Example 103 and 104

4-(2-{1-benzhydryl-5-chloro-2-[2-(2-tetrazol-2-yl-ethanesulfonylamino)-ethyl]-1H-indol-3-yl}ethoxy) benzoic acid and 4-(2-{1-benzhydryl-5-chloro-2-[2-(2-tetrazol-1-yl-ethanesulfonylamino)-ethyl]-1H-indol-3-yl}ethoxy) benzoic acid Step 1: The mixture of 4-2-[1-Benzhydryl-5-chloro-2-(2-ethenesulfonylamino-ethyl)-1H-indol-3-yl]-ethoxy}-benzoic acid methyl ester (0.2M, 1.0 equiv.), 1H-tetrazole (4.0 equiv.) and iPr$_2$NEt(4.3 equiv.) in 1-propanol was refluxed overnight. It was evaporated to dryness before redissolving in EtOAc. The organic phase was washed with water and brine, dried over magnesium sulfate, purified by column chromatography to give two isomers in 41% and 52% yields, respectively.

Step 2: The ester intermediates were hydrolyzed according to Step 8 Example 1, except that the pH was adjusted to 4-5, to afford the title acids 4-(2-{1-benzhydryl-5-chloro-2-[2-(2-tetrazol-2-yl-ethanesulfonylamino)-ethyl]-1H-indol-3-yl}ethoxy)benzoic acid in 92% yield. m/z (M-1) 683.3; 4-(2-{1-benzhydryl-5-chloro-2-[2-(2-tetrazol-1-yl-ethanesulfonylamino)-ethyl]-1H-indol-3-yl}ethoxy)benzoic acid in 83% yield. m/z (M-1) 683.3. HRMS calc for $[C_{35}H_{33}ClN_6O_5S$ -H] 683.18489 found 683.18458; 4-(2-{1-benzhydryl-5-chloro-2-[2-(2-tetrazol-1-yl-ethanesulfonylamino)-ethyl]-1H-indol-3-yl}ethoxy)benzoic acid in 83% yield. HRMS calc for $(C_{35}H_{33}ClN_6O_5S$-H] 683.18489 found 683.18435.

Method E

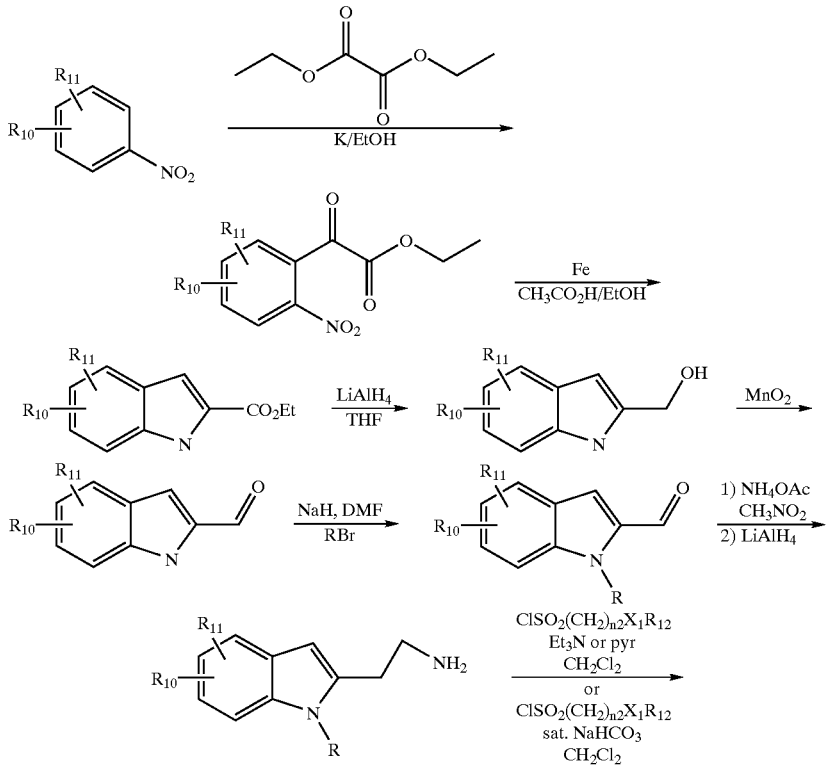

-continued

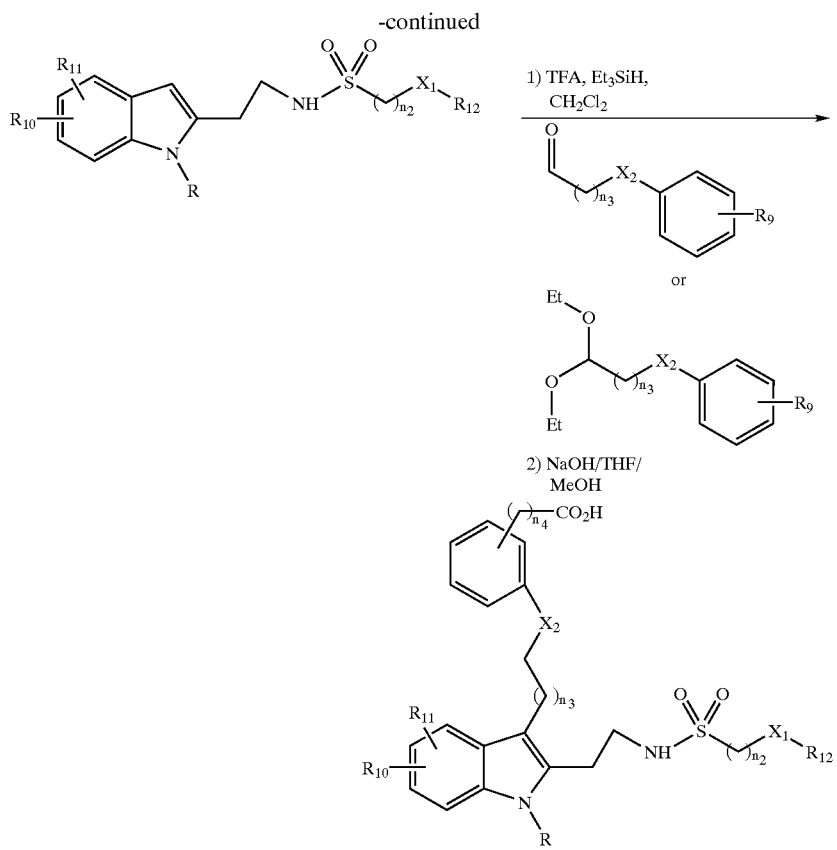

The substituted nitro aromatic was treated with ethyl oxalate in the presence of potassium or sodium in an alcoholic solvent. The resulting oxalate ester was treated with a suitable reducing agent, such as iron powder, and the resulting amine cyclized to the indole under the reaction conditions. The carboxylate was next reduced with any of a variety of reducing agents, lithium aluminum hydride, dibal etc and the resulting alcohol was oxidized using reagents such as manganese dioxide, Swern condition NMO/TPAP etc. This 2 formyl indole was next alkylated by treatment with a strong base such as Na/KHMDS, NaH, etc and then alkylated with a suitable halide. The aldehyde was next treated with nitromethane and a base such as ammonium acetate to yield a vinyl nitro intermediate that could be reduced by a variety of agents such as Lithium Aluminum Hydride or Zn(Hg) amalgam in HCl. The resulting amine was sulfonylated using a sulfonly chloride either under biphasic Schott and Baummen conditions or anhydrous conditions with an organic base. This intermediate could be reductively alkylated at C3 using an aldehyde or an acetal under the action of a Bronsted or Lewis acid such as triflouroacetic acid and a reducing agent such as triethylsilane. The reulting intermediate was hydrolyzed using a base, NaOH, KOH, LiOH and a mixture of solvents including an alcoholic solvent, water and tetrahydrofuran.

Examples 105–107 were synthesized with Method E.

Example 105

4-{2-[1-Benzhydryl-6-chloro-2-(2-phenylmethanesulfonyl amino-ethyl)-1H-indol-3-yl]-ethoxy}-benzoic acid The title compound was synthesized as depicted in Method E.

Step 1: To potassium (6.24 g) in ether at rt were added ethanol (40 mL, in 100 mL ether), diethyl oxalate (27.85 g, in 60 mL ether), and 4-chloro-2-nitrotoluene (in 40 mL ether). The reaction mixture was stirred at rt for 15 h and followed by sonication for 7 h before pouring onto cold 1N HCl. After neutralization, the aqueous layer was extracted with EtOAc and the combined organic layers were washed with brine and dried. After evaporation, the crude 3-(4-Chloro-2-nitro-phenyl)-2-oxo-propionic acid ethyl ester was used directly in the next step without further purification.

Step 2: To crude 3-(4-chloro-2-nitro-phenyl)-2-oxo-propionic acid ethyl ester (151 mmol) in ethanol:glacial HOAc (1:1, v/v, 560 mL) at rt was added iron powder (74.4 g) and the reaction mixture was stirred at reflux for 4 h. The mixture was filtered and evaporated to give a residue which was redistributed in dichloromethane/1N HCl. The organic layer was washed with 1N HCl, NaHCO$_3$, and brine and dried. Evaporation followed by crystallization (DCM) gave 6-Chloro-1H-indole-2-carboxylic acid ethyl ester as a pale yellow solid (16.8 g, 50% over 2 steps).

Step 3: To 6-chloro-1H-indole-2-carboxylic acid ethyl ester (8.57 g) in THF at 0° C. was added lithium aluminum hydride solution (1M, in THF) dropwise and the reaction mixture was stirred for 3.5 h. The mixture was quenched with H$_2$O, 15% NaOH, and H$_2$O before it was filtered and rinsed with THF. Evaporation of the solvent gave 7.77 g of the crude (6-Chloro-1H-indol-2-yl)-methanol which was used directly in the next step.

Step 4: To (6-chloro-1H-indol-2-yl)-methanol (37.7 mmol) in THF at 0° C. was added manganese (IV) oxide and the mixture was stirred at rt for 16 h. The mixture was filtered over celite and rinsed with THF and EtOAc and evaporated to near dryness. The solid was filtered and washed with cold EtOAc/hex to give 6-Chloro-1H-indole-2-carbaldehyde (62%, 2 steps).

Step 5: To 6-chloro-1H-indole-2-carbaldehyde (1 equiv.) in DMF at 0° C. was added NaH (1.25 equiv.) portionwise followed by benzhydryl bromide (1.46 equiv.) and Bu$_4$NI (0.05 equiv.). The mixture was stirred at rt for 42 h before quenching with cold 0.4N HCl at 0° C. After neutralization, the aqueous layer was extracted with ether and the organic layer was washed with cold H$_2$O and dried. Flash chromatography on silica gel gave 1-benzhydryl-6-chloro-1H-indole-2-carbaldehyde in 40% yield.

Step 6: A solution of 1-benzhydryl-6-chloro-1H-indole-2-carbaldehyde (0.5M, 1 equiv.) and NH$_4$OAc (1 equiv.) in nitromethane was heated at 95° C. for 70 min. The mixture was diluted with EtOAc, washed with water, and dried. Evaporation of the volatiles, followed by trituration with ether/hexane produced 1-Benzhydryl-6-chloro-2-(2-nitro-vinyl)-1H-indole in 48% yield.

Step 7: To lithium aluminum hydride (1M in THF, 4 equiv.) in THF at 0° C. was added 1-benzhydryl-6-chloro-2-(2-nitro-vinyl)-1H-indole (0.1M, 1 equiv.) dropwise and the reaction mixture was stirred for 2 h. The mixture was quenched with H$_2$O, 15% NaOH, and H$_2$O, filtered through celite and rinsed with EtOAc. After evaporation, the residue was purified by column chromatography to generate 2-(1-Benzhydryl-6-chloro-1H-indol-2-yl)-ethylamine in 40% yield.

Step 8: To 2-(1-Benzhydryl-6-chloro-1H-indol-2-yl)-ethylamine was added phenylmethanesulfonyl chloride according to the procedure in Example 1 Step 7 to generate N-[2-(1-Benzhydryl-6-chloro-1H-indol-2-yl)-ethyl]-C-phenyl-methanesulfonamide in 90% yield.

Step 9: To N-[2-(1-Benzhydryl-6-chloro-1H-indol-2-yl)-ethyl]-C-phenyl-methanesulfonamide (0.033M, 1 equiv.) in DCM at 0° C. were added 4-(2-oxo-ethoxy)-benzoic acid methyl ester (3.3 equiv.), triethylsilane (6 equiv.), and TFA (5 equiv.). The reaction mixture was stirred at rt for 2 d 20 h before aqueous workup. Purification by silica gel chromatography followed by reverse phase HPLC gave 4-{2-[1-Benzhydryl-6-chloro-2-(2-phenylmethanesulfonylamino-ethyl)-1H-indol-3-yl]-ethoxy}-benzoic acid methyl ester in 35% yield.

Step 10: The ester intermediate from step 9 was hydrolyzed according to Step 8 Example 1 to afford the title acid in 64% yield.

Example 106

4-(2-{1-Benzhydryl-6-chloro-2-[2-(3,4-dichloro-phenylmethanesulfonylamino)-ethyl]-1H-indol-3-yl}-ethoxy)-benzoic acid Step 1: To 2-(1-Benzhydryl-6-chloro-1H-indol-2-yl)-ethylamine, Example 105 step 7 was added (3,4-dichloro-phenyl)-methanesulfonyl chloride according to the procedure in Example 105 Step 7 to generate N-[2-(1-benzhydryl-6-chloro-1H-indol-2-yl)-ethyl]-C-(3,4-dichloro-phenyl)-methanesulfonamide in quantitative yield.

Step 2: N-[2-(1-Benzhydryl-6-chloro-1H-indol-2-yl)-ethyl]-C-(3,4-dichloro-phenyl)-methanesulfonamide was reductively alkylated as described in Example 105 step 9 to give 4-(2-{1-benzhydryl-6-chloro-2-[2-(3,4-dichloro-phenylmethanesulfonylamino)-ethyl]-1H-indol-3-yl}-ethoxy)-benzoic acid methyl ester in 38% yield.

Step 3: The ester intermediate was hydrolyzed according to Step 8 Example 1 to afford the title acid in 96% yield. m/z (M-1) 747.27.

Example 107

4-[2-{1-Benzhydryl-6-chloro-2-[2-(3,5-dichloro-phenylmethanesulfonylamino)-ethyl]-1H-indol-3-yl}-ethoxy)-benzoic acid Step 1: To 2-(1-Benzhydryl-6-chloro-1H-indol-2-yl)-ethylamine, Example 105 step 7 was added (3,5-dichloro-phenyl)-methanesulfonyl chloride according to the procedure in Example 105 Step 7 to generate N-[2-(1-benzhydryl-6-chloro-1H-indol-2-yl)-ethyl]-C-(3,5-dichloro-phenyl)-methanesulfonamide in quantitative yield.

Step 2: N-[2-(1-Benzhydryl-6-chloro-1H-indol-2-yl)-ethyl]-C-(3,4-dichloro-phenyl)-methanesulfonamide was reductively alkylated as described in Example 105 step 9 to give 4-(2-{1-benzhydryl-6-chloro-2-[2-(3,5-dichloro-phenylmethanesulfonylamino)-ethyl]-1H-indol-3-yl}ethoxy)-benzoic acid methyl ester in 31% yield.

Step 3: The ester intermediate was hydrolyzed according to Step 8 Example 1 to afford the title acid in 95% yield. m/z (M-1) 747.27.

Example 108

4-{2-[1-Benzhydryl-5-chloro-2-(2-{[(2-cyanobenzyl)sulfonyl]amino}ethyl)-1H-indol-3-yl]ethoxy}benzoic acid Step 1 The sulfonyl chloride intermediate was prepared from 2-bromomethyl-benzonitrile according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7.

Step 3: The ester intermediate was hydrolyzed according to Step 8 Example 1 to afford the title acid in 72% overall yield. HRMS calcd. for $C_{40}H_{35}ClN_3O_5S$ (M+1): 704.1980; found: 704.1984. HRMS calcd. for $C_{40}H_{35}ClN_3O_5S$ (M+1): 704.1980; found: 704.1984.

Example 109

4-{2-[1-Benzhydryl-5-chloro-2-(2-{[(tetrahydro-2H-pyran-2-ylmethyl)sulfonyl]amino}ethyl)-1H-indol-3-yl]ethoxy}benzoic acid Step 1: The sulfonyl chloride intermediate was prepared from 2-bromomethyl-tetrahydro-pyran according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7.

Step 3: The ester intermediate was hydrolyzed according to Step 8 Example 1 to afford the title acid in 20% overall yield HRMS calcd. for $C_{38}H_{38}ClN_2O_6S$ (M-1): 685.2145; found: 685.2143.

Example 110

4-{2-[1-Benzhydryl-2-(2-{[(1,3-benzoxazol-2-ylmethyl)sulfonyl]amino}ethyl)-5-chloro-1H-indol-3-yl]ethoxy}benzoic acid Step 1: The sulfonyl chloride intermediate was prepared from 2-bromomethyl-benzooxazole according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7.

Step 3: The ester intermediate was hydrolyzed according to Step 8 Example 1 to afford the title acid in 26% overall yield HRMS calcd. for $C_{40}H_{35}ClN_3O_5S$ (M+1): 720.1930; found: 720.1924.

Example 111

4-{2-[1-Benzhydryl-5-chloro-2-(2-{[(cyanomethyl) sulfonyl]amino}ethyl)-1H-indol-3-yl] ethoxy}benzoic acid Step 1: The sulfonyl chloride intermediate was prepared from 3-bromomethyl-[1,2,4]oxadiazole according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7.

Step 3: The ester intermediate was hydrolyzed according to Step 8 Example 1 to afford the title acid in 59% overall yield. HRMS calcd. for $C_{34}H_{31}ClN_3O_5S$ (M+1): 628.1668; found: 628.1662.

Example 112

4-{2-[1-Benzhydryl-5-chloro-2-(2-{[(3-thienylmethyl)sulfonyl]amino}ethyl)-1H-indol-3-yl] ethoxy}benzoic acid Step 1: The sulfonyl chloride intermediate was prepared from 3-bromomethyl 3-bromomethyl-thiophene according to the procedure in Example 18 Step 1–2 in 100% yield.

Step 2: The methyl ester was prepared from the sulfonyl chloride and methyl 4-{2-[2-(2-aminoethyl)-1-benzhydryl-5-chloro-1H-indol-3-yl]ethoxy}benzoate (Step 5, Example 1) according to the procedure in Example 1 Step 7.

Step 3: The ester intermediate was hydrolyzed according to Step 8 Example 1 to afford the title acid in 25% overall yield. HRMS calcd. for $C_{32}H_{31}ClN_2O_5S_2$ (M-1): 683.1447; found: 683.1445.

Example 113

4-[2-(1-Benzhydryl-5-chloro-2-{2-[2-(2-methyl-pyrrolidin-1-yl)-ethanesulfonylamino]-ethyl}-1H-indol-3-yl)-ethoxy]-benzoic acid Step 1: The compound was prepared from the intermediate from Example 87 step 1 and 2-methyl-pyrrolidine according to the procedure in Example 87 step 2 in 91% yield.

Step 2: The ester intermediate was hydrolyzed according to Step 8 Example 1, except that the pH was adjusted to 4–5, to afford the title acid in 99% yield. HRMS calc for $[C_{39}H_{42}ClN_3O_5S$ -H] 698.24609 found 698.24572.

Example 114

4-[2-(1-Benzhydryl-5-chloro-2-{2-[2-(2-methyl-piperidin-1-yl)-ethanesulfonylamino]-ethyl}-1H-indol-3-yl)-ethoxy]-benzoic acid Step 1: The compound was prepared from the intermediate from Example 87 step 1 and 2-methyl-piperidine according to the procedure in Example 87 step 2 in 91% yield.

Step 2: The ester intermediate was hydrolyzed according to Step 8 Example 1, except that the pH was adjusted to 4–5, to afford the title acid in 96% yield. HRMS calc for $[C_{40}H_{44}ClN_3O_5S$ -H] 712.26174 found 712.26113.

Example 115

4-[2-(1-Benzhydryl-5-chloro-2-{2-[2-(2,5-dimethyl-pyrrolidin-1-yl)-ethanesulfonylamino]-ethyl}-1H-indol-3-yl)-ethoxy]-benzoic acid Step 1: The compound was prepared from the intermediate from Example 87 step 1 and 2,5-methyl-pyrrolidine according to the procedure in Example 87 step 2 in 81% yield.

Step 2: The ester intermediate was hydrolyzed according to Step 8 Example 1, except that the pH was adjusted to 4–5, to afford the title acid in 96% yield. HRMS calc for $[C_{40}H_{44}ClN_3O_5S$ -H] 712.26174 found 712.26114.

Example 116

4-(2-{1-Benzhydryl-5-chloro-2-[2-(2-thiomorpholin-4-yl-ethanesulfonylamino)-ethyl]-1H-indol-3-yl}ethoxy)-benzoic acid Step 1: The compound was prepared from the intermediate from Example 87 step 1 and thiomorpholine according to the procedure in Example 87 step 2 in 93% yield.

Step 2: The ester intermediate was hydrolyzed according to Step 8 Example 1, except that the pH was adjusted to 4–5, to afford the title acid in 90% yield. HRMS calc for $[C_{38}H_{40}ClN_3O_5S_2$ -H] 716.20251 found 716.20217.

Example 117

4-2-{1-Benzhydryl-5-chloro-2-[2-(2-piperidin-1-yl-ethanesulfonylamino)-ethyl]-1H-indol-3-yl}-ethoxy)-benzoic acid Step 1: The compound was prepared from the intermediate from Example 87 step 1 and piperidine according to the procedure in Example 87 step 2 in 99% yield.

Step 2: The ester intermediate was hydrolyzed according to Step 8 Example 1, except that the pH was adjusted to 4–5, to afford the title acid in 92% yield. HRMS calc for $[C_{39}H_{42}ClN_3O_5S$ -H] 698.24609 found 698.24570.

Example 118

4-{2-[1-benzhydryl-5-chloro-2-(2-o-tolylsulfanylmethanesulfonylamino-ethyl)-1H-indol-3-yl]-ethoxy}-benzoic acid Step 1: To methyl 4-{2-[1-benzhydryl-5-chloro-2-(2-{[(chloromethyl)sulfonyl]amino}ethyl)-'1H-indol-3-yl]ethoxy}benzoate, Example 81 step 1, was added o-thiocresol according to the procedure in Example 81 step 2 and 3. The product was purified by the preperative HPLC in 45% yield.

Step 2: The ester intermediate was hydrolyzed according to Step 8 Example 43 to afford the title acid in 98% yield. m/z (M-1)723.07. HRMS calc for $[C_{40}H_{37}ClN_2O_5S$ -H] 723.17596 found 723.17596.

Example 119

4-{2-1-benzhydryl-5-chloro-2-[2-2-chloro-phenylsulfanylmethanesulfonylamino)-ethyl]-1H-indol-3-yl]-ethoxy)-benzoic acid Step 1: To methyl 4-{2-[1-benzhydryl-5-chloro-2-(2-{[(chloromethyl)sulfonyl]amino}ethyl)-'1H-indol-3-yl]

ethoxy}benzoate, Example 81 step 1, was added 2-chlorothiophenol according to the procedure in Example 81 step 2 and 3. The product was purified by the preperative HPLC in 53% yield.

Step 2: The ester intermediate was hydrolyzed according to Step 8 Example 43 to afford the title acid in 100% yield. m/z (M-1)743.08. HRMS calc for [$C_{39}H_{34}Cl_2N_2O_5S_2$ -H] 743.12134 found 743.12111.

Example 120

4-(2-{1-benzhydryl-5-chloro-2-[2-(2,6-dichloro-phenylsulfanylmethanesulfonylamino)-ethyl]-1H-indol-3-yl}-ethoxy)-benzoic acid Step 1: To methyl 4-{2-[1-benzhydryl-5-chloro-2-(2-{[(chloromethyl)sulfonyl]amino}ethyl)-'1H-indol-3-yl] ethoxy}benzoate, Example 81 step 1, was added 2,6-dichlorothiophenol according to the procedure in Example 81 step 2 and 3. The product was purified by the preperative HPLC in 15.7% yield and hydrolized acid in 37%.

Step 2: The ester intermediate was hydrolyzed according to Step 8 Example 43 to afford the title acid in 98% yield. m/z (M-1) 776.93. HRMS calc for [$C_{39}H_{33}Cl_3N_2O_5S_2$-H] 777.08237 found 777.08205.

Example 121

4-(2-{1-benzhydryl-5-chloro-2-[2-(2,5-dimethoxy-phenylsulfanylmethanesulfonylamino)-ethyl]-1H-indol-3-yl}-ethoxy)-benzoic acid Step 1: To methyl 4-{2-[1-benzhydryl-5-chloro-2-(2-{[(chloromethyl)sulfonyl]amino}ethyl)-'1H-indol-3-yl] ethoxy}benzoate, Example 81 step 1, was added 2,5-dimethoxythiophenol according to the procedure in Example 81 step 2 and 3. The product was purified by the flash chromatography 35% EtOAc/hexane in 65% yield.

Step 2: The ester intermediate was hydrolyzed according to Step 8 Example 43 to afford the title acid in 99.5% yield. m/z (M-1)769.18. HRMS calc for [$C_{41}H_{39}ClN_2O_7S_2$-H] 769.18144 found 769.18121.

Example 122

4-[2-(1-benzhydryl-5-chloro-2-{2-[2-(3-hydroxy-pyrrolidine-1-yl)-ethanesulfonylamino]-ethyl}-1H-indol-3-yl)-ethoxy]-benzoic acid Step 1: The compound was prepared from the intermediate from Example 87 step 1 and 3-pyrrolidinol according to the procedure in Example 87 step 2 in 90% yield without the column purification.

Step 2: The ester intermediate was hydrolyzed according to Step 8 Example 1, except that the pH was adjusted to 4–5, to afford the title acid in 84% yield. m/z (M-1)699.99. HRMS calc for [$C_{38}H_{40}ClN_3O_6S$ -H] 700.22535 found 700.22490.

Example 123

4-[2-(1-Benzhydryl-5-chloro-2-{2-[2-(4-hydroxy-piperidin-1-yl)-ethanesulfonylamino]-ethyl}-1H-indol-3-yl)-ethoxy]-benzoic acid Step 1: The compound was prepared from the intermediate from Example 87 step 1 and 4-hydroxypiperidine according to the procedure in Example 87 step 2 in 95% yield without the column purification.

Step 2: The ester intermediate was hydrolyzed according to Step 8 Example 1, except that the pH was adjusted to 4–5, to afford the title acid in 42% yield. m/z (M-1)714.03. HRMS calc for [$C_{39}H_{42}ClN_3O_6S$ -H] 714.24100 found 714.24085.

Example 124

4-[2-(1-Benzhydryl-5-chloro-2-{2-[2-(2-dimethylaminomethyl-piperidin-1-yl)-ethanesulfonylamino]-ethyl}-1H-indol-3-yl)-ethoxy]-benzoic acid Step 1: The compound was prepared from the intermediate from Example 87 step 1 and N-(2-piperidylmethyl)-dimethylamine according to the procedure in Example 87 step 2 in 90% yield without the column purification.

Step 2: The ester intermediate was hydrolyzed according to Step 8 Example 1, except that the pH was adjusted to 4–5, to afford the title acid in 71% yield. m/z (M-1)754.94. HRMS calc for [$C_{42}H_{49}ClN_4O_5S$ -H] 755.30394 found 755.30344

Example 125

4-(2-{1-Benzhydryl-5-chloro-2-[2-(2-imidazol-1-yl-ethanesulfonylamino)-ethyl]-1H-indol-3-yl}-ethoxy)-benzoic acid Step 1: The compound was prepared from the intermediate from Example 87 step 1 and imidazole according to the procedure in Example 87 step 2 except that it was heated at 120° C. for 4.5 days, in 87% yield.

Step 2: The ester intermediate was hydrolyzed according to Step 8 Example 1, except that the pH was adjusted to 4–5, to afford the title acid in 60% yield. m/z (M-1) 681.17. HRMS calc for [$C_{37}H_{35}ClN_4O_5S$ -H] 681.19439 found 681.19409.

Example 126

4-{3-[1-benzhydryl-5-chloro-2-{2-([(2,6-difluorobenzyl)sulfonyl]amino}ethyl)-1H-indol-3-yl]propyl}benzoic acid Step 1: The sulfonyl chloride intermediate was prepared from 2,6-difluorobenzyl bromide according to the procedure in Example 18 Step 1–2 in quantitative yield.

Step 2: The methyl ester was prepared from the sulfonyl chloride and methyl 4-{2-[2-(2-aminoethyl)-1-benzhydryl-5-chloro-1H-indol-3-yl]propyl}benzoate (Step 5, Example 1) according to the procedure in Example 1 Step 7 in 53% yield.

Step 2: The ester intermediate was hydrolyzed according to Step 8 Example 1 to afford the title acid in 92% yield. m/z (M-1)711.2. HRMS calc for [$C_{40}H_{35}ClF_2N_2O_4S$ -H] 711.19013 found 711.18965.

Example 127

4-{3-[1-benzhydryl-2-(2-{[(3,4-dichlorobenzyl) sulfonyl]amino}ethyl)-1H-indol-3-yl] propyl}benzoic acid Step 1: 2-methylindole was treated with the intermediate from Example 42 step 1 and the procedure from Example 42 step 2 to yield the desired product in 88%.

Step 2: The product from above was alkylated with benzhydryl bromide according to the procere in Example 42 step 3 to yield the product in 65%.

Step 3: The product from above was oxidized using the conditions outlined in Example 42 step 4 to yield the desired 2-formyl indole in 85% yield.

Step 4: The indole from above was subjected to the nitro aldol conditions outlined in Example 42 step 5.

Step 5: The vinyl nitro compound from above was reduced under the conditions outlined in Example 42 step 6 to yield the desired amino indole in 39% yield.

Step 6: The amine from step 5 was treated with (3,4-dichlorophenyl)-methyl]sulfonyl chloride according to the procedure in Example 43 Step 7 which yielded 100% of the desired product.

Step 7: The ester intermediate was hydrolyzed according to Step 8 Example 43 to afford the title acid in 24% yield. HRMS calc for $[C_{40}H_{36}ClN_2O_4S-H]$ 709.1700 found 709.16951.

Example 128

4-[3-(1-benzhydryl-2-{2-[(benzylsulfonyl)amino]ethyl}-1H-indol-3-yl)propyl]benzoic acid Step 1: This compound was prepared from the intermediate in Example 127 step 5 ¤-toluenesulfonyl chloride according to the procedure in Example 43 Step 7 which yielded 83% of the desired product.

Step 2: The ester intermediate was hydrolyzed according to Step 8 Example 43 to afford the title acid in 95% yield. HRMS calc for $[C_{40}H_{38}N_2O_4S\ -H]$ 641.24795 found 641.24761.

Method F

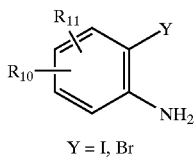

Y = I, Br

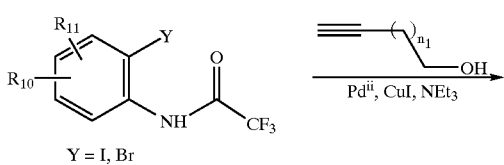

Y = I, Br

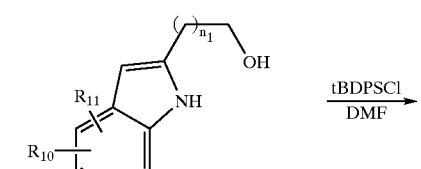

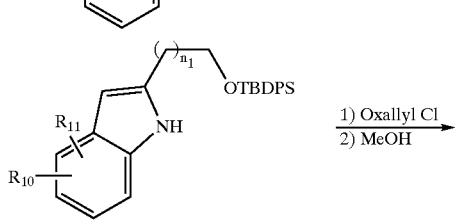

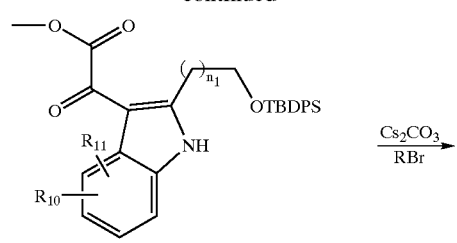

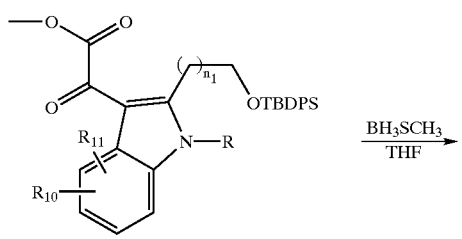

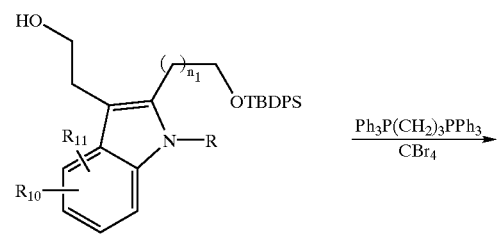

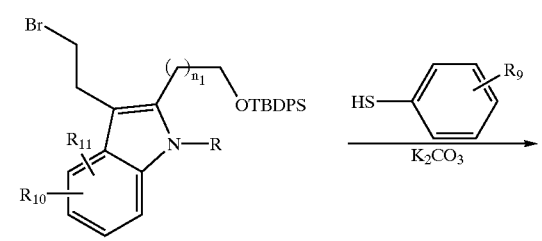

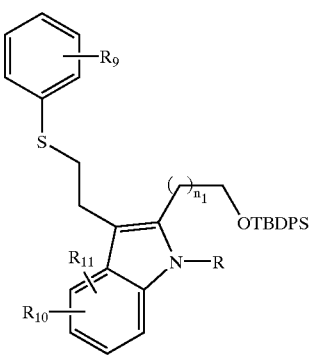

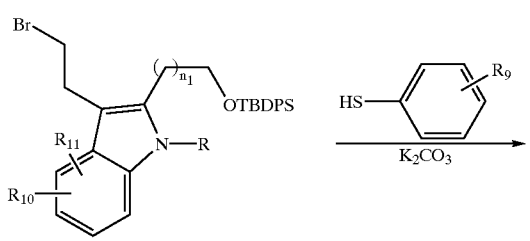

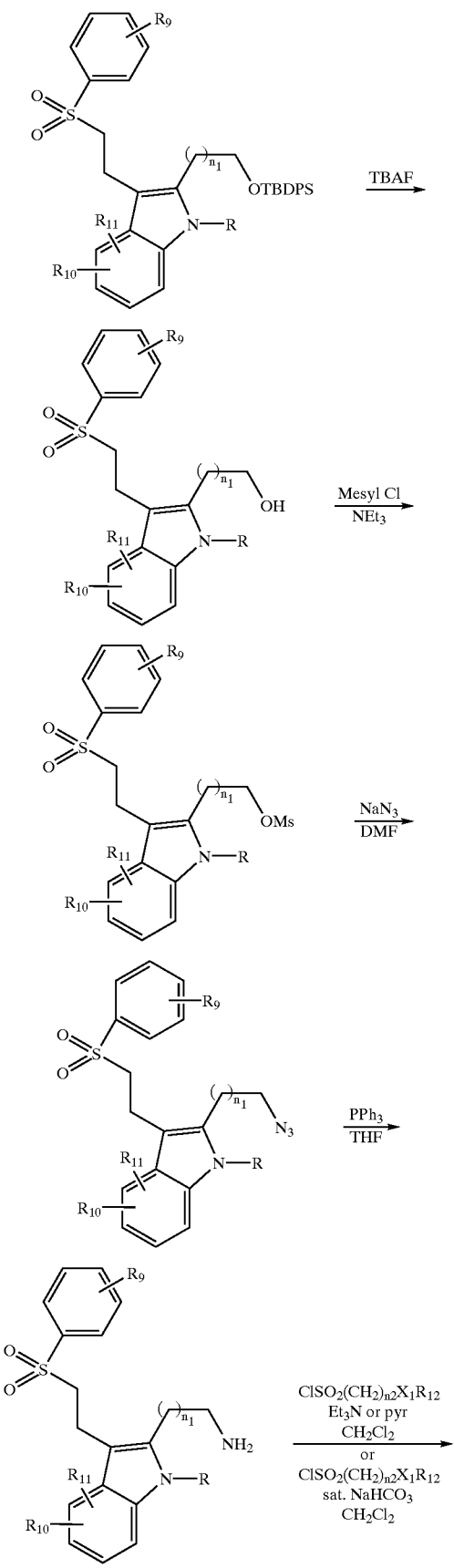

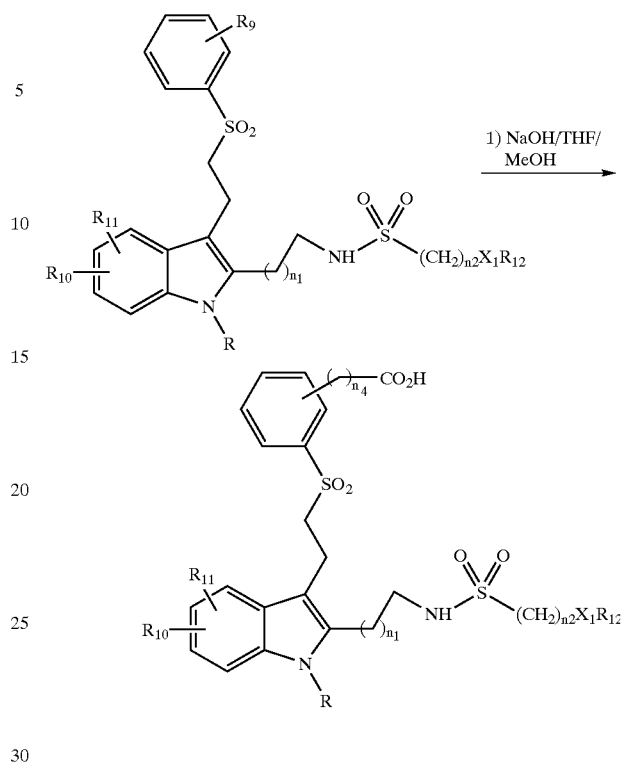

The appropriately substituted halo amine is reacted with triflouroacetic anhydride to yield an intermediate that could be treated with a $Pd^{ii}$ catalyst in the presence of a base such as triethlyamine and CuI and a suitable alkyne under heat yielded the desired indole intermediate. The primary alcohol was protected as a silyl ether using a silyl chloride such as t-Butldiphenylsilyl chloride and a base such as imidazole. The protected indole is then treated with oxallyl chloride followed by methanol which produced the desired oxalate ester which could be alkylated using a suitable base such as cesium carbonate in refluxing acetonitrile and a halide. The oxallate could then be reduced via the action of a suitable reducing agent such as borane. The resulting primary alcohol was converted to a halide, using for example $CBr_4$ and a phosphine , which could then be a nucleophile such as a thiophenol. The resulting thioether could be oxidized by a variety of oxidizing agents including oxone and TPAP/NMO. The resulting sulfone can be deprotected via the action of a flouride source such as TBAF, CsF or HF. The resulting alcohol could be converted to a halide or mesylate, for example using methane sulfonyl chloride and an organic base, which could then be displaced by sodium azide in DMF. The resulting alkyl azide could be reduced under the action of triphneyl phosphine and wet THF. The amine could be sulfonylated by the action of a sulfonyl chloride under either biphasic Shcott and Baumman conditions, Aq. Bicarbonate and dichloromethane, or under anhydrous conditions consisting of dichloromethane and an organic base such as Hunigs base. The reulting intermediate was hydrolyzed using a base, NaOH, KOH, LiOH and a mixture of solvents including an alcoholic solvent, water and tetrahydrofuran.

Example 129

3-[4-({2-[1-Benzhydryl-5-chloro-2-(2-{[(2-chlorobenzyl)sulfonyl]amino}ethyl)-1H-indol-3-yl]ethyl}sulfonyl)phenyl]propanoic acid

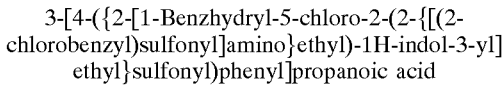

Step 1: 2-Bromo-4-chloroaniline (1.0 eq) was dissolved in $CH_2Cl_2$ (0.25M), then triethylamine and triflouroacetyl anhydride (1.1 eq each) were added. The resulting mixture was stirred at room temperature for 1 hour. Solvent was then stripped-off from the reaction mixture, and the residue was purified by flash chromatography with dichloromethane as eluent to give the described product in 97% yield. m/z(M−H)$^-$ 300.0.

Step 2: N-(2-Bromo4-chlorophenyl)-2,2,2-trifluoroacetamide(step 1, 1.0 eq) was mixed with 3-butyn-1-ol(2.0 eq), dichlorobis(triphenylphosphine)palladium (II) (2.5%eq), triethylamine(3.0 eq), CuI(5%eq) in DMF (0.2M) in a sealed vessel under $N_2$ and heated to 120° C. for 4 hours. The reaction mixture was then diluted with ethyl acetate, washed with brine and dried over $Na_2SO_4$. Furthermore, evaporate the solvent and the residue was purified by flash column chromatography with 2% MeOH/$CH_2Cl_2$ to give the described product(A) in 67% yield. m/z(M−H)$^-$ 194.09

Step 3: 2-(5-Chloro-1H-indol-2-yl)ethanol(step 2, 1.0 eq) and imidazole(2.0 eq) were dissolved in DMF(0.3M) at room temperature with stirring before tert-butylchlorodiphenylsilane (1.2eq) was added. The resulting mixture was kept stirred overnight at room temperature before it was quenched with a saturated sodium bicarbonate aqueous solution and extracted with ethyl acetate. Organic phase was washed with water and brine and dried over $Na_2SO_4$. Solvent was removed and residue was purified with column with $CH_2Cl_2$ as eluent to give the desired product as brown gum in over 90% yield. m/z(M−H)$^-$433.0.

Step 4: 2-({[tert-Butyl(diphenyl)silyl]oxy}ethyl)-5-chloro-1H-indole(step 3, 1.0 eq) was dissolved in ether (0.4M) and the solution was cooled to 0° C. Oxalyl chloride (1.2 eq) was added to the above cold solution with vigorous stirring. The reaction mixture was kept stirred at 0° C. for 1 hour before EtOH was added, followed by $NEt_3$. The resulting mixture was then diluted with more EtOH before it was poured into water. Extract with EtOAc. Organic phase washed with brine, dried over $Na_2SO_4$, concentrated to give the desired product as yellowish solid in 70% yield. m/z(M−H)$^-$533.0

Step 5: Ethyl [2-({[tert-butyl(diphenyl)silyl]oxy}ethyl)-5-chloro-1H-indol-3-yl](oxo)acetate(step 4. 1 eq), $Ph_2CHBr$ (1.5eq) and $Cs_2CO_3$(1.5eq) were mixed in dry acetonitrile (0.1M). The mixture was refluxed with stirring for 2 hours. The reaction mixture was cooled to room temperature, added water and extracted with EtOAc. Organic phase was concentrated and the residue was columned with $CH_2Cl_2$ as eluent to give the desired product as orange gum in 45% yield. m/z(M+H)$^+$701.3

Step 6: Ethyl [1-benzhydryl-2-({[tert-butyl(diphenyl)silyl]oxy}ethyl)-5-chloro-1H-indol-3-yl] (oxo)acetate(step 5, 1eq) was dissolved in THF (0.1M), then $BH_3.Me_2S$ (2M in THF) (2eq)was added to it. The resulting mixture was refluxed with stirring overnight under $N_2$. The reaction mixture was cooled to room temperature, then quenched slowly with 1N NaOH. Followed by EtOAc extraction, brine wash. Striping-off the solvent to give the described product in 65% yield. m/z(M+H)$^+$645.0

Step 7: 2-[1-Benzhydryl-2-({[tert-butyl(diphenyl)silyl]oxy}ethyl)-5-chloro-1H-indol-3-yl]ethanol (Step 6, 1 eq) was dissolved in $CH_2Cl_2$(0.08M), then 1,3-bis (diphenylphosphino)-propane (DPPP, 0.75eq) was added. The solution was cooled to 0° C. under $N_2$, then $CBr_4$ (1.25 eq) was added with stirring. The stirring was continued for 2 hours while the reaction temperature was allowed to return to room temperature. The solvent was stripped off, and the residue was purified by passing through a short column with $CH_2Cl_2$ as eluent to give the desired product in quantitative yield. m/z(M+H)$^+$708.0

Step 8: 1-Benzhydryl-3-(2-bromoethyl)-2-({[tert-butyl (diphenyl)silyl]oxy}ethyl)-5-chloro-1H-indole(Step 7, 1 eq) was mixed with methyl-3-(4-mercaptolphenyl)propionate (1.5 eq) and $K_2CO_3$ (1.5 eq) in DMF(0.1M). The resulting mixture was stirred at room temperature under $N_2$ for 2 hrs, then water was added, followed ethyl acetate extraction, brine wash, and column purification ($CH_2Cl_2$ as eluent) to give 80% of the desired product as brownish gum. m/z(M+H)823.0

Step 9: Methyl 3-[4-({2-[1-benzhydryl-2-({[tert-butyl (diphenyl)silyl]oxy}ethyl)-5-chloro-1H-indol-3-yl]ethyl}sulfanyl)phenyl]propanoate (Step 8, 1 eq) was dissolved in acetonitrile (0.1M), then molecular sieve (powder, 4 A,) and 4-methylmorpholine N-oxide (NMO)(4eq) were added under $N_2$. After 5 min, n-$Pr_4NRuO_4$ (TPAP)(5%eq) was added to it. The resulting mixture was heated to 40° C. with stirring and kept for 1.5 hrs. Strip-off the solvent, residue was columned with $CH_2Cl_2$, then 1%EtOAc/$CH_2Cl_2$ as eluent to give the desired product as white foam in 44% yield. m/z(M+H)$^+$855.1

Step 10: Methyl 3-(4-{2-[1-benzhydryl-2-({[tert-butyl (diphenyl)silyl]oxy}ethyl)-5-chloro-1H-indol-3-yl]ethoxy}phenyl)propanoate (Step 9, 1 eq) was dissolved in THF(0.1M) and cooled to 0° C., followed by $nBu_4NF$ (1M in THF) (1.2 eq). The resulting mixture was stirred at 0° C. for 5', then warmed up to room temperature and stirred for 30'. Strip-off solvent. The residue was columned with EtOAc/$CH_2Cl_2$ (1:9 to 1:4) as eluent to give the described intermediate as white foam in 90% yield. m/z(M+H)$^+$616.20

Step 11: Methyl 3-[4-{2-[1-benzhydryl-5-chloro-2-(hydroxyethyl)-1H-indol-3-yl]ethyl}sulfonyl)phenyl]propanoate(step 10, 1 eq) in dichloromethane(0.02M) was treated at 0° C. with $MeSO_2Cl$ (2.0 eq) and $Et_3N$(2.0 eq) and stirred for 1 hour. The ice-bath was removed and the reaction mixture was stirred for another 1 hour at room temperature before it was diluted with $CH_2Cl_2$, washed with $NaH_2PO_4$ brine and dried over $Na_2SO_4$. Evaporate solvent to give the described product in quantitative yield. m/z(M+H)$^+$695.0

Step 11: Methyl 3-(4-{[2-(1-benzhydryl-5-chloro-2-{2-[(methylsulfonyl}oxy]ethyl}-1H-indol-3-yl)ethyl]sulfonyl) phenyl)propanoate(step 11, 1.0 eq) was dissolved in DMF (0.03M) and treated with $NaN_3$ (3.0 eq). The resulting mixture was heated to 60° C. and stirred for 2 hours, then, was added water, extracted with ethyl acetate, washed with brine and dried with $Na_2SO_4$. Evaporation of solvent yields quantitatively the described product. m/z (M+H)$^+$641.1.

Step 12: Methyl 3-[4-({2-[2-(2-azidoethyl)-1-benzhydryl-5-chloro-1H-indol-3-yl]ethyl}sulfonyl)phenyl] propanoate(step 12, 1 eq) was dissolved in THF(0.1M), and treated with triphenylphosphine(1.1 eq). The reaction mixture was kept stirred for 2 days before the addition of water, then stirred overnight. Strip off solvent, residue was columned with 4%MeOH:CH$_2$Cl$_2$ as eluent to give the described product in 71% yield. m/z(M+H)$^+$615.2

Step 13: Methyl 3-[4-({2-[2-(2-aminoethyl)-1-benzhydryl-5-chloro-1H-indol-3-yl]ethyl}sulfonyl)phenyl] propanoate(step 12, 1 eq) and (3,4-dichlorobenzyl)sulfonyl chloride(1.1) were dissolved in CH$_2$Cl2(0.1M) at room temperature, then aqueous Na$_2$CO$_3$ solution was added with stirring. The stirring was continued for 2 hours. Then, organic phase was separated, washed with brine, dried with Na$_2$SO$_4$. Evaporate the solvent, the residue was columned with CH$_2$Cl$_2$ to 2%MeOH: CH$_2$Cl$_2$ as eluent to give 85% yield of the described product as white solid. m/z(M-H)$^-$ 834.9

Step 14: Methyl 3-[4-({2-[1-benzhydryl-5-chloro-2-(2-{[(3,4-dichlorobenzyl)sulfonyl]amino}ethyl)-1H-indol-3-yl] ethyl}sulfonyl)phenyl]propanoate (step 13, 1.0 eq) was dissolved in THF:MeOH (1:1) (0.1M), then added 1N NaOH. The mixture was kept stirred overnight at room temperature. The solvent was stripped off and the residue was dissolved in water to form a basic solution, which was neutralized with diluted HCl solution to precipitate the product. The solid was collected by filtration, washed with water, rinsed with hexane, then dried to give the desired product in 86% yield. m/z(M-H)$^-$820.9

Example 130

3-(4-{([2-(1-Benzhydryl-2-{2-[(benzylsulfonyl) amino]ethyl}-5-chloro-1H-indol-3-yl)ethyl] sulfonyl}phenyl)propanoic acid Step 1: The intermediate from example 129, step 12 was treated with ¤-toluenesulfonyl chloride according to the procedure in example 129 step 13 to yield the desired compound in 94% yield.

Step 2: The intermediate from above was treated with NaOH according to the procedure described in example 129, step 13 to yield the desired acid in 92%%.

Example 131

3-[4-({2-[1-benzhydryl-5-chloro-2-(2-{[(2,6-difluorobenzyl) sulfonyl]amino}ethyl)-1H-indol-3-yl]ethyl}sulfonyl)phenyl]propanoic acid Step 1: The intermediate from example 129, step 12 was treated with (2,6-Difluoro-phenyl)-methanesulfonyl chloride according to the procedure in example 129 step 13 to yield the desired compound in 42% yield.

Step 2: The intermediate from above was treated with NaOH according to the procedure described in example 129, step 13 to yield the desired acid in 83%%.

Example 132

3-[4-({2-[1-benzhydryl-5-chloro-2-(2-{[(2-fluorobenzyl) sulfonyl]amino}ethyl)-1H-indol-3-yl] ethyl}sulfonyl)phenyl] propanoic acid Step 1: The intermediate from example 129, step 12 was treated with (2-fluoro-phenyl)-methanesulfonyl chloride according to the procedure in example 129 step 13 to yield the desired compound in 42% yield.

Step 2: The intermediate from above was treated with NaOH according to the procedure described in example 129, step 13 to yield the desired acid in 86%%.

Method G

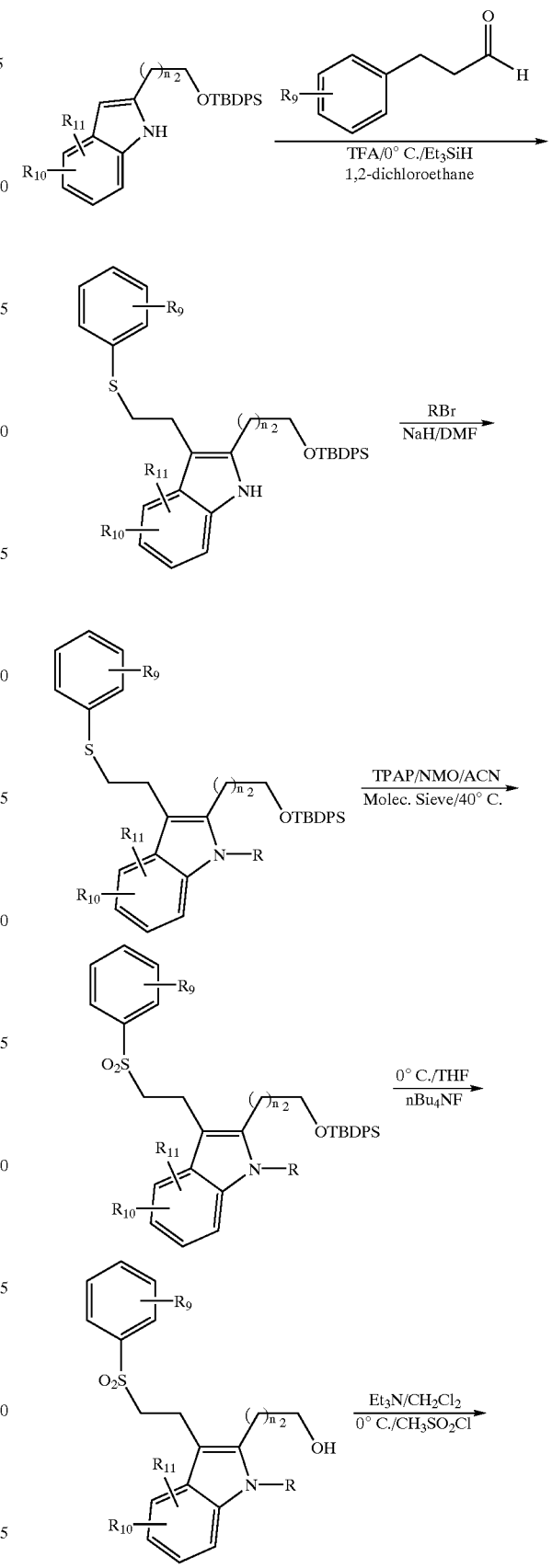

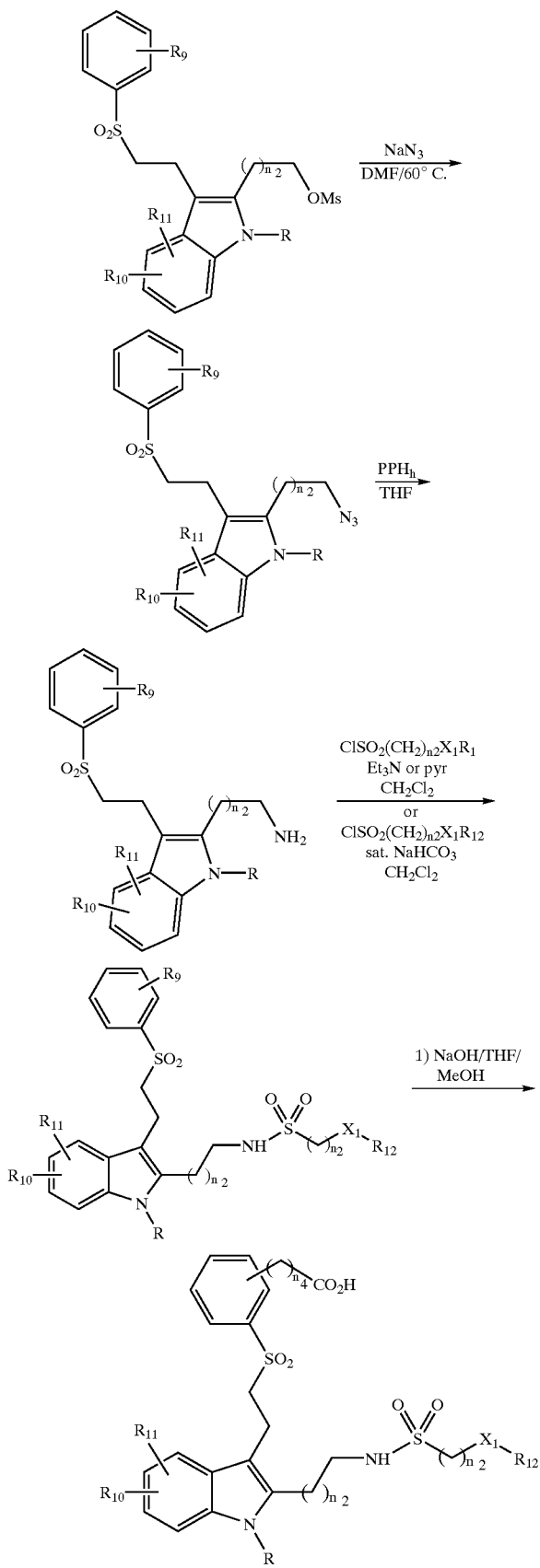

An intermediate from Method F could be alkylated at the C3 position with aldehydes or the corresponding acetals in the presence of a Lewis or Bronsted acid, such as boron triflouride etherate or triflouroacetic acid. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate halide. The resulting thioether could be oxidized by a variety of oxidizing agents including oxone and TPAP/NMO. The resulting sulfone can be de protected via the action of a flouride source such as TBAF, CsF or HF. The resulting alcohol could be converted to a halide or mesylate, for example using methane sulfonyl chlroide and an organic base, which could then be displaced by sodium azide in DMF. The resulting alkyl azide could be reduced under the action of triphneyl phosphine and wet THF. The amine could be sulfonylated by the action of a sulfonyl chloride under either biphasic Shcott and Baumman conditions, Aq. Bicarbonate and dichloromethane, or under anhydrous conditions consisting of dichloromethane and an organic base such as Hunigs base. The reulting intermediate was hydrolyzed using a base, NaOH, KOH, LiOH and a mixture of solvents including an alcoholic solvent, water and tetrahydrofuran.

The following examples were synthesized with Method G: Examples 133, 135–138,140–141.

Example 133

3-[4-({2-[1-benzhydryl-5-chloro-2-(2-{[(2-chlorobenzyl)sulfonyl]amino}ethyl)-1H-indol-3-yl]ethyl}sulfonyl)phenyl]propanoic acid The title compound was synthesized as depicted in Scheme G.

Step 1: Ethyl 4-[(2-oxoethyl)sulfanyl]propanoate (example 129 step 3, 4.2 eq) was added to a solution containing 2-({[tert-butyl(diphenyl)silyl]oxy}ethyl)-5-chloro-1H-indole (1 eq), TFA (3 eq), and 1,2-dichloroethane (0.1M) at 0° C. under $N_2$. Then $Et_3SiH$ (12 eq) was added and the reaction was allowed to return to room temperature and stirred overnight. Quenched reaction with $NaHCO_{3(aq)}$ and extracted with EtOAc and washed with brine and dried over sodium sulfate. Purified with silica gel column and 1:5 EtOAc/Hexane as eluent. Obtained ethyl 4-({2-[2-(2-{[tert-butyl(diphenyl)silyl]oxy}ethyl)-5-chloro-1H-indol-3-yl]ethyl}sulfanyl)propanoate (yellow oil) in 79% yield.

Step 2: Ethyl 4-({2-[2-(2-{[tert-butyl(diphenyl)silyl]oxy}ethyl)-5-chloro-1H-indol-3-yl]ethyl}sulfanyl)propanoate (1 eq) was added to a suspension of NaH (1.1 eq) in DMF (0.38M) at 0° C. under $N_2$. After 30 minutes $Ph_2CHBr$ was added and the reaction was warmed to room temperature. After 2.5 hours the reaction was quenched with $NH_4Cl_{(aq)}$ and extracted with EtOAc/$Et_2O$ mix and washed with water and brine and dried over sodium sulfate. Purified with silica gel column and 1:6 EtOAc/Hexane. Obtained ethyl 3-[4-({2-[1-benzhydryl-2-(2-{[tert-butyl(diphenyl)silyl]oxy}ethyl)-5-chloro-1H-indol-3-yl]ethyl}sulfanyl)phenyl]propanoate (yellow gum) in 42% yield.

Step 3: NMO (4 eq) was added to a solution/suspension containing ethyl 3-[4-({2-[1-benzhydryl-2-(2-{[tert-butyl(diphenyl)silyl]oxy}ethyl)-5-chloro-1H-indol-3-yl]ethyl}sulfanyl)phenyl]propanoate (1 eq), ACN (0.1M), and molecular sieves (1 g/mmole of propanoate) under $N_2$. After 10 minutes TPAP (0.05 eq) was added and the mixture was heated to 40° C. After 2 hours the reaction was cooled and filtered and the filtrate was collected. Purified with silica gel column and 1:4 EtOAc/Hexane. Obtained ethyl 3-[4-({2-[1-benzhydryl-2-(2-{[tert-butyl(diphenyl)silyl]oxy}ethyl)-5-chloro-1H-indol-3-yl]ethyl}sulfonyl)phenyl]propanoate (white solid) in 86% yield.

Step 4: Tetrabutylammonium fluoride (1M in THF) (1.2 eq) was added to a solution of ethyl 3-[4-({2-[1-benzhydryl-2-(2-{[tert-butyl(diphenyl)silyl]oxy}ethyl)-5-chloro-1H-indol-3-yl]ethyl}sulfonyl)phenyl]propanoate (1 eq) and THF (0.1M) at 0° C. under $N_2$. Warmed reaction to room temperature and after 30 minutes quenched with $NH_4Cl_{(aq)}$. Extracted with EtOAc and washed with brine and dried over sodium sulfate. Purified with silica gel column and 1:9 EtOAc/$CH_2Cl_2$. Obtained ethyl 3-[4-({2-[1-benzhydryl-5-chloro-2-(2-hydroxyethyl)-1H-indol-3-yl]ethyl}sulfonyl)phenyl]propanoate (white solid) in 88% yield.

Step 5: $CH_3SO_2Cl$ (2 eq) and $Et_3N$ (2.5 eq) were added to a solution of ethyl 3-[4-({2-[1-benzhydryl-5-chloro-2-(2-hydroxyethyl)-1H-indol-3-yl]ethyl}sulfonyl)phenyl]propanoate (1 eq) in $CH_2Cl_2$ (0.02M) at 0° C. under $N_2$. After 1 hour the reaction was warmed to room temperature. After an additional hour water was added and extracted with $CH_2Cl_2$ and washed with brine and dried over sodium sulfate. Removed solvent to obtain ethyl 3-(4-{[2-(1-benzhydryl-5-chloro-2-{2-[(methylsulfonyl)oxy]ethyl}-1H-indol-3-yl)ethyl]sulfonyl}phenyl)propanoate (white solid) in 98% yield.

Step 6: Ethyl 3-(4-{[2-(1-benzhydryl-5-chloro-2-{2-[(methylsulfonyl)oxy]ethyl}-1H-indol-3-yl)ethyl]sulfonyl}phenyl)propanoate (1 eq), sodium azide (5 eq), and DMF (0.05M) were placed together under $N_2$ and heated to 60° C. After 1 hour the reaction was cooled and water was added. Extracted with EtOAc/$Et_2O$ mix and washed with water and brine and dried over sodium sulfate. Removed solvent to obtain ethyl 3-[4-({2-[2-(2-azidoethyl)-1-benzhydryl-5-chloro-1H-indol-3-yl]ethyl}sulfonyl)phenyl]propanoate (light-brown solid) in 96% yield.

Step 7: Ethyl 3-[4-({2-[2-(2-azidoethyl)-1-benzhydryl-5-chloro-1H-indol-3-yl]ethyl}sulfonyl)phenyl]propanoate (1 eq), $PPh_3$ (polymer supported) (1.3 eq), and THF (0.1M) were placed together under $N_2$. After 3 days water (1 ml/1 mmole propanoate) was added and reaction was stirred overnight. Filtered and collected filtrate. Purified with silica gel column and 2% MeOH in $CH_2Cl_2$. Obtained ethyl 3-[4-({2-[2-(2-aminoethyl)-1-benzhydryl-5-chloro-1H-indol-3-yl]ethyl}sulfonyl)phenyl]propanoate (light-brown solid) in 65% yield.

Step 8: (2-chlorobenzyl)sulfonyl chloride (2.2 eq) was added to a mixture of ethyl 3-[4-({2-[2-(2-aminoethyl)-1-benzhydryl-5-chloro-1H-indol-3-yl]ethyl}sulfonyl)phenyl]propanoate (1 eq), $CH_2Cl_2$ (0.08M), water (1 mL/1 mL $CH_2Cl_2$), and $Na_2CO_3$ (2.5 eq). After 2 hours more (2-chlorobenzyl)sulfonyl chloride (1.1 eq) was added. After an additional 1.5 hours the organic layer was recovered and washed with brine and dried over sodium sulfate. Purified with silica gel preparatory plate and 2% MeOH in $CH_2Cl_2$. Obtained ethyl 3-[4-({2-[1-benzhydryl-5-chloro-2-(2-{[(2-chlorobenzyl)sulfonyl]amino}ethyl)-1H-indol-3-yl]ethyl}sulfonyl)phenyl]propanoate (light-yellow gum) in 75% yield.

Step 9: Ethyl 3-[4-({2-[1-benzhydryl-5-chloro-2-(2-{[(2-chlorobenzyl)sulfonyl]amino}ethyl)-1H-indol-3-yl]ethyl}sulfonyl)phenyl]propanoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 3-[4-({2-[1-benzhydryl-5-chloro-2-(2-{[(2-chlorobenzyl)sulfonyl]amino}ethyl)-1H-indol-3-yl]ethyl}sulfonyl)phenyl]propanoic acid (light-brown solid) in 83% yield.

Method H

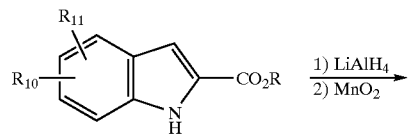

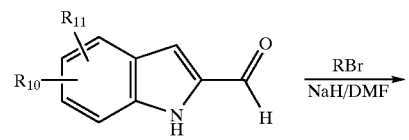

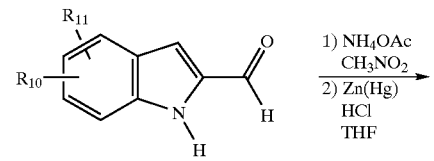

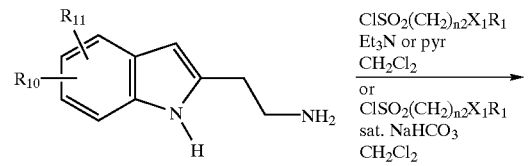

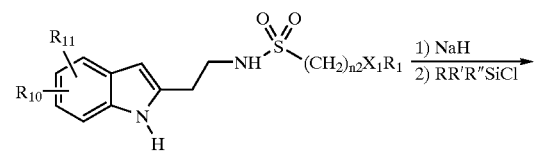

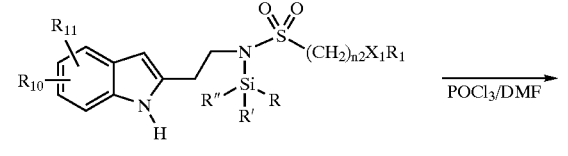

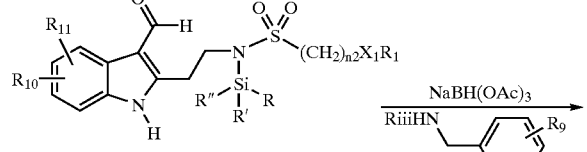

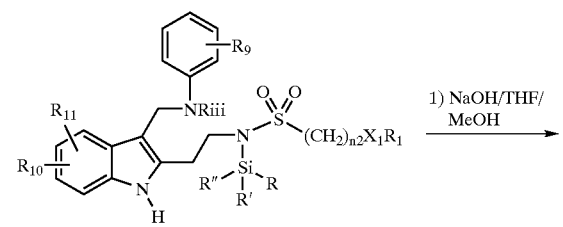

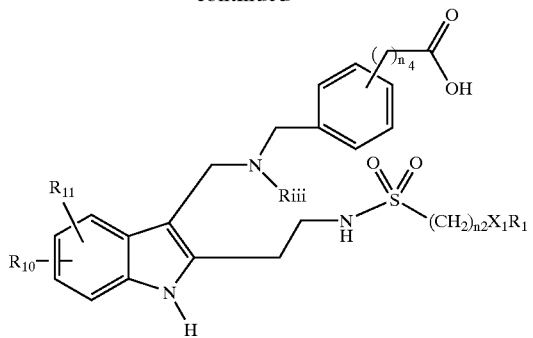

The suitably substituted indole-2-carboxylate could be reduced via a suitable reducing agent such as lithium aluminum hydride, dibal etc and then the resulting alcohol could be oxidized to the 2-formyl indole using $MnO_2$, under Swern oxidation conditions or other oxidants. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate halide. The aldehyde was next treated with nitromethane and a base such as ammonium acetate to yield a vinyl nitro intermediate that could be reduced by a variety of agents such as Lithium Aluminum Hydride or Zn(Hg) amalgam in HCl. The resulting amine was sulfonylated using a sulfonyl chloride either under biphasic Schott and Baummen conditions or anhydrous conditions with an organic base. Treatment of the resulting sulfonamide with a strong base such as sodium bis(trimethylsilyl)amide, n-BuLi, sodium hydride or potassium hydride in a solvent such as DMF, DMSO or THF followed by exposure to a silyl chloride such as t-butyldimethyl silyl chloride to generate the protected sulfonamide. This material could be formylated at C3 using standard Vilsmeier conditions conditions of $POCl_3$/DMF. The thus formed 3-formyl indole was reductively aminated using a suitable amine, a reducing agent such as sodium triacetoxyborohydride and acid such as glacial acetic acid. The reulting intermediate was hydrolyzed using a base, NaOH, KOH, LiOH and a mixture of solvents including an alcoholic solvent, water and tetrahydrofuran.

The following examples were synthesized with Method H: Examples 134.

Example 134

4-({[(1-benzhydryl-2-{2-[(benzylsulfonyl)amino] ethyl}-5-chloro-1H-indol-3-yl)methyl] amino}methyl)benzoic acid Step 1: 5-Chloro-1H-indole-2-carboxylic acid ethyl ester (1 eq.) was dissolved in THF (0.4M), flushed with a nitrogen atmosphere and then the mixture was cooled to 0° C. and LAH (3 eq of a 1M solution in THF) was slowly added. The reaction was allowed to warm slowly to room temperature and stirred until TLC analysis indicated completion. After cooling the flask to 0° C., NaOH (60 ml 3N solution) was slowly added and the reaction stirred until two layers were obtained. The layers were separated, aqueous was extracted 2X ethyl acetate, the combine organics were washed with brine and then dried over magnesium sulfate and concentrated to yield the desired alcohol that was used crude for the next step.

Step 2: The product (1 eq.) from above was dissolved in THF (0.5M) and treated with mangense dioxide (3 eq), and stirred for 1.5 hours until TLC analysis indicated that reaction was complete. The reaction was filtered through celite, dried over magnesium sulfate, and concentrated to yield the desired crude aldehyde in 82% yield.

Step 3: To the indole from above (1.0 eq) in DMF (0.36M) at 25° C. was added NaH (1.2 eq, 60% dispersion in oil), and the brown solution was stirred at 0 to –5° C. for 1 h and then bromodiphenylmethane was added (1.1 eq), and then the reaction mixture was stirred overnight. It was then quenched with water, diluted with ethyl acetate, washed with water and brine, dried over sodium sulfate and purified by column chromatography to yield 60% of the desired product.

Step 4: To the above aldehyde (1.0 equiv) in $CH_3NO_2$ (0.075M) was added ammonium acetate (9 equiv) and the resulting mixture was heated to reflux overnight. The reaction mixture concentrated to a small volume and then diluted with EtOAc and washed with brine. The aqueous phase was extracted with EtOAc. The combined organic extracts were washed with brine, dried over sodium sulfate and concentrated and purification by column chromatography to the desired nitroolefin (51% yield).

Step 5: Zinc dust (20 equiv) was suspended in 5% aqueous HCl solution (8M Zn/5% HCl). To this mixture was added $HgCl_2$ (0.28 equiv). The mixture was shaken for 10 min, the aqueous phase was decanted and replaced with fresh 5% HCl, and again the mixture was shaken for 5 min and the aqueous phase was removed. The zinc-mercury amalgam thus generated was then added to a mixture of the nitroolefin (1.0 equiv) and conc. HCl (80 equiv) in THF (0.04M nitroolefin/THF). The mixture was maintained at a gentle reflux for 1 h. The formation of product was followed by TLC analysis. The mixture was cooled to room temperature and the solids were removed by filtration through Celite. Conc. $NH_4OH$ was added to the solution phase and the mixture was concentrated on the rotary evaporator. The residue was dissolved in $CH_2Cl_2$ and conc. $NH_4OH$. The aqueous phase was extracted with $CH_2Cl_2$, and the organic phase was washed with brine, dried over sodium sulfate, and concentrated to yield the desired crude amine(100%) that was used in the next step without purification.

Step 7: To the amine form above (1.0 equiv) and sat. $NaHCO_3$ (0.14M) in $CH_2Cl_2$ (0.07M) was added ¤-toluenesulfonyl chloride (1.0 equiv). After 1 h the mixture was poured into saturated sodium bicarbonate and extracted with $CH_2Cl_2$. The combined organic phase was washed with brine, dried over sodium sulfate and purified by column chromatography (gradient elution using 10% EtOAc-hexanes → 20% EtOAc-hexanes) to afford 40% of the desired sulfonamide.

Step 8: The sulfonamide from above was dissolved in DMF (0.5M) under nitrogen atmosphere, cooled to 0° C., treated with sodium hydride (1.05 eq of a 60 oil dipersion), stirred for 15 minutes to ensure anion generation, treated with t-butyldimethsilyl chloride (1.2 eq) and then stirred for twp hours at 0° C. at which time TLC analysis indicated the reaction was complete. The reaction was worked up by partitioning between ½ saturated ammonium chloride solution and ethyl acetate, extraction of the aqueous layers with ethyl acetate (2X), washing combined organic layers with brine (1X), drying over magnesium sulfate and concentrating to yield quantitative crude yield of the desired protected sulfonamide.

Step 9: To DMF (~1 ml) was added phosporous oxychloride (1.2 eq), these reagents were stirred for 10 minutes and then a solution of the indole (1 eq) from above in DMF (0.8M) was added. The resulting red reaction mixture is stirred for 4 hours, diluted with water and then the pH was adjusted to 8 (total volume of aqueous added about % of DMF added initially) and then the reaction was refluxed for 2 hours and finally cooled, extracted with dicloromethane, aqueous layer extracted with dichloromethane (2X), combined organic layers washed with brine (1X), dried over magnesium sulfate and concentrated to yield 75% of a crude aldehyde that was used without further purification.

Step 10: To the aldehyde from above (1 eq) in THF (1.2 M) was added 4-aminomethyl-benzoic acid methyl ester (1.2 eq), sodium triacetoxyborohydride (1.5 eq) and acetic acid ( glacial, 1.5 eq). The reaction was stirred overnight and then worked up by the addition of saturated sodium bicarbonate and ethyl acetate, the layers were separated,.the aqueous layer extracted with dichloromethane (2X), combined organic layers washed with brine (1X), dried over magnesium sulfate and concentrated and purified via chromatography to yield 37% of the desired product.

Step 11: The resulting ester was hydrolyzed by stirring with 1N NaOH (5 equiv) in THF (0.07M) and enough MeOH to produce a clear solution. The reaction was monitored by TLC (10% MeOH-$CH_2Cl_2$) for the disappearance of starting material. The mixture was stirred at room temperature for 72 hours. The mixture was concentrated, diluted with $H_2O$, and acidified to pH 5 using 1M HCl. The aqueous phase was extracted with EtOAc and the organic phase was washed with brine, dried over sodium sulfate, and concentrated to afford the desired product in 83% yield. HRMS calc for [$C_{39}H_{36}ClN_3O_4S$ -H] 676.20423 found 676.20397.

Example 135

4-{[2-1-benzhydryl-2-{2-[(benzylsulfonyl)amino] ethyl}-5-chloro-1H-indol-3yl)ethyl]sulfonyl}benzoic acid Step 1: 2-(5-chloro-1H-indol-2-yl)ethanol (1 eq).was added to a solution (under $N_2$) containing tert-Butyldiphenylchlorosilane (1.2 eq), imidazole (2.5 eq), and DMF (1.8M). The reaction was stirred overnight. Quenched with $NaHCO_{3\ (aq)}$ and extracted with a $Et_2O$/EtOAc mixture. The organic layer was washed with water and brine and dried over sodium sulfate. Purified with silica gel column and 1:4 Hexane/$CH_2Cl_2$ as eluent. Obtained 2-({[tert-butyl (diphenyl)silyl]oxy}ethyl)-5-chloro-1H-indole (yellow oil) in 98% yield.

Step 2: Methyl 4-[(2-oxoethyl)sulfanyl]benzoate (3.7 eq) was added to a solution containing 2-({[tert-butyl(diphenyl) silyl]oxy}ethyl)-5-chloro-1H-indole (1 eq), TFA (3 eq), and 1,2-dichloroethane (0.1M) at 0° C. under $N_2$. Then $Et_3SiH$ (12 eq) was added and the reaction was allowed to return to room temperature and stirred overnight. Quenched reaction with $NaHCO_3$(aq) and extracted with EtOAc and washed with brine and dried over sodium sulfate. Purified with silica gel column and 1:5 EtOAc/Hexane as eluent. Obtained methyl 4-({2-[2-(2-{[tert-butyl(diphenyl)silyl]oxy}ethyl)-5-chloro-1H-indol-3-yl]ethyl}sulfanyl)benzoate (yellow solid) in 79% yield.

Step 3: Methyl 4-({2-[2-(2-{[tert-butyl(diphenyl)silyl] oxy}ethyl)-5-chloro-1H-indol-3-yl]ethyl}sulfanyl)benzoate (1 eq) was added to a suspension of NaH (1.1 eq) in DMF (0.37M) at 0° C. under $N_2$. After 30 minutes $Ph_2CHBr$ (1.8 eq) was added and the reaction was warmed to room temperature. After 3 hours the reaction was quenched with $NH_4Cl_{(aq)}$ and extracted with EtOAc/$Et_2O$ mix and washed with water and brine and dried over sodium sulfate. Purified with silica gel column and 1:5 EtOAc/Hexane. Obtained methyl 3-[4-({2-[1-benzhydryl-2-(2-{[tert-butyl(diphenyl) silyl]oxy}ethyl)-5-chloro-1H-indol-3-yl]ethyl}sulfanyl) phenyl]benzoate (yellow gum) in 65% yield.

Step 4: NMO (4 eq) was added to a solution/suspension containing methyl 3-[4-({2-[1-benzhydryl-2-(2-{[tert-butyl (diphenyl)silyl]oxy}ethyl)-5-chloro-1H-indol-3-yl] ethyl}sulfanyl)phenyl]benzoate (1 eq), ACN (0.1M), and molecular sieves (1 g/mmole of benzoate) under $N_2$. After 10 minutes TPAP (0.12 eq) was added and the mixture was heated to 40° C. After 1.5 hours the reaction was cooled and filtered and the filtrate was collected. Purified with silica gel column and 1:5 EtOAc/Hexane. Obtained methyl 3-[4-({2-[1-benzhydryl-2-(2-{[tert-butyl(diphenyl)silyl]oxy}ethyl)-5-chloro-1H-indol-3-yl]ethyl}sulfonyl)phenyl]benzoate (white solid) in 71% yield.

Step 5: Tetrabutylammonium fluoride (1M in THF) (1.2 eq) was added to a solution of methyl 3-[4-({2-[1-benzhydryl-2-(2-{[tert-butyl(diphenyl)silyl]oxy}ethyl)-5-chloro-1H-indol-3-yl]ethyl}sulfonyl)phenyl]benzoate (1 eq) and THF (0.1M) at 0° C. under $N_2$. Warmed reaction to room temperature and after 1 hour quenched with $NH_4Cl_{(aq)}$. Extracted with EtOAc and washed with brine and dried over sodium sulfate. Purified with silica gel column and 1:9 EtOAc/$CH_2Cl_2$. Obtained methyl 3-[4-({2-[1-benzhydryl-5-chloro-2-(2-hydroxyethyl)-1H-indol-3-yl]ethyl}sulfonyl) phenyl]benzoate (white solid) in 86% yield.

Step 6: $CH_3SO_2Cl$ (2 eq) and $Et_3N$ (2.5 eq) were added to a solution of methyl 3-[4-({2-[1-benzhydryl-5-chloro-2-(2-hydroxyethyl)-1H-indol-3-yl]ethyl}sulfonyl)phenyl] benzoate (1 eq) in $CH_2Cl_2$ (0.02M) at 0° C. under $N_2$. After 1 hour the reaction was warmed to room temperature. After an additional hour water was added and extracted with $CH_2Cl_2$ and washed with brine and dried over sodium sulfate. Removed solvent to obtain methyl 3-(4-{[2-(1-benzhydryl-5-chloro-2-{2-[(methylsulfonyl)oxy]ethyl}-1H-indol-3-yl)ethyl]sulfonyl}phenyl)benzoate (light-yellow solid) in 99% yield.

Step 7: Methyl 3-(4-{[2-(1-benzhydryl-5-chloro-2-{2-[(methylsulfonyl)oxy]ethyl}-1H-indol-3-yl)ethyl] sulfonyl}phenyl)benzoate (1 eq), sodium azide (5 eq), and DMF (0.05M) were placed together under $N_2$ and heated to 60° C. After 1 hour the reaction was cooled and water was added. Extracted with EtOAc/$Et_2O$ mix and washed with water and brine and dried over sodium sulfate. Removed solvent to obtain methyl 3-[4-({2-[2-(2-azidoethyl)-1-benzhydryl-5-chloro-1H-indol-3-yl]ethyl}sulfonyl)phenyl] benzoate (light-yellow solid) in 99% yield.

Step 8: Methyl 3-[4-({2-[2-(2-azidoethyl)-1-benzhydryl-5-chloro-1H-indol-3-yl]ethyl}sulfonyl)phenyl]benzoate (1 eq), $PPh_3$ (2 eq), and THF (0.1M) were placed together under $N_2$ and stirred overnight. Water (1 mL/1 mmole benzoate) was added and reaction was again stirred overnight. The solution was concentrated and purified with silica gel column and 3:1 EtOAc/Hexane followed by 5% MeOH in $CH_2Cl_2$. Obtained methyl 3-[4-({2-[2-(2-aminoethyl)-1-benzhydryl-5-chloro-1H-indol-3-yl]ethyl}sulfonyl)phenyl] benzoate (light-yellow solid) in 99% yield.

Step 9: alpha-Toluene sulfonyl chloride (2 eq) was added to a mixture of methyl 3-[4-({2-[2-(2-aminoethyl)-1-benzhydryl-5-chloro-1H-indol-3-yl]ethyl}sulfonyl)phenyl] benzoate (1 eq), $CH_2Cl_2$ (0.08M), water (1 mL/1 mL $CH_2Cl_2$), and $Na_2CO_3$ (2.5 eq). After 2 hours the organic layer was recovered and washed with brine and dried over sodium sulfate. Purified with silica gel preparatory plate and 3% MeOH in $CH_2Cl_2$. Obtained methyl 4-{[2-(1-benzhydryl-2-{2-[(benzylsulfonyl)amino]ethyl}-5-chloro-1H-indol-3-yl)ethyl]sulfonyl}benzoate (off-white solid) in 94% yield.

Step 10: Methyl 4-{[2-(1-benzhydryl-2-{2-[(benzylsulfonyl)amino]ethyl}-5-chloro-1H-indol-3-yl)ethyl]sulfonyl}benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-{[2-(1-benzhydryl-2-{2-[(benzylsulfonyl)amino]ethyl)-5-chloro-1H-indol-3-yl)ethyl]sulfonyl}benzoic acid (off-white solid) in 92% yield.

Example 136

4-{2-[1-benzhydryl-5-chloro-2-(2-{[(2-chlorobenzyl)sulfonyl]amino}ethyl)-1H-indol-3-yl]ethyl}sulfonyl)benzoic acid Step 1: (2-chlorobenzyl)sulfonyl chloride (3.4 eq) was added to a mixture of methyl 3-[4-({2-[2-(2-aminoethyl)-1-benzhydryl-5-chloro-1H-indol-3-yl]ethyl}sulfonyl)phenyl]benzoate (Example 135, Step 8, 1 eq), $CH_2Cl_2$ (0.08M), water (1 mL/1 mL $CH_2Cl_2$), and $Na_2CO_3$ (2.5 eq). After 2 hours more (2-chlorobenzyl)sulfonyl chloride (3.4 eq) was added. After an additional 1.5 hours the organic layer was recovered and washed with brine and dried over sodium sulfate. Purified with silica gel preparatory plate and 3% MeOH in $CH_2Cl_2$. Obtained methyl 3-[4-({2-[1-benzhydryl-5-chloro-2-(2-{[(2-chlorobenzyl)sulfonyl]amino}ethyl)-1H-indol-3-yl]ethyl}sulfonyl)phenyl]benzoate (orange gum) in 40% yield.

Step 2: Methyl 3-[4-({2-[1-benzhydryl-5-chloro-2-(2-[(2-chlorobenzyl)sulfonyl]amino}ethyl)-1H-indol-3-yl]ethyl}sulfonyl)phenyl]benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-({2-[1-benzhydryl-5-chloro-2-(2-{[(2-chlorobenzyl)sulfonyl]amino}ethyl)-1H-indol-3-yl]ethyl}sulfonyl)benzoic acid (red-orange solid) in 80% yield.

Example 137

4-({2-[1-benzhydryl-5-chloro-2-(2-{[(2,6-difluorobenzyl) sulfonyl]amino}ethyl)-1H-indol-3-yl]ethyl}sulfonyl)benzoic acid Step 1: (2,6-difluorobenzyl)sulfonyl chloride (3.4 eq) was added to a mixture of methyl 3-[4-({2-[2-(2-aminoethyl)-1-benzhydryl-5-chloro-1H-indol-3-yl]ethyl}sulfonyl)phenyl]benzoate (Example 135, Step 8, 1 eq), $CH_2Cl_2$ (0.08M), water (1 mL/1 mL $CH_2Cl_2$), and $Na_2CO_3$ (2.5 eq). After 2 hours the organic layer was recovered and washed with brine and dried over sodium sulfate. Purified with silica gel preparatory plate and 3% MeOH in $CH_2Cl_2$. Obtained methyl 4-({2-[1-benzhydryl-5-chloro-2-(2-{[(2,6-difluorobenzyl)sulfonyl]amino}ethyl)-1H-indol-3-yl]ethyl}sulfonyl)benzoate (off-white solid) in 87% yield.

Step 2: Methyl 4-({2-[1-benzhydryl-5-chloro-2-(2-{[(2,6-difluorobenzyl)sulfonyl]amino}ethyl)-1H-indol-3-yl]ethyl}sulfonyl)benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-({2-[1-benzhydryl-5-chloro-2-(2-{[(2,6-difluorobenzyl)sulfonyl]amino}ethyl)-1H-indol-3-yl]ethyl}sulfonyl)benzoic acid (white-yellow solid) in 96% yield.

Example 138

4-({2-[1-benzhydryl-5-chloro-2-(2-{[(2-fluorobenzyl)sulfonyl] amino}ethyl)-1H-indol-3-yl]ethyl}sulfonyl)benzoic acid Step 1: (2-fluorobenzyl)sulfonyl chloride (3.4 eq) was added to a mixture of methyl 3-[4-({2-[2-(2-aminoethyl)-1-benzhydryl-5-chloro-1H-indol-3-yl]ethyl}sulfonyl)phenyl]benzoate (Example 135, Step 8, 1 eq), $CH_2Cl_2$ (0.08M), water (1 mL/1 mL $CH_2Cl_2$), and $Na_2CO_3$ (2.5 eq). After 2 hours the organic layer was recovered and washed with brine and dried over sodium sulfate. Purified with silica gel preparatory plate and 3% MeOH in $CH_2Cl_2$. Obtained methyl 4-({2-[1-benzhydryl-5-chloro-2-(2-{[(2-fluorobenzyl)sulfonyl]amino}ethyl)-1H-indol-3-yl]ethyl}sulfonyl)benzoate (off-white solid) in 82% yield.

Step 2: Methyl 4-({2-[1-benzhydryl-5-chloro-2-(2-{[(2-fluorobenzyl)sulfonyl]amino}ethyl)-1H-indol-3-yl]ethyl}sulfonyl)benzoate (1 eq), THF (0.1 M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-({2-[1-benzhydryl-5-chloro-2-(2-{[(2-fluorobenzyl)sulfonyl]amino}ethyl)-1H-indol-3-yl]ethyl}sulfonyl)benzoic acid (off-white solid) in 99% yield.

Example 139

4-(2-{1-Benzhydryl-5-chloro-2-[2-(2-pyrrolidin-1-yl-ethane sulfonylamino)-ethyl]-1H-indol-3-yl}-ethoxy)-benzoic acid Step 1: The compound was prepared from the intermediate from Example 87 step 1 and pyrrolidine according to the procedure in Example 87 step 2 in 92% yield without the column purification.

Step 2: The ester intermediate was hydrolyzed according to Step 8 Example 1, except that the pH was adjusted to 4–5, to afford the title acid in 92% yield. HRMS calc for $[C_{38}H_{40}ClN_3O_5S$ -H] 684.23044 found 684.23009.

Example 140

4-({2-[1-benzhydryl-5-chloro-2-(2-{[(3,4-dichlorobenzyl) sulfonyl]amino}ethyl)1H-indol-3-yl]ethyl}sulfonyl)benzoic acid Step 1: (3,4-dichlorobenzyl)sulfonyl chloride (2.1 eq) was added to a mixture of methyl 3-[4-({2-[2-(2-aminoethyl)-1-benzhydryl-5-chloro-1H-indol-3-yl]ethyl}sulfonyl)phenyl]benzoate (Example 135, Step 8, 1 eq), $CH_2Cl_2$ (0.08M), water (1 mL/1 mL $CH_2Cl_2$), and $Na_2CO_3$ (2.5 eq). After 1 hours the organic layer was recovered and washed with brine and dried over sodium sulfate. Purified with silica gel preparatory plate and 3% MeOH in $CH_2Cl_2$. Obtained methyl 4-({2-[1-benzhydryl-5-chloro-2-(2-{[(3,4-dichlorobenzyl)sulfonyl]amino}ethyl)-1H-indol-3-yl]ethyl}sulfonyl)benzoate (white solid) in 87% yield.

Step 2: Methyl 4-({2-[1-benzhydryl-5-chloro-2-(2-{[(3,4-dichlorobenzyl)sulfonyl]amino}ethyl)-1H-indol-3-yl]ethyl}sulfonyl)benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-({2-[1-benzhydryl-5-chloro-2-(2-{[(3,4-dichlorobenzyl)sulfonyl]amino}ethyl)-1H-indol-3-yl]ethyl}sulfonyl)benzoic acid (white-yellow solid) in 93% yield.

Example 141

4-({2-[1-benzhydryl-5-chloro-2-(2-{[(2,6-dimethylbenzyl) sulfonyl]amino}ethyl) 1H-indol-3-yl]ethyl}sulfonyl)benzoic acid Step 1: (2,6-methylbenzyl)sulfonyl chloride (3.0 eq, example 52, step 1) was added to a mixture of methyl 3-[4-({2-[2-(2-aminoethyl)-1-benzhydryl-5-chloro-1H-indol-3-yl]ethyl}sulfonyl)phenyl]benzoate (Example 135, Step.8, 1 eq), $CH_2Cl_2$ (0.08M), water (1 mL/1 mL $CH_2Cl_2$), and $Na_2CO_3$ (2.5 eq). After 2 hours the organic layer was recovered and washed with brine and dried over sodium sulfate. Purified with silica gel preparatory plate and 3% MeOH in $CH_2Cl_2$. Obtained methyl 4-({2-[1-benzhydryl-5-chloro-2-(2-{[(2,6-dimethylbenzyl)sulfonyl]amino}ethyl)-1H-indol-3-yl]ethyl}sulfonyl)benzoate (light-brown solid) in 81% yield.

Step 2: Methyl 4-({2-[1-benzhydryl-5-chloro-2-(2-{[(2,6-dimethylbenzyl)sulfonyl]amino}ethyl)-1H-indol-3-yl]ethyl}sulfonyl)benzoate (1 eq), THF (0.1M), MeOH (1 mL/1 mL THF), and NaOH (1N) (11 eq) were stirred together overnight. Solvents were removed and the resulting residue was taken up in water. The solution was acidified with 1N HCl and collected resulting precipitate by filtration. Obtained 4-({2-[1-benzhydryl-5-chloro-2-(2-{[(2,6-dimethylbenzyl)sulfonyl]amino}ethyl)-1H-indol-3-yl]ethyl}sulfonyl)benzoic acid (white solid) in 99% yield.

Method J

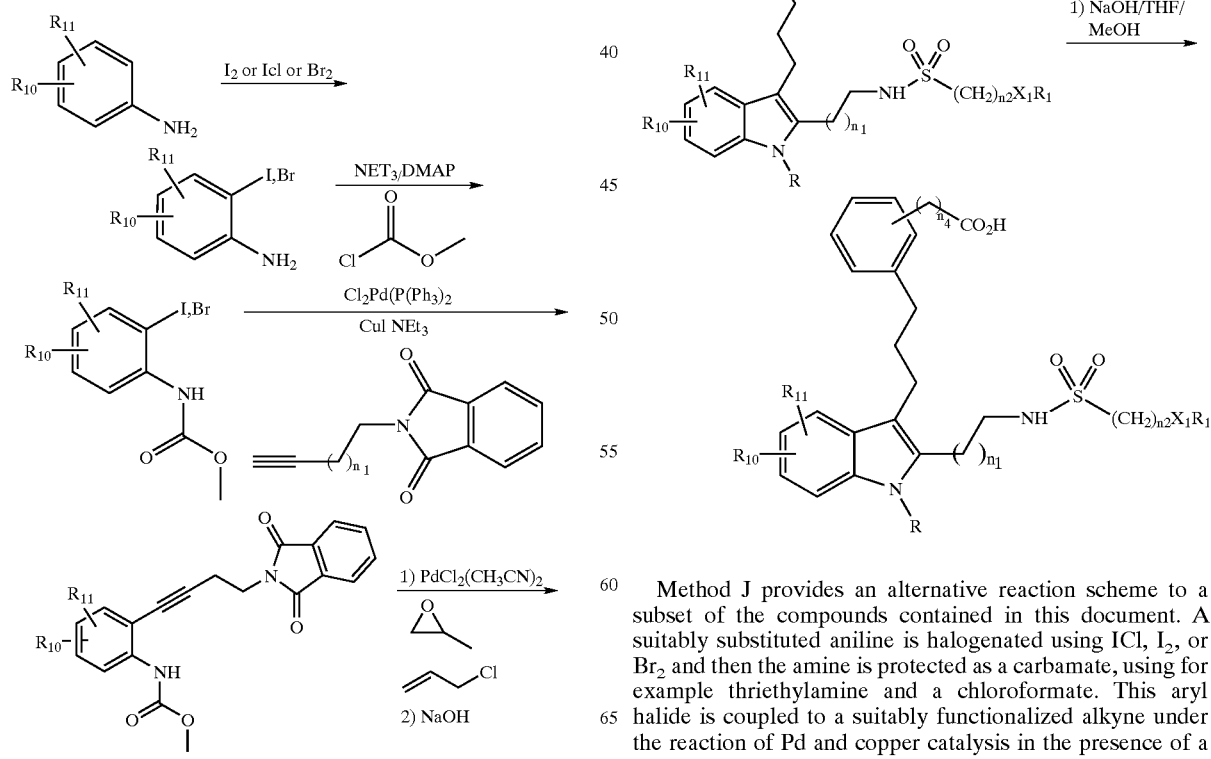

Method J provides an alternative reaction scheme to a subset of the compounds contained in this document. A suitably substituted aniline is halogenated using ICl, $I_2$, or $Br_2$ and then the amine is protected as a carbamate, using for example thriethylamine and a chloroformate. This aryl halide is coupled to a suitably functionalized alkyne under the reaction of Pd and copper catalysis in the presence of a base such as triethylamine. This resulting product could be cyclized using Pd catalysis in the presence of allyl chloride and a substituted oxirane. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate halide. The allyl indole could then be treated with 9-BBN and then a palladium catalyst follwed by an aryl or vinyl iodide to efrfect a Suzuki coupling reaction. The resulting intermediate could be deprotected usiong a hydrazine or an alkyl amine to yiled the primary amine. This amine could then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.).

Method K

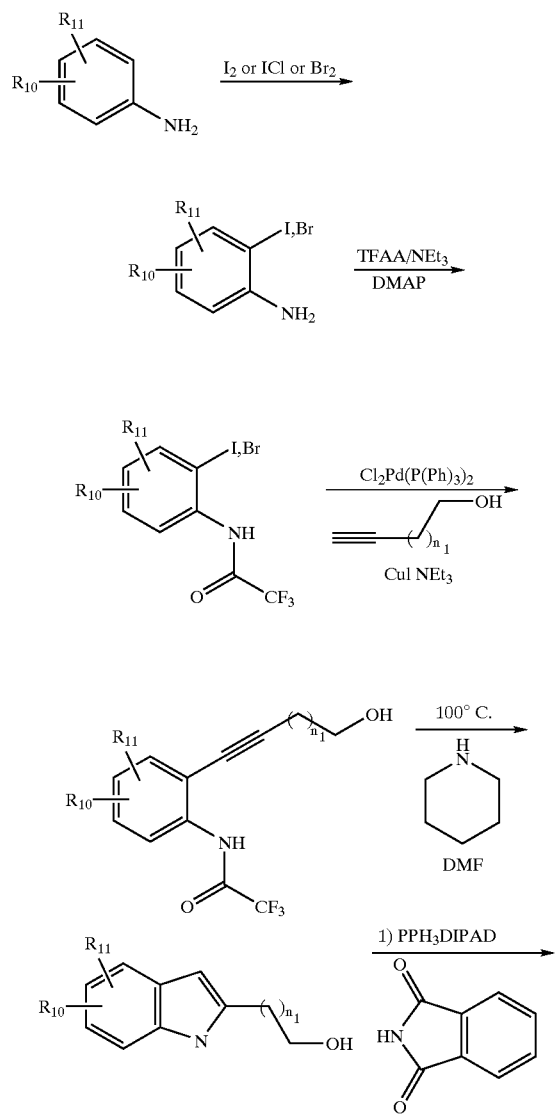

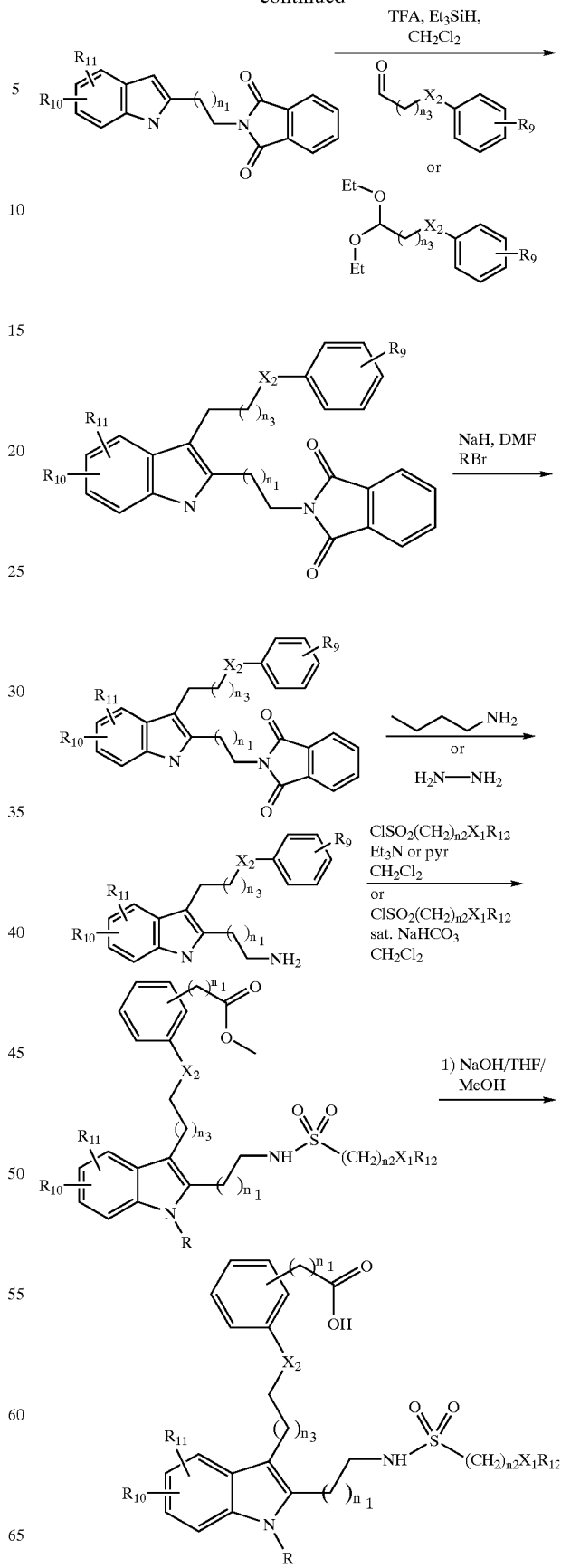

85

Method K provides an alternative method to prepare the compounds included in this document.

A suitably substituted aniline is halogenated using ICl, I₂, or Br₂ and then the amine is protected as a carbamate or amide using for example triflouroacetic anhydride triethyamine and dimethylamino pyridine. This intermediate is then reacted with a suitably functionalized alkyne under palladium and copper catalysis in the presence of a base. The resulting aryl alkyne is cyclized to the indole by heating with an amine such as piperidine. Standard Mitsunobu reaction conditions, a phosphine, an azodicarboxylate andphthalamide were used to generated the protected amine. The indole may be alkylated at the C3 position with aldehydes or the corresponding acetals in the presence of a Lewis or Bronsted acid, such as boron triflouride etherate or triflouroacetic acid. The indole nitrogen may then be alkylated by treatment with a strong base such as sodium bis(trimethylsilyl)amide, n-BuLi, sodium hydride or potassium hydride in a solvent such as DMF, DMSO or THF followed by exposure to the appropriate halide. The resulting intermediate could be deprotected usiong a hydrazine or an alkyl amine to yiled the primary amine. This amine could then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.).

Method L

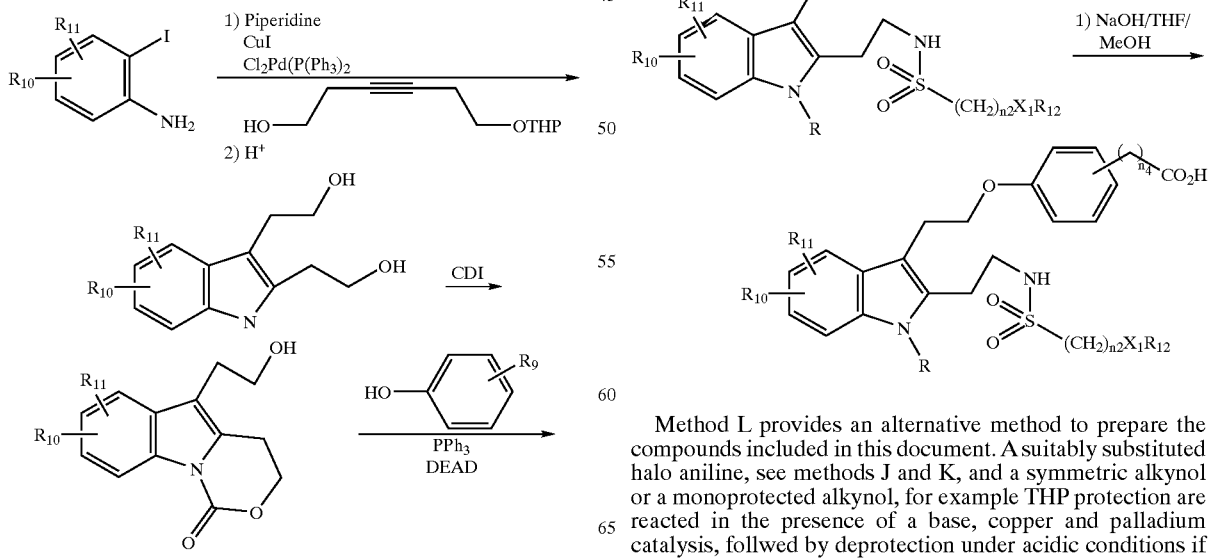

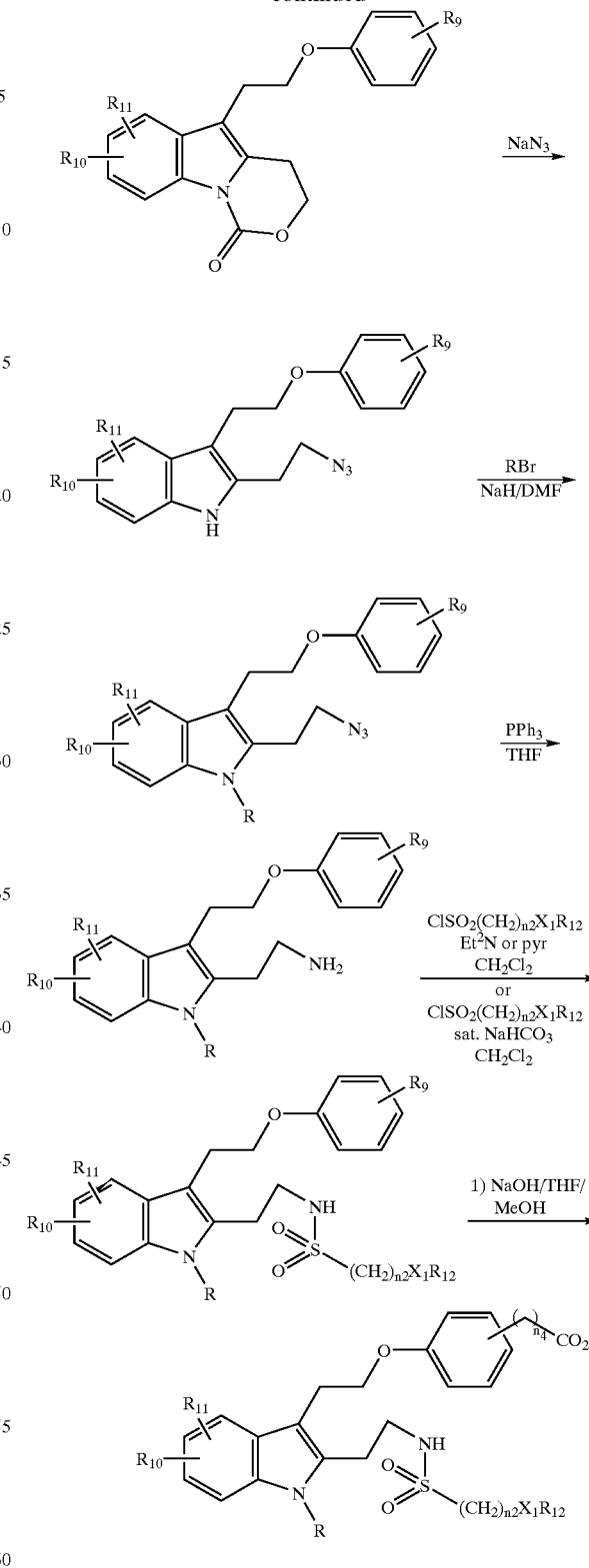

Method L provides an alternative method to prepare the compounds included in this document. A suitably substituted halo aniline, see methods J and K, and a symmetric alkynol or a monoprotected alkynol, for example THP protection are reacted in the presence of a base, copper and palladium catalysis, follwed by deprotection under acidic conditions if a monoprotected substrate is used yielded the symmetrical indole diol. The diol is dysymmetrized by treatment with carbonyl diimidazole in a suitable solvent and then the primary alcohol was substituted under standard Mitsunobu conditions, a phosphine, an azodicarboxylate and an alcohol were used to generated the desired ether. The carbamate could be opened up by reaction with sodium azide to yield the alkyl azide. The indole nitrogen may then be alkylated by treatment with a strong base such as sodium bis (trimethylsilyl)amide, n-BuLi, sodium hydride or potassium hydride in a solvent such as DMF, DMSO or THF followed by exposure to the appropriate halide. Treatment with triphenyl phosphine in wet THf delivered the desired alkyl amine. This amine could then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.).

Method M

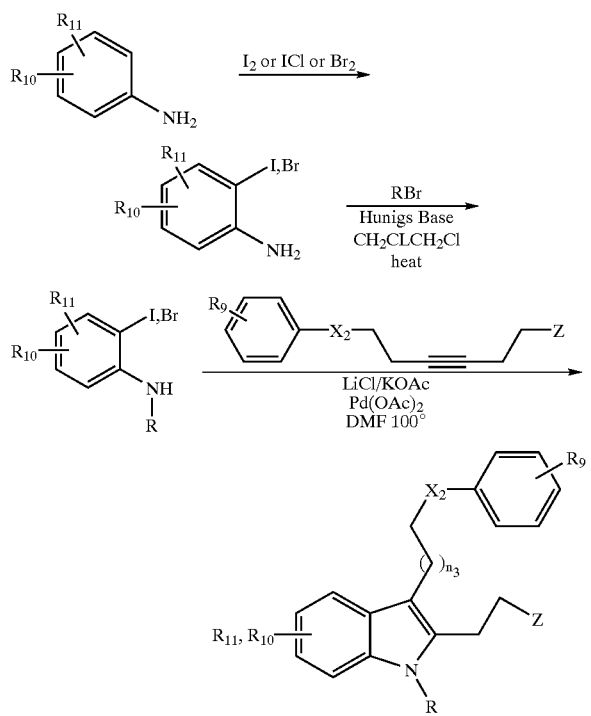

When Z = NHSO$_2$X$_1$R$_{12}$

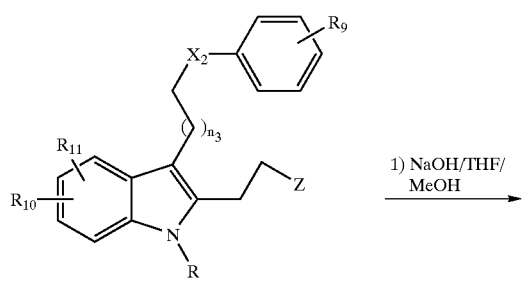

-continued

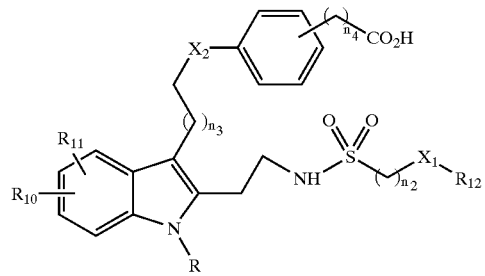

When Z = NH$_2$

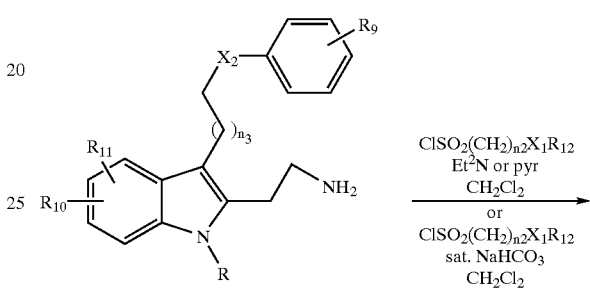

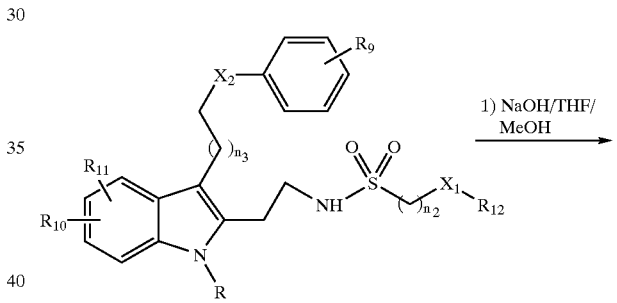

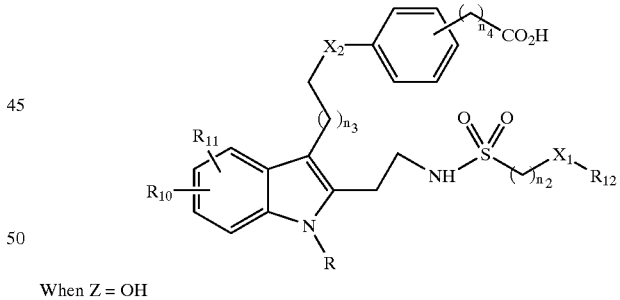

When Z = OH

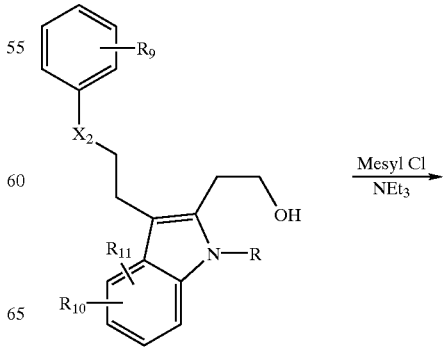

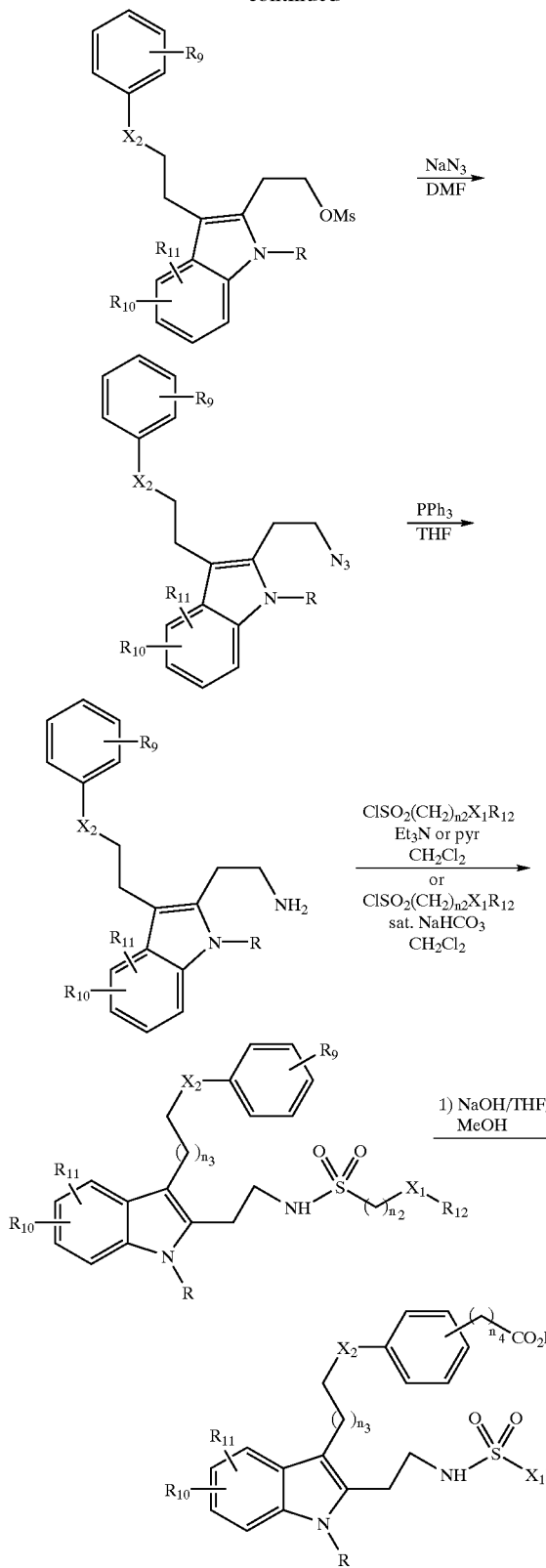

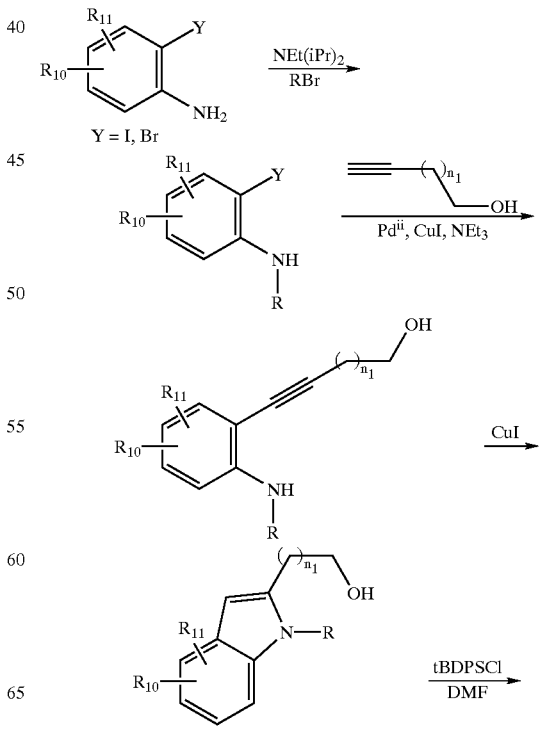

base and a halide. The thus formed alkyl amine is then reacted under palladium catalyzed conditions in the presence of a chloride souce a base and with or without a phsophine and the requisite alkyne to yield the indole. When the Z in the alkyne is $NHSO_2X_1R_1$ the synthesis is finished by hydrolysis under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.).

When $Z=NH_2$

The resulting indole could then be treated with the requisite sulfonyl chloride under biphasic conditions, aqueous sodium bicarbonate/dichloromethane, or in organic solvent with the addition of a hindered organic amine base. The final hydrolysis was accomplished under basic conditions with sodium hydroxide in water and methanol and THF at room temperature or at elevated temperature. Alternatively it may be cleaved by treatment with sodium thiomethoxide in a solvent such as THF or DMF at elevated temperatures (50° C.–100° C.).

When Z=OH

The resulting alcohol could be converted to a halide or mesylate, for example using methane sulfonyl chiroide and an organic base, which could then be displaced by sodium azide in DMF. The resulting alkyl azide could be reduced under the action of triphennyl phosphine and wet THF. The amine could be sulfonylated by the action of a sulfonyl chloride under either biphasic Shcott and Baumman conditions, Aq. Bicarbonate and dichloromethane, or under anhydrous conditions consisting of dichloromethane and an organic base such as Hunigs base. The resulting intermediate was hydrolyzed using a base, NaOH, KOH, LiOH and a mixture of solvents including an alcoholic solvent, water and tetrahydrofuran.

Method N

Method M provides an alternative strategy to furnish the compounds herein.

A suitably substituted aniline is halogenated using ICl, $I_2$, or $Br_2$ and then the amine can be alkylated using an organic

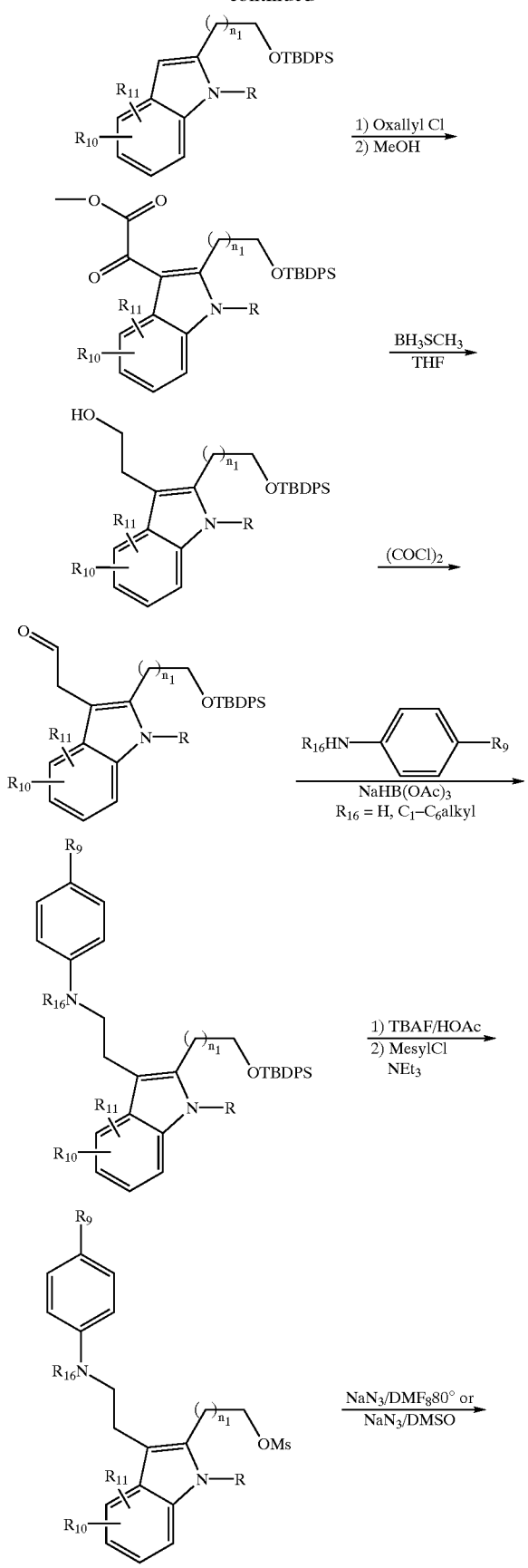
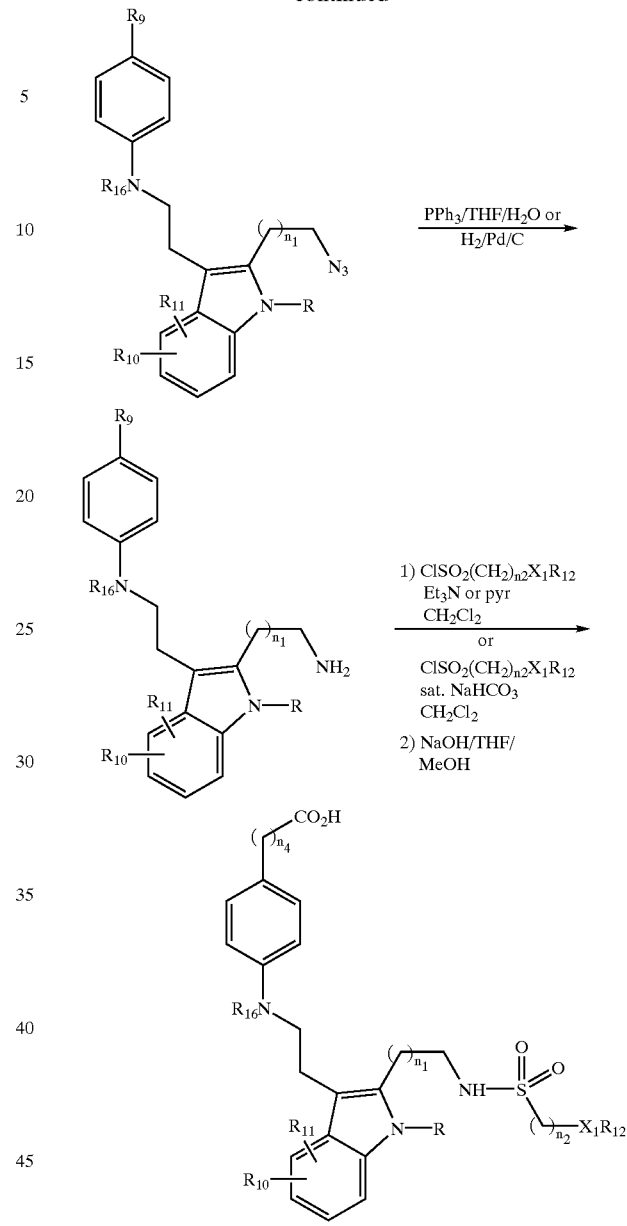

The appropriately substituted halo amine is reacted with a suitable halide and a tertiary amine base to yield an N-alkylated substrate for a Shonigishiru coupling (with an alkynol in the presence of $Pd^{ii}$ and a suitable base). This arylalkynol is cyclized to the indole under the action of a copper halide and heat. The free alcohol was protected with a silyl protecting group by reaction with a silyl chloride in the presence of a base such as imidazole. This indole was next $C_3$ acylated by reaction with a suitable acid chloride and the resulting compound reduced with most reducing agents but preferably borane or a borane complex. The primary alcohol was then oxidized to an aldehyde by any number of oxiidizing agents, including oxalyl chloride/ DMSO (swern conditions) or TPAP/NMO. This aldehyde was subjected to reductive amination conditions, which include a borohydride reducing agent and in some cases a protice acid, and a primary or secondary amine. The silyl ether was then deprotected with a flouride source including CsF, TBAF, HF etc. This free alcohol was converted into a leaving group, halide with $CBr_4$ and a phosphine, or a sulfonate ester with methane sulfonyl chloride and a tertiary amine. The activated alcohol is reacted with sodium azide in either DMF or DMSO to yield the desired azide which in turn was reduced under Staudinger conditions, phosphine and $THF/H_2O$, or via hydrogenation using hydrogen and a suitable catalyst. The amine could be sulfonylated by the action of a sulfonyl chloride under either biphasic Shcott and Baumman conditions, Aq. Bicarbonate and dichloromethane, or under anhydrous conditions consisting of dichloromethane and an organic base such as Hunigs base. The resulting intermediate was hydrolyzed using a base, NaOH, KOH, LiOH and a mixture of solvents including an alcoholic solvent, water and tetrahydrofuran.

The following Examples 142–150 were synthesized with Method N.

Example 142

4-{[2-(1-benzhydryl-2-{2-[(benzylsulfonyl)amino] ethyl}-5-chloro-1H-indol-3-yl)ethyl]amino}benzoic acid Step 1: To a solution of 4-chloro-2-iodoaniline (16.5 g, 65.1 mmol) in DMF (250 mL) at rt were added a-bromodiphenylmethane (21.5 g, 84.6 mmol) and $^iPr_2NEt$ (23 mL, 130 mmol) and the reaction mixture was heated at 45° C. overnight. After the volatile was removed under reduced pressure, the residue was dissolved in EtOAc, washed with water (3x) and brine and dried over $MgSO_4$. Purification on $SiO_2$ column chromoatography (hexanes to 5% EtOAc/hexanes) gave the desired Benzhydryl-(4-chloro-2-iodo-phenyl)-amine (26.1 g, 97% yield) as a yellowish solid.

Step 2: A mixture of benzhydryl-(4-chloro-2-iodo-phenyl)-amine (26.1 g, 62.2 mmol), $PdCl_2(PPh_3)_2$ (1.90 g, 2.67 mmol), CuI (1.2 g, 6.2 mmol), 3-butyn-1-ol, and $Et_3N$ (120 mL) was stirred at 45° C. for 20 hours. The reaction mixture was filtered through celite and rinsed with EtOAc. The filtrate was concentrated, redissolved in EtOAc, washed with water (3x) and brine, and dried over $MgSO_4$. The crude 4-[2-(Benzhydryl-amino)-5-chloro-phenyl]-but-3-yn-1-ol (25.5 g) was used in the next step directly without further purification.

Step 3: A solution of the crude 4-[2-(benzhydryl-amino)-5-chloro-phenyl]-but-3-yn-1-ol (25.5 g) and CuI (2.7 g, 14.1 mmol) in DMF (200 mL) was heated at 125° C. for 24 hours. The reaction mixture was filtered through celite and rinsed with EtOAc. The filtrate was concentrated, redissolved in EtOAc, washed with water (3x) and brine, and dried over $MgSO_4$. Silica gel column chromatography (30% EtOAc/hexanes) yielded the desired 2-(1-Benzhydryl-5-chloro-1H-indol-2-yl)-ethanol as a yellow solid (14.5 g, 73% over 2 steps).

Step 4: To a solution of 2-(1-benzhydryl-5-chloro-1H-indol-2-yl)-ethanol (15.3 g, 42.3 mmol) in $CH_2Cl_2$ (190 mL) at 0° C. were added imidazole (3.72 g, 55.0 mmol) and TBDPSCl (13.2 mL, 50.8 mmol). After stirring at the same temperature for 1.5 hours, the reaction mixture was washed with cold water (3x) and brine, and dried over $MgSO_4$. The crude silyl ether was used in the next step directly without further purification.

Step 5: To a solution of the crude silyl ether in $Et_2O$ (200 mL) at 0° C. was added oxalyl chloride (4.84 mL, 55.5 mmol) dropwise. The reaction mixture was allowed to warm to rt and stirring continued for 4 hours before $Et_3N$ (35 mL) and MeOH (10 mL) were added. The mixture was washed with water, brine, and dried over $MgSO_4$. The crude keto ester was used directly in the next step.

Step 6: To the keto ester in THF (300 mL) was added $BH_3.Me_2S$ (10M, 36 mL) dropwise at rt and the reaction mixture was refluxed overnight. The mixture was cooled at 0° C. before NaOH (30%, 150 mL) was added and stirring continued for 30 min. THF was removed under reduced pressure and the reaction mixture was extracted with EtOAc, washed with water, brine, and dried over $MgSO_4$. Purification on column chromatography (15 to 20% EtOAc/hexanes) yielded the desired product as a white solid (15.9 g, 24.7 mmol, 58% over 3 steps).

Step 7: To a solution of oxalyl chloride (0.372 mL, 4.27 mmol) in $CH_2Cl_2$ (10 mL) at −78° C. was added DMSO (0.661 mL, 9.31 mmol) dropwise. The reaction mixture was stirred at the same temperature for 5 min before a solution of 2-{1-benzhydryl-2-[2-(tert-butyl-diphenyl-silanyloxy)-ethyl]-5-chloro-1H-indol-3-yl}-ethanol (2.50 g, 3.88 mmol) in $CH_2Cl_2$ (8 mL) was introduced. After additional 40 min stirring, $^iPr_2NEt$ (3.38 mL, 19.4 mmol) was added and the reaction was quenched with cold water (5 mL) and extracted with $CH_2Cl_2$. The organic layer was dried over $MgSO_4$ and evaporated. The crude {1-Benzhydryl-2-[2-(tert-butyl-diphenyl-silanyloxy)-ethyl]-5-chloro-1H-indol-3-yl}-acetaldehyde was used directly in the next step.

Step 8: To a solution of the crude aldehyde (3.88 mmol) in 1,2-dichloroethane (39 mL) at 0° C. were added methyl 4-aminobenzoate (645 mg, 4.27 mmol), acetic acid (1.33 mL), and $NaBH(OAc)_3$. The reaction mixture was allowed to warm to rt overnight and quenched with cold $NaHCO_3$. An extractive workup furnished the desired 4-(2-{1-Benzhydryl-2-[2-(tert-butyl-diphenyl-silanyloxy)-ethyl]-5-chloro-1H-indol-3-yl}ethylamino)-benzoic acid methyl ester which was used directly in the next step without further purification.

Step 9: To 4-(2-{1-benzhydryl-2-[2-(tert-butyl-diphenyl-silanyloxy)-ethyl]-5-chloro-1H-indol-3-yl}ethylamino)-benzoic acid methyl ester (3.88 mmol) in THF (25 mL) at 0° C. was added a mixture of HOAc:1M TBAF (in THF) (2.3 mL:5.8 mL) and the reaction mixture was allowed to stir at rt for 18 h. Extractive workup followed by trituration with 5%EtOAc/hex gave the desired 4-{2-[1-Benzhydryl-5-chloro-2-(2-hydroxy-ethyl)-1H-indol-3-yl]-ethylamino}benzoic acid methyl ester with slight impurity as an off-white solid (92%, over 3 steps).

Step 10: To a solution of 4-{2-[1-benzhydryl-5-chloro-2-(2-hydroxy-ethyl)-1H-indol-3-yl]-ethylamino}-benzoic acid methyl ester (1.64 g, 3.04 mmol) in $CH_2Cl_2$ at 0° C. were added $Et_3N$ (0.636 mL, 4.56 mmol) and MsCl (0.282 mL, 3.64 mmol). After stirring at the same temperature for 35 min, the reaction mixture was quenched with cold water. An extractive workup revealed the crude mesylate as an off-white solid (1.70 g, 90%).

Step 11: A solution of the crude mesylate (1.70 g, 2.75 mmol) and $NaN_3$ (89 mg, 13.8 mmol) in DMF (14 mL) was stirred at 80° C. for 6h. The reaction mixture was diluted with EtOAc and subjected to an aqueous workup followed by flash column chromatography to yield the desired 4-{2-[2-(2-Azido-ethyl)-1-benzhydryl-5-chloro-1H-indol-3-yl]-ethylamino}benzoic acid methyl ester (813 mg, 52% yield).

Step 12: To 4-{2-[2-(2-azido-ethyl)-1-benzhydryl-5-chloro-1H-indol-3-yl]-ethylamino}-benzoic acid methyl ester (400 mg, 0.709 mmol) in THF (4 mL) at 0 C was added $Ph_3P$ (223 mg, 0.851 mmol) in portions. The reaction mixture was stirred at rt for 11 h and 35° C. for 4 h before water (50 uL) was added and stirring continued overnight.

The reaction mixture was diluted with EtOAc, dried with MgSO$_4$ and purified by flash column chromatography (EtOAc to 20%MeOH/EtOAc with 1% Et$_3$N) to give the desired 4-{2-[2-(2-Amino-ethyl)-1-benzhydryl-5-chloro-1H-indol-3-yl]-ethylamino}-benzoic acid methyl ester (201 mg, 53%) as a solid.

Step 13: The intermediate from step 8 was treated with a-toluenesulfonyl chloride according to the procedure in Example 87 step 2 to generate the desired product in 72% yield.

Step 14: The ester intermediate was hydrolyzed according to Step 8 Example 1, to afford the title acid in 87% yield. HRMS calc for [C$_{39}$H$_{36}$ClN$_3$O$_4$S+H] 678.21879 found 678.2178.

Example 143

4-({2-[1-benzhydryl-5-chloro-2-(2-{[(2-chloro-6-methylphenyl)sulfonyl]amino}ethyl)-1H-indol-3-yl]ethyl}amino)benzoic acid Step 1: The intermediate from example 142 step 12 was treated with 2-chloro-6-methyl-benzenesulfonyl chloride according to the procedure in Example 87 step 2 to generate the desired product in 85% yield.

Step 2: The ester intermediate was hydrolyzed according to Step 8 Example 1, to afford the title acid in 96% yield. HRMS calc for [C$_{39}$H$_{35}$Cl$_2$N$_3$O$_4$S+H] 712.17981 found 712.17895.

Example 144

4-({2-[1-benzhydryl-5-chloro-2-(2-{[(2-methoxyphenyl)sulfonyl]amino}ethyl)-1H-indol-3-yl]ethyl}amino)benzoic acid Step 1: The intermediate from example 142 step 12 was treated with 2-methoxy-benzenesulfonyl chloride according to the procedure in Example 87 step 2 to generate the desired product in 85% yield.

Step 2: The ester intermediate was hydrolyzed according to Step 8 Example 1, to afford the title acid in 92% yield. HRMS calc for [C$_{39}$H$_{36}$ClN$_3$O$_5$S+H] 694.2137 found 694.21311.

Example 145

4-({2-[1-benzhydryl-5-chloro-2-(2-{[(2-chlorophenyl)sulfonyl]amino}ethyl)-1H- indol-3-yl]ethyl}amino)benzoic acid Step 1: The intermediate from example 142 step 12 was treated with 2-chloro-benzenesulfonyl chloride according to the procedure in Example 87 step 2 to generate the desired product in 21% yield.

Step 2: The ester intermediate was hydrolyzed according to Step 8 Example 1, to afford the title acid in 94% yield. HRMS calc for [C$_{38}$H$_{33}$Cl$_2$N$_3$O$_4$S+H] 698.16416 found 698.16365.

Example 146

4-[[2-(1-benzhydryl-2-{2-[(benzylsulfonyl)amino]ethyl}-5-chloro-1H-indol-3- yl)ethyl](methyl)amino]benzoic acid Step 1: Crude {1-Benzhydryl-2-[2-(tert-butyl-diphenyl-silanyloxy)-ethyl]-5-chloro-1H-indol-3-yl}-acetaldehyde from step 7, example 142 was treated with 4-Methylamino-benzoic acid methyl ester according to the procedure in Example 142 step 8 to yield the desired 4-[(2-{1-Benzhydryl-2-[2-(tert-butyl-diphenyl-silanyloxy)-ethyl]-5-chloro-1H-indol-3-yl}-ethyl)-methyl-amino]-benzoic acid methyl ester in 73% yield.

Step 2: The title compound was prepared according to the procedure described for Example 142 step 9. The crude 4-({2-[1-Benzhydryl-5-chloro-2-(2-hydroxy-ethyl)-1H-indol-3-yl]-ethyl}-methyl-amino)-benzoic acid methyl ester was used in the next step directly without further purification.

Step 3-6: 4-({2-[2-(2-Azido-ethyl)-1-benzhydryl-5-chloro-1H-indol-3-yl]-ethyl}-methyl-amino)-benzoic acid methyl ester was prepared according to the procedure described for example 142 steps 10–12 in 61% (3 steps).

Step 7: A solution of 4-({2-[2-(2-azido-ethyl)-1-benzhydryl-5-chloro-1H-indol-3-yl]-ethyl}-methyl-amino)-benzoic acid methyl ester (410 mg, 0.709 mmol) and 10% Pd/C (155 mg) in MeOH:CH$_2$Cl$_2$ (=7 mL:1 mL) was stirred under H$_2$ atmosphere (1 atm) for 2 h 15 min. The reaction mixture was filtered through celite and rinsed with MeOH and CH$_2$Cl$_2$. Flash column chromatography (CH$_2$Cl$_2$ to 8% MeOH/CH$_2$Cl$_2$) of the residue gave the desired 4-({2-[2-(2-Amino-ethyl)-1-benzhydryl-5-chloro-1H-indol-3-yl]-ethyl}methyl-amino)-benzoic acid methyl ester in 78% yield (305 mg).

Step 8: The intermediate from step 7 was treated with α-toluenesulfonyl chloride according to the procedure in Example 87 step 2 to generate the desired product in 83% yield.

Step 9: The ester intermediate was hydrolyzed according to Step 8 Example 1, to afford the title acid in 91% yield. HRMS calc for [C$_{39}$H$_{38}$ClN$_3$O$_4$S+H] 692.23444 found 692.23374.

Example 147

4-[{2-[1-benzhydryl-5chloro-2-(2-{[(3,4-dichlorobenzyl)sulfonyl]amino}ethyl)-1H-indol-3-yl]ethyl}(methyl)amino]benzoic acid Step 1: The intermediate from example 146 step 7 was treated with 3,4-dichlorophenylmethanesulfonylchloride according to the procedure in Example 87 step 2 to generate the desired product in 87% yield.

Step 2: The ester intermediate was hydrolyzed according to Step 8 Example 1, to afford the title acid in 68% yield. HRMS calc for [C$_{40}$H$_{36}$Cl$_3$N$_3$O$_4$S+H] 760.15649 found 760.1573.

Example 148

4-[{2-[1-benzhydryl-5-chloro-2-(2-{[(2-chloro-6-methylphenyl)sulfonyl]amino}ethyl)-1H-indol-3-yl]ethyl}(methyl)amino]benzoic acid Step 1: The intermediate from example 146 step 7 was treated with 2-chloro-6-methyl-benzenesulfonyl chloride according to the procedure in Example 87 step 2 to generate the desired product in 96% yield.

Step 2: The ester intermediate was hydrolyzed according to Step 8 Example 1, to afford the title acid in 88% yield. HRMS calc for [C$_{40}$H$_{37}$Cl$_2$N$_3$O$_4$S+H] 726.19546 found 726.19461.

Example 149

4-[{2-[1-benzhydryl-5-chloro-2-(2-{[(2-chlorophenyl)sulfonyl]amino}ethyl)-1H-indol-3-yl]ethyl}(methyl)amino]benzoic acid Step 1: The intermediate from example 146 step 7 was treated with 2-chlorobenzenesulfonyl chloride according to the procedure in Example 87 step 2 to generate the desired product in 96% yield.

Step 2: The ester intermediate was hydrolyzed according to Step 8 Example 1, to afford the title acid in 84% yield. HRMS calc for $[C_{39}H_{35}Cl_2N_3O_4S+H]$ 712.17981 found 712.17966.

Example 150

4-[{2-[1-benzhydryl-5-chloro-2-(2-{[(2-methoxyphenyl)sulfonyl]amino}ethyl)-1H-indol-3-yl]ethyl}(methyl)amino]benzoic acid Step 1: The intermediate from example 146 step 7 was treated with 2-methoxy-benzenesulfonyl chloride according to the procedure in Example 87 step 2 to generate the desired product in 95% yield.

Step 10: The ester intermediate was hydrolyzed according to Step 8 Example 1, to afford the title acid in 73% yield. HRMS calc for $[C_{40}H_{38}ClN_3O_5S+H]$ 708.22935 found 708.2286.

Coumarine Assay 7-hydroxycoumarinyl 6-heptenoate was used as a monomeric substrate for cPLA2 as reported previously (Huang, Z. et al., 1994, Nalytical Biochemistry 222, 110–115). Inhibitors were mixed with 200 μL assay buffer (80 mM Heped, pH 7.5, 1 mM EDTA) containing 60 μM 7-hydroxycoumarinyl 6-heptenoate. The reaction was initiated by adding 4 μg cPLA2 in 50 μL assay buffer. Hydrolysis of the 7-hydroxycounarimyl 6-heptenoate ester was monitored in a fluorometer by exciting at 360 nm and monitoring emission at 460 nm. Enzyme activity is proportional to the increase in emission at 460 nm per minute. In the presence of a cPLA2 inhibitor, the rate of increase is less.

| Example # | Coumarin IC$_{50}$ (μM) |
|---|---|
| Example 1 | 0.42 |
| Example 2 | 2 |
| Example 3 | 2.5 |
| Example 4 | 56 |
| Example 5 | 3 |
| Example 6 | 2.0 |
| Example 7 | 0.55 |
| Example 8 | 2 |
| Example 9 | 0.7 |
| Example 10 | 0.57 |
| Example 11 | 0.45 |
| Example 12 | 150 |
| Example 13 | 0.64 |
| Example 14 | 0.8 |
| Example 15 | 0.63 |
| Example 16 | 0.98 |
| Example 17 | 0.2 |
| Example 18 | 0.4 |
| Example 19 | 0.31 |
| Example 20 | 1.1 |
| Example 21 | 1.1 |
| Example 22 | 1.8 |
| Example 23 | 1.5 |
| Example 24 | 0.34 |
| Example 25 | 3.4 |
| Example 26 | 1.1 |
| Example 27 | 0.8 |
| Example 28 | 0.95 |
| Example 29 | 0.19 |
| Example 30 | 0.15 |
| Example 31 | 0.15 |
| Example 32 | 0.085 |
| Example 33 | 2.9 |

-continued

| Example # | Coumarin IC$_{50}$ (μM) |
|---|---|
| Example 35 | 0.33 |
| Example 36 | 0.5 |
| Example 37 | 0.37 |
| Example 38 | 0.5 |
| Example 39 | 0.32 |
| Example 40 | 0.73 |
| Example 41 | 0.2 |
| Example 42 | 0.18 |
| Example 43 | 0.2 |
| Example 44 | 0.25 |
| Example 45 | 4.7 |
| Example 46 | 4.8 |
| Example 47 | 0.58 |
| Example 48 | 2.35 |
| Example 49 | 1.1 |
| Example 50 | 0.69 |
| Example 51 | 2.2 |
| Example 52 | 0.13 |
| Example 53 | 0.37 |
| Example 54 | 0.31 |
| Example 55 | 0.26 |
| Example 56 | 0.13 |
| Example 57 | 0.28 |
| Example 58 | 0.36 |
| Example 59 | 0.29 |
| Example 60 | 0.15 |
| Example 61 | 0.34 |
| Example 62 | 0.38 |
| Example 63 | 0.30 |
| Example 64 | 0.12 |
| Example 65 | 0.13 |
| Example 66 | 0.15 |
| Example 67 | 0.14 |
| Example 68 | 0.16 |
| Example 69 | 0.15 |
| Example 70 | 0.18 |
| Example 71 | 0.45 |
| Example 72 | 0.28 |
| Example 73 | 0.30 |
| Example 74 | 0.28 |
| Example 75 | 0.4 |
| Example 76 | 0.4 |
| Example 77 | 0.48 |
| Example 78 | 0.34 |
| Example 79 | 0.15 |
| Example 80 | 3.7 |
| Example 81: | 0.47 |
| Example 82: | 0.5 |
| Example 83 | 0.45 |
| Example 84 | 0.5 |
| Example 85 | 0.4 |
| Example 86 | 0.6 |
| Example 87 | 1.2 |
| Example 88 | <7.4 |
| Example 89 | 0.38 |
| Example 90 | 0.65 |
| Example 91 | 0.5 |
| Example 92 | 1.0 |
| Example 93 | 0.56 |
| Example 94 | 0.8 |
| Example 95 | 0.85 |
| Example 96 | 0.95 |
| Example 97 | 0.95 |
| Example 98 | 1.1 |

-continued

| Example # | Coumarin IC$_{50}$ ($\mu$M) |
|---|---|
| Example 99 | 1.0 |
| Example 100 | 0.12 |
| Example 101 | 0.1 |
| Example 102 | 0.19 |
| Example 103 | 1.1 |
| Example 104 | 1.1 |
| Example 105 | 0.65 |
| Example 106 | 0.22 |
| Example 107 | 0.33 |
| Example 108 | 0.15 |
| Example 109 | 0.4 |
| Example 110 | 0.5 |
| Example 111 | 1.0 |
| Example 112 | 1.2 |
| Example 113 | 1.3 |
| Example 114 | 1.1 |
| Example 115 | 0.9 |
| Example 116 | 1.2 |
| Example 117 | 1.6 |
| Example 118 | 0.4 |
| Example 119 | 0.4 |
| Example 120 | 0.4 |
| Example 121 | 0.46 |
| Example 122 | 2.5 |
| Example 123 | 1.7 |
| Example 124 | 0.8 |
| Example 125 | 1.4 |
| Example 126 | 0.2 |
| Example 127 | 0.2 |
| Example 128 | 0.32 |
| Example 129 | 0.13 |
| Example 130 | 0.17 |
| Example 131 | 0.2 |
| Example 132 | 0.2 |
| Example 133 | 0.09 |
| Example 134 | >1 |
| Example 135 | 0.2 |
| Example 136 | 0.18 |
| Example 137 | NT |
| Example 138 | 0.2 |
| Example 139 | 1.7 |
| Example 140 | 0.2 |
| Example 141 | 0.17 |

Many variations of the present invention not illustrated herein will occur to those skilled in the art. The present invention is not limited to the embodiments illustrated and described herein, but encompasses all the subject matter within the scope of the appended claims

What is claimed is:

1. A compound of the formula

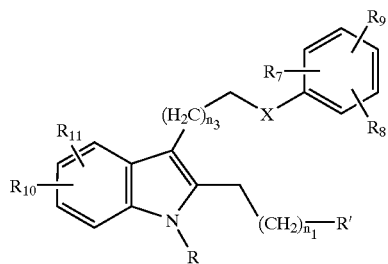

wherein

R is —$(CH_2)_n$—A, —$(CH_2)_n$—S—A, or —$(CH_2)_n$—O—A, where A represents:

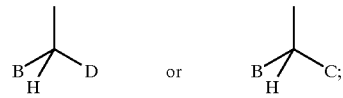

D represents $C_1$–$C_6$ alkyl, $C_1$–$C_6$ alkoxy, —$CF_3$ or —$C_{1-3}$alkyl—$CF_3$, B and C are each independently selected from the group consisting of phenyl, pyridinyl, pyrimidinyl, furanyl, thiophenyl or pyrrolyl groups, each optionally substituted by from 1 to 3, substituents selected independently from the group consisting of H, halogen, —CN, —CHO, —$CF_3$, —$OCF_3$, —OH, —$C_1$–$C_6$ alkyl, $C_1$–$C_6$ alkoxy, —$NH_2$, —$N(C_1$–$C_6)_2$, —$NH(C_1$–$C_6)$, —N—C(O)—$(C_1$–$C_6)$, —$NO_2$, or by a 5- or 6-membered heterocyclic or heteroaromatic ring containing 1 or 2 heteroatoms selected from O, N or S;

R' is selected from the group consisting of —$CH_2$—OH, —$CH_2$—NH—$S(O)_2$—$(CH_2)_{n2}$-halo, —$CH_2$—NH—$S(O)_2$—CH=CH, —$CH_2$—$NH_2$, or a protected form of —$CH_2$—$NH_2$;

$R_7$ and $R_8$ are independently selected from H, halogen, —CN, —CHO, —$CF_3$, —$OCF_3$, —OH, —$C_1$–$C_6$ alkyl, $C_1$–$C_6$ alkoxy, $C_1$–$C_6$ thioalkyl, —$NH_2$, —$N(C_1$–$C_6)_2$, —$NH(C_1$–$C_6)$, —N—C(O)—$(C_1$–$C_6)$, or —$NO_2$;

$R_9$ represents —$(CH_2)_{n4}$—$CO_2H$, a $C_1$–$C_8$ alkyl ester of —$(CH_2)_{n4}$—$CO_2H$, or a pharmaceutically acceptable acid mimic or mimetic;

$R_{10}$ is selected from H, halogen, —CN, —CHO, —$CF_3$, —$OCF_3$, —OH, —$C_1$–$C_6$ alkyl, $C_1$–$C_6$ alkoxy, $C_1$–$C_6$ thioalkyl, —$NH_2$, —$N(C_1$–$C_6)_2$, —$NH(C_1$–$C_6)$, —N—C(O)—$(C_1$–$C_6)$, or —$NO_2$;

$R_{11}$ is selected from H, halogen, —CN, —CHO, —$CF_3$, —$OCF_3$, —OH, —$C_1$–$C_6$ alkyl, $C_1$–$C_6$ alkoxy, $C_1$–$C_6$ thioalkyl, —$NH_2$, —$N(C_1$–$C_6)_2$, —$NH(C_1$–$C_6)$, —N—C(O)—$(C_1$–$C_6)$, —$NO_2$, —N—C(O)—N$(C_1$–$C_3$ alkyl$)_2$, —N—C(O)—NH$(C_1$–$C_3$ alkyl), —N—C(O)—O—$(C_1$–$C_3$ alkyl), —$SO_2$—$C_1$–$C_6$ alkyl, —S—$C_3$–$C_6$ cycloalkyl, —S—$CH_2$–$C_3$–$C_6$ cycloalkyl, —$SO_2$—$C_3$–$C_6$ cycloalkyl, , —$SO_2$—$CH_2$—$C_3$–$C_6$ cycloalkyl, $C_3$–$C_6$ cycloalkyl, —$CH_2$—$C_3$–$C_6$ cycloalkyl, —O—$C_3$–$C_6$ cycloalkyl, , —O—$CH_2$—$C_3$–$C_6$ cycloalkyl, phenyl, benzyl, benzyloxy, morpholino, pyrrolidino, piperidine, piperizine, furan, thiophene, imidazole, tetrazole, pyrazine, pyrazolone, pyrazole, imidazole, oxazole or isoxazole, the rings of each of these groups each being optionally substituted by from 1 to 3 substituents selected from the group of H, halogen, —CN, —CHO, —$CF_3$, —OH, —$C_1$–$C_6$ alkyl, $C_1$–$C_6$ alkoxy, —$NH_2$, —$N(C_1$–$C_6)_2$, —$NH(C_1$–$C_6)$, —N—C(O)—$(C_1$–$C_6)$, —$NO_2$, —$SO_2(C_1$–$C_3$ alkyl), —$SO_2NH(C_1$–$C_3$ alkyl), —$SO_2N(C_1$–$C_3$ alkyl$)_2$, or $OCF_3$;

n is an integer from 0 to 3;

$n_1$ is an integer from 0 to 3;

$n_2$ is an integer from 0 to 3

$n_3$ is an integer from 0 to 3;

$n_4$ is an integer from 0 to 2; and,

X is a linking group selected from the group consisting of of —O—, —$CH_2$—, —$SO_2$—, —NH—, and —$N(C_1$–$C_6$-alkyl)—.

2. A compound according to claim 1 having the formula

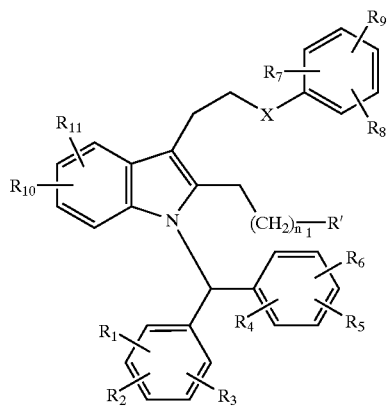

wherein:

R', $R_{7-11}$, X, $n_1$, $n_2$ and $n_4$ are as defined in claim 1 and $R_1$, $R_2$, $R_3$, $R_4$, $R_5$ and $R_6$ are each independently selected from the group consisting of H, halogen, —CN, —CHO, —CF$_3$, —OCF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), —NO$_2$, or a 5- or 6-membered heterocyclic or heteroaromatic ring containing 1 or 2 heteroatoms selected from O, N or S.

3. A compound according to claim 2 wherein the halogen atom in the R' group —CH$_2$—NH—S(O)$_2$—(CH$_2$)$_{n2}$-halo is bromine or chlorine.

4. A compound according to claim 2 having the formula

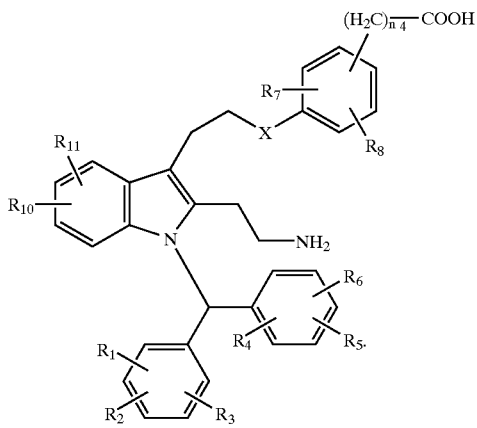

5. A compound according to claim 4 wherein $R_1$, $R_2$, $R_3$, $R_4$, $R_5$ and $R_6$ are each H.

6. A compound according to claim 1 having the formula

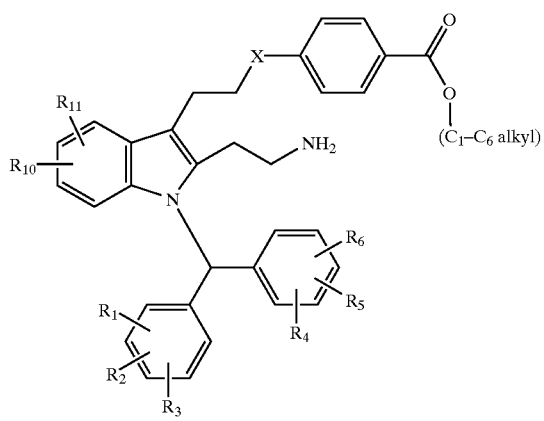

wherein $R_1$, $R_2$, $R_3$, $R_4$, $R_5$ and $R_6$ are each independently selected from H, halogen, —CN, —CHO, —CF$_3$, —OCF$_3$, —OH, —C$_1$–C$_6$ alkyl, C$_1$–C$_6$ alkoxy, —NH$_2$, —N(C$_1$–C$_6$)$_2$, —NH(C$_1$–C$_6$), —N—C(O)—(C$_1$–C$_6$), —NO$_2$, or a 5- or 6-membered heterocyclic or heteroaromatic ring containing 1 or 2 heteroatoms selected from O, N or S.

7. A compound according to claim 6 wherein $R_1$, $R_2$, $R_3$, $R_4$, $R_5$ and $R_6$ are each H.

8. A compound selected form the group consisting of:

4-{2-[2-(2-Amino-ethyl)-1-benzyhydryl-5-chloro-1H-indol-3-yl]-ethanesulfonyl}-benzoic acid methyl ester;

4-{2-[2-(2-Amino-ethyl)-1-benzyhydryl-5-chloro-1H-indol-3-yl]-ethoxy}-benzoic acid methyl ester;

4-{3-[2-(2-Amino-ethyl)-1-benzyhydryl-5-chloro-1H-indol-3-yl]-propyl}-benzoic acid methyl ester;

4-{2-[2-(2-Amino-ethyl)-1-benzhydryl-5-chloro-1H-indol-3-yl]-ethylamino}-benzoic acid methyl ester; and 4-({2-[2-(2-Amino-ethyl)-1-benzhydryl-5-chloro-1H-indol-3-yl]-ethyl}-methyl-amino)-benzoic acid methyl ester.

* * * * *